US012385091B2

(12) United States Patent
Fisher et al.

(10) Patent No.: US 12,385,091 B2
(45) Date of Patent: Aug. 12, 2025

(54) IMMOBILIZATION IN FLOW CELLS

(71) Applicant: ILLUMINA, INC., San Diego, CA (US)

(72) Inventors: Jeffrey S. Fisher, San Diego, CA (US); Tarun Kumar Khurana, Fremont, CA (US); Mathieu Lessard-Viger, San Diego, CA (US); Clifford Lee Wang, Berkeley, CA (US); Yir-Shyuan Wu, Albany, CA (US)

(73) Assignee: Illumina, Inc., San Diego, CA (US)

( * ) Notice: Subject to any disclaimer, the term of this patent is extended or adjusted under 35 U.S.C. 154(b) by 752 days.

(21) Appl. No.: 17/600,526

(22) PCT Filed: Dec. 11, 2020

(86) PCT No.: PCT/US2020/064559
§ 371 (c)(1),
(2) Date: Sep. 30, 2021

(87) PCT Pub. No.: WO2021/119459
PCT Pub. Date: Jun. 17, 2021

(65) Prior Publication Data
US 2022/0195519 A1  Jun. 23, 2022

Related U.S. Application Data

(60) Provisional application No. 62/946,717, filed on Dec. 11, 2019.

(51) Int. Cl.
C12Q 1/68 (2018.01)
C12Q 1/6874 (2018.01)
G01N 1/40 (2006.01)

(52) U.S. Cl.
CPC ......... *C12Q 1/6874* (2013.01); *G01N 1/4044* (2013.01); *G01N 2001/4038* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 9,429,507 B2 | 8/2016 | Matsui et al. | |
| 11,725,179 B2 | 8/2023 | Takeda et al. | |
| 2006/0078895 A1* | 4/2006 | Peck | B01J 19/0046 427/2.11 |
| 2009/0263417 A1 | 10/2009 | Yamamoto | |
| 2009/0264317 A1 | 10/2009 | Ofir et al. | |
| 2009/0272914 A1 | 11/2009 | Feng et al. | |
| 2010/0081175 A1 | 4/2010 | Takubo | |
| 2013/0118905 A1 | 5/2013 | Morimoto | |
| 2020/0102587 A1 | 4/2020 | Yokoi et al. | |

FOREIGN PATENT DOCUMENTS

| | | |
|---|---|---|
| RU | 2008144969 A | 5/2010 |
| RU | 152297 U1 | 5/2015 |
| WO | 2011149032 A1 | 7/2013 |
| WO | 2013150869 A1 | 10/2013 |
| WO | 2016154193 A1 | 9/2016 |
| WO | 2017059353 A1 | 4/2017 |
| WO | 2016182034 A1 | 3/2018 |
| WO | 2019028047 A1 | 2/2019 |
| WO | 2019028166 A1 | 2/2019 |
| WO | 2019089581 A1 | 5/2019 |
| WO | 2019126040 A1 | 6/2019 |
| WO | 2019160820 A1 | 8/2019 |
| WO | 2018185871 A1 | 12/2019 |

OTHER PUBLICATIONS

Lan et al., "Single-cell genome sequencing at ultra-high-throughput with microfluidic droplet barcoding", Nature Biotechnology, vol. 35, No. 7, p. 640-646, Jul. 1, 2017.

* cited by examiner

*Primary Examiner* — Kenneth R Horlick
(74) *Attorney, Agent, or Firm* — Dierker & Kavanaugh, P.C.

(57) ABSTRACT

In an example, a target material is immobilized on two opposed sequencing surfaces of a flow cell using first and second fluids. The first fluid has a density less than a target material density and the second fluid has a density greater than the target material density; or the second fluid has a density less than the target material density and the first fluid has a density greater than the target material density. The first fluid (including the target material) is introduced into the flow cell, whereby at least some of the target material becomes immobilized by capture sites on one of the sequencing surfaces. The first fluid and non-immobilized target material are removed. The second fluid (including target material) is introduced into the flow cell, whereby at least some of the target material becomes immobilized by capture sites on another of the sequencing surfaces.

10 Claims, 15 Drawing Sheets

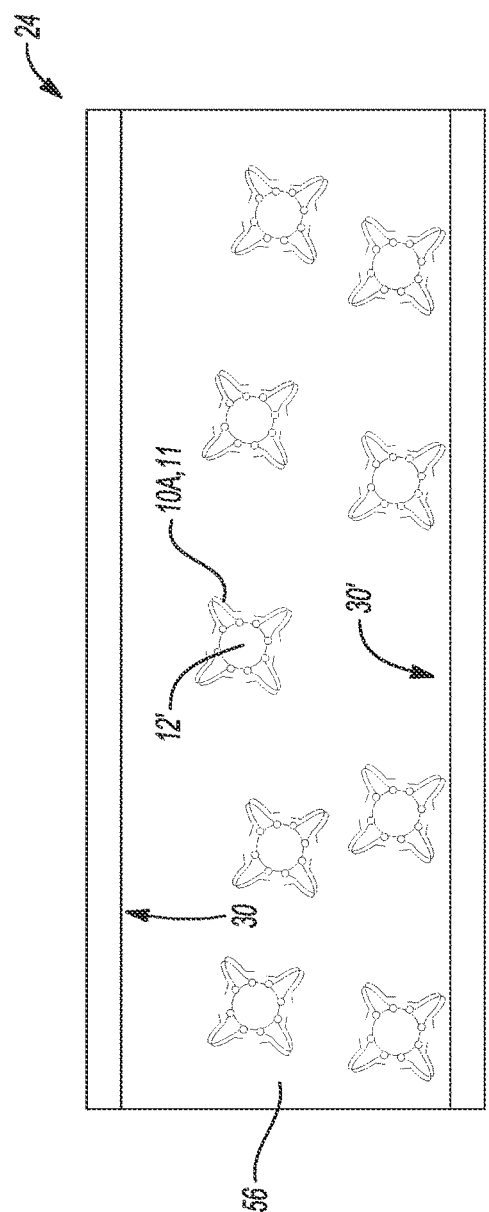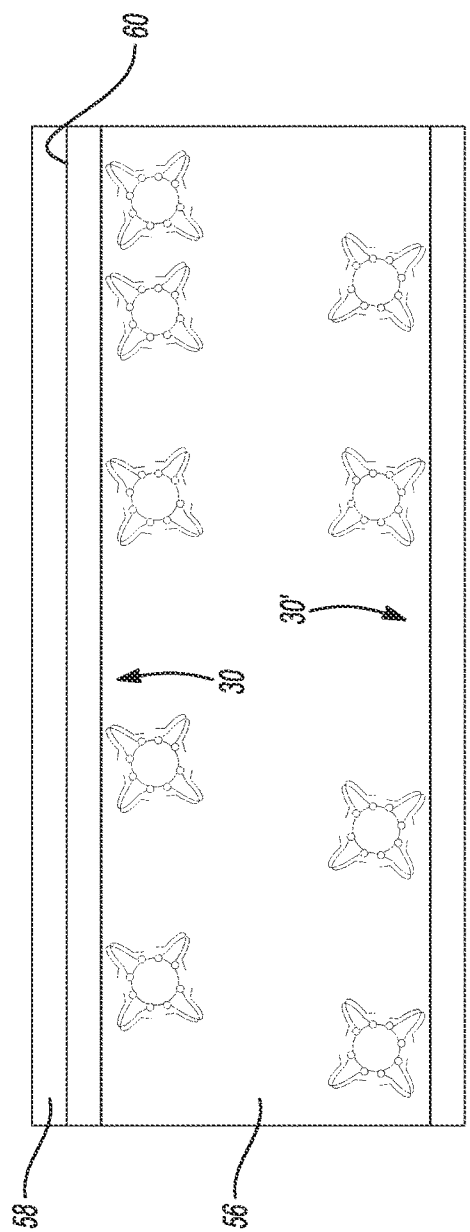

IMMOBILIZATION IN FLOW CELLS

CROSS-REFERENCE TO RELATED APPLICATION

This application claims the benefit of U.S. Provisional Application Ser. No. 62/946,717, filed Dec. 11, 2019, the contents of which is incorporated by reference herein in its entirety.

BACKGROUND

Flow cells are used in a variety of methods and applications, such as gene sequencing, genotyping, etc. In some methods and applications, it is desirable to generate a library of fragmented and tagged DNA molecules from double-stranded DNA (dsDNA) target molecules. Often, the purpose is to generate smaller DNA molecules (e.g., DNA fragments) from larger dsDNA molecules for use as templates in DNA sequencing reactions. The templates may enable short read lengths to be obtained. During data analysis, overlapping short sequence reads can be aligned to reconstruct the longer nucleic acid sequences. In some instances, pre-sequencing steps (such as barcoding of particular nucleic acid molecules) can be used to simplify the data analysis.

SUMMARY

Some of the example kits and methods set forth herein are suitable for immobilizing one or more target materials on opposed surfaces of a flow cell. Some examples of the method enable sequential immobilization, and other examples of the method enable simultaneous immobilization.

A first aspect disclosed herein is a method comprising immobilizing a target material at each of two opposed sequencing surfaces of a flow cell, wherein the immobilizing involves: introducing a first fluid, including a first portion of the target material therein, into the flow cell, whereby at least some of the target material becomes immobilized by capture sites on one of the two opposed sequencing surfaces; removing the first fluid and any non-immobilized target material from the flow cell; and introducing a second fluid, including a second portion of the target material therein, into the flow cell, whereby at least some of the target material becomes immobilized by capture sites on another of the two opposed sequencing surfaces; wherein one of: the first fluid has a density less than a density of the target material and the second fluid has a density greater than the density of the target material; or the second fluid has the density less than the density of the target material and the first fluid has the density greater than the density of the target material.

A second aspect disclosed herein is a kit, comprising a preparation fluid including a target material therein; a first introduction fluid having a density less than a density of the target material; and a second introduction fluid having a density greater than the density of the target material.

A third aspect disclosed herein is a method comprising immobilizing a target material at each of two opposed sequencing surfaces of a flow cell by: introducing a fluid, including the target material, into the flow cell, wherein: the target material includes: a magnetic solid support; and sequencing-ready nucleic acid fragments or template strands attached to the magnetic solid support; and the fluid has a density at least approximately equivalent to a density of the magnetic solid support; allowing some of the target material to become immobilized by capture sites on one of the two opposed sequencing surfaces; and applying a magnetic force to another of the two opposed sequencing surfaces, thereby pulling some other of the target material to the other of the two opposed sequencing surfaces where they become immobilized by capture sites on the other of the two opposed sequencing surfaces.

A fourth aspect disclosed herein is a method comprising simultaneously immobilizing first target materials at a first of two opposed sequencing surfaces of a flow cell and second target materials at a second of the two opposed sequencing surfaces by introducing, into the flow cell, a target fluid including the first target materials and the second target materials, wherein: a carrier fluid of the target fluid has a fluid density; the first target material has a first density less than the fluid density; and the second target material has a second density greater than the fluid density.

A fifth aspect disclosed herein is a target fluid, comprising a carrier fluid having a fluid density; a first target material having a first density less than the fluid density; and a second target material having a second density greater than the fluid density.

A sixth aspect disclosed herein is a method comprising introducing first and second target materials to a flow cell including two opposed sequencing surfaces, wherein the first target material has at least one property that is different from the second target material, wherein the at least one property is selected from the group consisting of density, charge, magnetism, and combinations thereof; and exposing the first and second target materials to at least one condition, thereby causing the first target material to become immobilized by a capture site on a first of the two opposed sequencing surfaces and the second target material to become immobilized by a capture site on a second of the two opposed sequencing surfaces.

It is to be understood that any features of the any one of the aspects may be combined together in any desirable manner. Moreover, it is to be understood that any combination of features of the first aspect and/or of the second aspect and/or of the third aspect and/or of the fourth aspect and/or of the fifth aspect and/or of the sixth aspect may be combined with any of the examples disclosed herein to achieve the benefits as described in this disclosure, including, for example, a more uniform distribution of target material across sequencing surfaces in a flow cell.

Another example set forth herein is suitable for reducing or preventing migration of template strands during on flow cell amplification.

As such, a seventh aspect disclosed herein is a method comprising introducing sequencing-ready nucleic acid fragments to a flow cell, thereby seeding at least some of the sequencing-ready nucleic acid fragments to respective primers on a sequencing surface of the flow cell; removing non-seeded sequencing-ready nucleic acid fragments from the flow cell; introducing an amplification mix including a liquid form of a temperature responsive material to the flow cell; causing the liquid form of the temperature responsive material to gel; initiating amplification of the seeded sequencing-ready nucleic acid fragments to generate template strands, whereby the gel form of the temperature responsive material reduces diffusion of the template strands; causing the gel form of the temperature responsive material to liquify; and removing the liquid form of the temperature responsive material from the flow cell.

It is to be understood that any features of the seventh aspect may be combined together in any desirable manner. Moreover, it is to be understood that any combination of features of the seventh aspect may be combined with any of the other aspects and/or any of the examples disclosed herein to achieve the benefits as described in this disclosure, including, for example, a more uniform distribution of target material across sequencing surfaces in a flow cell and reduced migration of template strands during on flow cell amplification.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 4A and 4B together depict another example of a method disclosed herein;

DETAILED DESCRIPTION

Figure 1A:
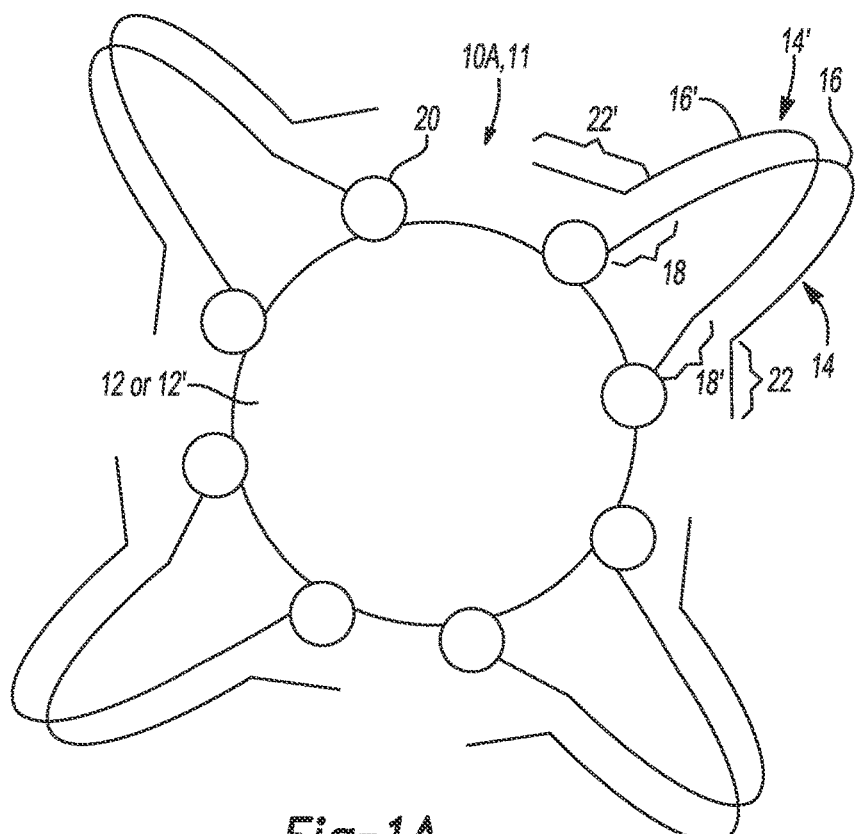
FIGS. 1A through 1C are schematic illustrations of different examples of the target materials disclosed herein.

Some sequencing techniques utilize sequencing-ready nucleic acid fragments. In some examples, each sequencing-ready nucleic acid fragment includes a portion (fragment) of genetic material, as well as adapters at the 3' and 5' ends. Sequencing-ready nucleic acid fragments may be bound to a solid support, which forms a complex. In these examples, the use of the solid support may be desirable because it can preserve the contiguity information of the longer genetic material from which the fragments are generated. Other sequencing techniques utilize a clustered solid support, which includes a cluster of template strands attached to the solid support. In these examples, the use of the solid support may be desirable because amplification (formation of the template strands) can be performed off of the flow cell and thus the flow cell chemistry is simplified in that it does not include amplification primers. However, when these target materials (e.g., complexes or clustered solid supports) are used in flow cells having two sequencing surfaces positioned opposite one another (e.g., an upper/top surface and a lower/bottom surface), it has been found that the target materials have a tendency to sink to the sequencing surface positioned at the bottom of the flow cell. Similar issues may arise when other target materials, such as protein biomarkers, microbiomes, lysates, etc. in flow cells with opposed surfaces.

Some examples of the method disclosed herein provide for more balanced immobilization of a target material across the two opposed sequencing surfaces. In some examples, the same type of target material is immobilized across the two opposed sequencing surfaces. In other examples, two different target materials (having at least one different property) are respectively immobilized on the two opposed sequencing surfaces.

One example of the method disclosed herein utilizes a combination of fluids having different densities. One fluid density enables the target material (e.g., complexes, clustered solid supports) to migrate to and become immobilized at one of the sequencing surfaces, and the other fluid density enables the target material to migrate to and become immobilized at the other of the sequencing surfaces.

Another example of the method utilizes a combination of a fluid, a substantially uniform magnetic force, and a magnetically responsive target material (e.g., a solid support). In this example, the fluid is selected to have a density that is approximately the same as the magnetically responsive target material. In this fluid, some of the target material sinks (and becomes immobilized at one of the sequencing surfaces), while some other of the target material floats. When the substantially uniform magnetic force is applied to the other of the sequencing surfaces, the floating target material migrates to and becomes immobilized at the other of the sequencing surfaces.

Still another example of the method disclosed herein utilizes two different target materials having different densities. Both target materials are contained in the same fluid. The density of one of the target materials (with respect to the fluid) enables that target material (e.g., complexes, clustered solid supports) to migrate to and become immobilized at one of the sequencing surfaces, and the density of the other of the target materials (with respect to the fluid) enables that target material to migrate to and become immobilized at the other of the sequencing surfaces.

Yet another example of the method disclosed herein utilizes two different target materials having at least one different property, such as density, charge, magnetism, or combinations thereof. Exposure to at least one condition causes the different target materials to migrate to a respective one of the opposed sequencing surfaces.

Immobilization of the target material(s) (e.g., complexes, clustered solid supports) on both sequencing surfaces improves the overall utilization of the flow cell.

A more balanced distribution of the immobilized target material(s) across the two sequencing surfaces may lead to improved downstream metrics obtained using the flow cell. In one example, the more balanced distribution of the immobilized target material across the two sequencing surfaces may lead to improved sequencing metrics. In one example, the target material may include complexes, and when the complexes are more evenly distributed across the two sequencing surfaces of the flow cell, the library fragments released from the complexes also seed more evenly across the respective sequencing surfaces. This leads to the formation of individual clusters that are relatively localized with respect to the position of the complexes from which the clusters are formed. In another example, the target material may include clustered solid supports. When the clustered solid supports are more evenly distributed across the two sequencing surfaces of the flow cell, the clustered template strands are also more evenly distributed. During sequencing, individual clusters generate "spatial clouds" of fluorescence signals as nucleotides are incorporated into respective template strands of the clusters. The even distribution can improve the readability of the spatial clouds.

Moreover, loading both sequencing surfaces generates more area for generating these spatial clouds.

Definitions

Terms used herein will be understood to take on their ordinary meaning in the relevant art unless specified otherwise. Several terms used herein and their meanings are set forth below.

As used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, unrecited elements or method steps.

Reference throughout the specification to "one example," "another example," "an example," and so forth, means that a particular element (e.g., feature, structure, composition, configuration, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, these terms can refer to less than or equal to ±10% from a stated value, such as less than or equal to ±5% from a stated value, such as less than or equal to ±2% from a stated value, such as less than or equal to ±1% from a stated value, such as less than or equal to ±0.5% from a stated value, such as less than or equal to ±0.2% from a stated value, such as less than or equal to ±0.1% from a stated value, such as less than or equal to ±0.05% from a stated value.

Adapter. A linear oligonucleotide sequence that can be fused to a nucleic acid molecule, for example, by ligation or tagmentation. Suitable adapter lengths may range from about 10 nucleotides to about 100 nucleotides, or from about 12 nucleotides to about 60 nucleotides, or from about 15 nucleotides to about 50 nucleotides. The adapter may include any combination of nucleotides and/or nucleic acids. In some examples, the adapter can include a sequence that is complementary to at least a portion of a primer, for example, a primer including a universal nucleotide sequence (such as a P5 or P7 sequence). As an example, the adapter at one end of a fragment includes a sequence that is complementary to at least a portion of a first flow cell or solid support primer, and the adapter at the other end of the fragment includes a sequence that is identical to at least a portion of a second flow cell or solid support primer. The complementary adapter can hybridize to the first flow cell or solid support primer, and the identical adapter is a template for its complementary copy, which can hybridize to the second flow cell or solid support primer during clustering. In some examples, the adapter can include a sequencing primer sequence or sequencing binding site. Combinations of different adapters may be incorporated into a nucleic acid molecule, such as a DNA fragment.

Approximately Equivalent: At least approximately equivalent means that the density of one component (e.g., fluid) is within 0.08 g/cm$^3$ of the density of another component (e.g., a solid support). In some instances the densities of two components are equivalent.

Capture site or Chemical capture site: A portion of a flow cell surface having been modified with a chemical property that allows for localization of a target material (e.g., complexes, clustered solid supports, protein biomarkers, etc.). In an example, the capture site may include a chemical capture agent (i.e., a material, molecule or moiety that is capable of attaching, retaining, or binding to a target molecule (e.g., a complex, a clustered solid support, a protein biomarker, etc.). One example chemical capture agent includes a member of a receptor-ligand binding pair (e.g., avidin, streptavidin, biotin, lectin, carbohydrate, nucleic acid binding protein, epitope, antibody, etc.) that is capable of binding to the target material (or to a linking moiety attached to the target material). Yet another example of the chemical capture agent is a chemical reagent capable of forming an electrostatic interaction, a hydrogen bond, or a covalent bond (e.g., thiol-disulfide exchange, click chemistry, Diels-Alder, etc.) with the target material.

Complex: A carrier, such as a solid support, and sequencing-ready nucleic acid fragments attached to the carrier. The carrier may also include one member of a binding pair whose other member is part of the capture site.

Clustered solid support: A carrier, such as a solid support, having a plurality of amplified template strands attached thereto. The plurality of amplified template strands may be referred to as a "cluster."

Depositing: Any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

Depression: A discrete concave feature in a substrate or a patterned resin having a surface opening that is at least partially surrounded by interstitial region(s) of the substrate or the patterned resin. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

Each: When used in reference to a collection of items, each identifies an individual item in the collection, but does not necessarily refer to every item in the collection. Exceptions can occur if explicit disclosure or context clearly dictates otherwise.

External immobilizing agent: A gaseous, liquid or viscous medium that is not miscible with a complex that has been introduced to the flow cell. The gaseous external immobilizing agent may be used to create a droplet around a complex or sample. An example of a gaseous external immobilizing agent is air that is directed at a suitable flow rate through the flow cell. For example, air may be used to aspirate a fluid from the flow cell, which forms droplets of the liquid around complexes immobilized within the flow cell. The formed droplet acts as a diffusion barrier. The liquid or viscous medium is used to minimize diffusion of a sequencing library released from a complex. The external immobilizing agent can form a diffusion barrier, as the sequencing libraries or any other polynucleotide have little to no solvation in the external immobilizing agent. Example external immobilizing agents in liquid form include hydrophobic oils, such as mineral oil, silicone oil, perfluorinated oil, a fluorinated carbon oil (e.g., FC40), or a combination thereof. Example external immobilizing agents in viscous medium form include buffers containing polymers (e.g., polyethylene glycol, polyvinylpyrrolidone, etc.), dextran, sucrose, glycerol, and the like. In some examples, the viscous medium is a temperature responsive gel. The temperature responsive gel is non-viscous at non-seeding temperatures, and turns into a viscous medium at seeding temperatures. Examples of temperature responsive gels include poly(N-isopropylacrylamide) and polyethylene oxide-polypropylene oxide-polyethylene oxide (PEO-PPO-PEO)/laponite nanoparticle composites.

Flow Cell: A vessel having a chamber (e.g., a flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber can include one or more transparent surfaces allowing for the optical detection of arrays, optically labeled molecules, or the like.

Flow channel: An area defined between two bonded or otherwise attached components, which can selectively receive a liquid sample. In some examples, the flow channel may be defined between two patterned or non-patterned sequencing surfaces, and thus may be in fluid communication with one or more components of the sequencing surfaces.

Fragment: A portion or piece of genetic material (e.g., DNA, RNA, etc.). Contiguity preserved library fragments are smaller pieces of the longer nucleic acid sample that has been fragmented, where the contiguity information of the longer nucleic acid sample has been preserved in the fragments.

Nucleic acid molecule or sample: A polymeric form of nucleotides of any length, and may include ribonucleotides, deoxyribonucleotides, analogs thereof, or mixtures thereof. The term may refer to single stranded or double stranded polynucleotides.

A "template" nucleic acid molecule (or strand) may refer to a sequence that is to be analyzed. A cluster of template strands includes amplicons of a library fragment.

The nucleotides in a nucleic acid sample may include naturally occurring nucleic acids and functional analogs thereof. Examples of functional analogs are capable of hybridizing to a nucleic acid in a sequence specific fashion or capable of being used as a template for replication of a particular nucleotide sequence. Naturally occurring nucleotides generally have a backbone containing phosphodiester bonds. An analog structure can have an alternate backbone linkage including any of a variety known in the art. Naturally occurring nucleotides generally have a deoxyribose sugar (e.g., found in DNA) or a ribose sugar (e.g., found in RNA). An analog structure can have an alternate sugar moiety including any of a variety known in the art. Nucleotides can include native or non-native bases. A native DNA can include one or more of adenine, thymine, cytosine and/or guanine, and a native RNA can include one or more of adenine, uracil, cytosine and/or guanine. Any non-native base may be used, such as a locked nucleic acid (LNA) and a bridged nucleic acid (BNA).

Primer. A nucleic acid molecule that can hybridize to a target sequence, such as an adapter attached to a library fragment. As one example, an amplification primer can serve as a starting point for template amplification and cluster generation. As another example, a synthesized nucleic acid (template) strand may include a site to which a primer (e.g., a sequencing primer) can hybridize in order to prime synthesis of a new strand that is complementary to the synthesized nucleic acid strand. Any primer can include any combination of nucleotides or analogs thereof. In some examples, the primer is a single-stranded oligonucleotide or polynucleotide. The primer length can be any number of bases long and can include a variety of non-natural nucleotides. In an example, the sequencing primer is a short strand, ranging from 10 to 60 bases, or from 20 to 40 bases.

Sequencing-ready nucleic acid fragments: A portion of genetic material having adapters at the 3' and 5' ends. In the sequencing-ready nucleic acid fragment, each adapter includes a known universal sequence (e.g., which is complementary to or identical to at least a portion of a primer on a flow cell) and a sequencing primer sequence. Both of the adapters may also include an index (barcode or tag) sequence. In an example, one side (e.g., including a P5' or P5 sequence) may contain a bead index and the other side (including a P7 or P7' sequence) may contain a sample index. A sequencing-ready nucleic acid fragment may be bound to a solid support via insertion of transposons, where inserted DNA molecules are immobilized to the surface of a solid support (e.g., bead); or directly immobilized through a binding pair or other cleavable linker; or bound via hybridization, where complementary adapter sequences are present on the surface of the solid support.

Sequencing surface: A surface of a flow cell where sequencing can take place. In some examples, the sequencing surface includes a polymeric hydrogel having one or more types of amplification primers grafted thereto. In these examples, the sequencing surface may also include a capture site to immobilize complexes at or near the amplification primers. In other examples, the sequencing surface includes capture sites to immobilize clustered solid supports.

Solid support: A small body made of a rigid or semi-rigid material having a shape characterized, for example, as a sphere, oval, microsphere, or other recognized particle shape whether having regular or irregular dimensions. In some examples, the solid support can have a sequencing library attached thereto. In other examples, the solid support can have a cluster of template strands attached thereto.

Target Material: Any substance that is to be immobilized on a flow cell surface.

Transposome: A complex formed between an integration enzyme (e.g., an integrase or a transposase) and a nucleic acid including an integration recognition site (e.g., a transposase recognition site).

In the examples disclosed herein, target materials are introduced to a flow cell that includes two opposed sequencing surfaces. The target materials and flow cell will now be described, followed by different examples of the methods for immobilizing the target materials on each of the two opposed sequencing surfaces.

Target Materials

Figure 1B:
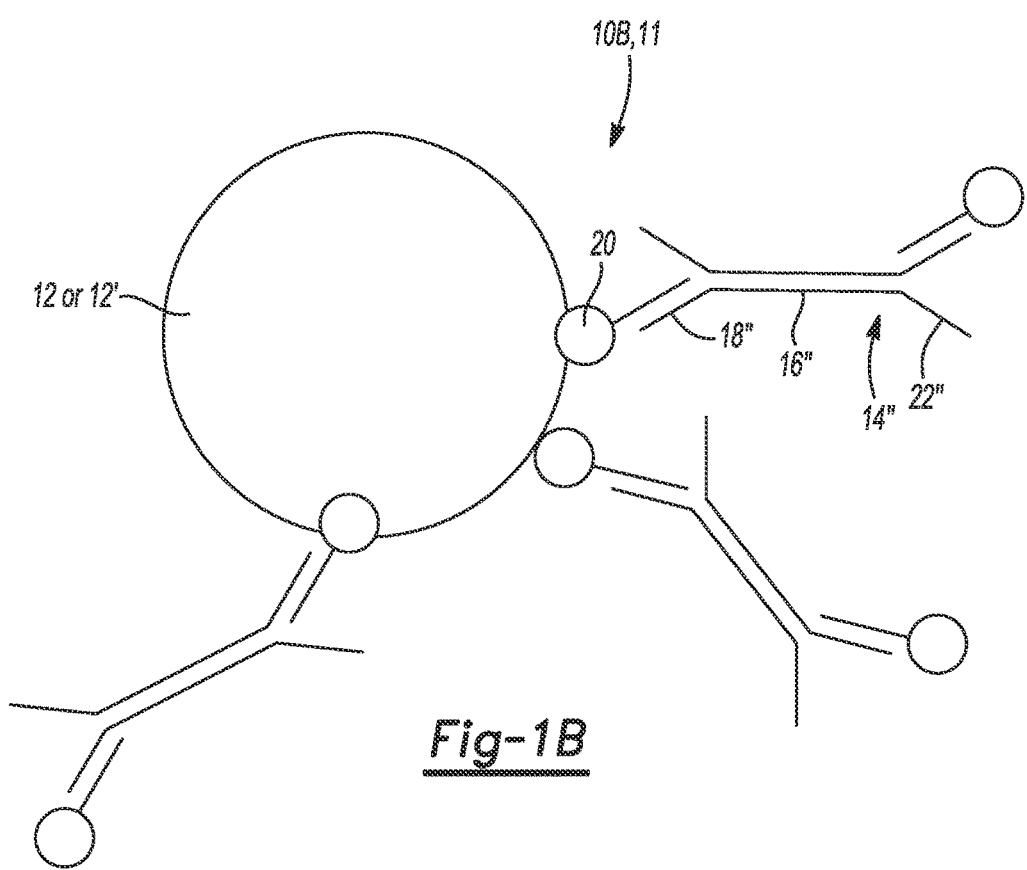
Figure 1C:
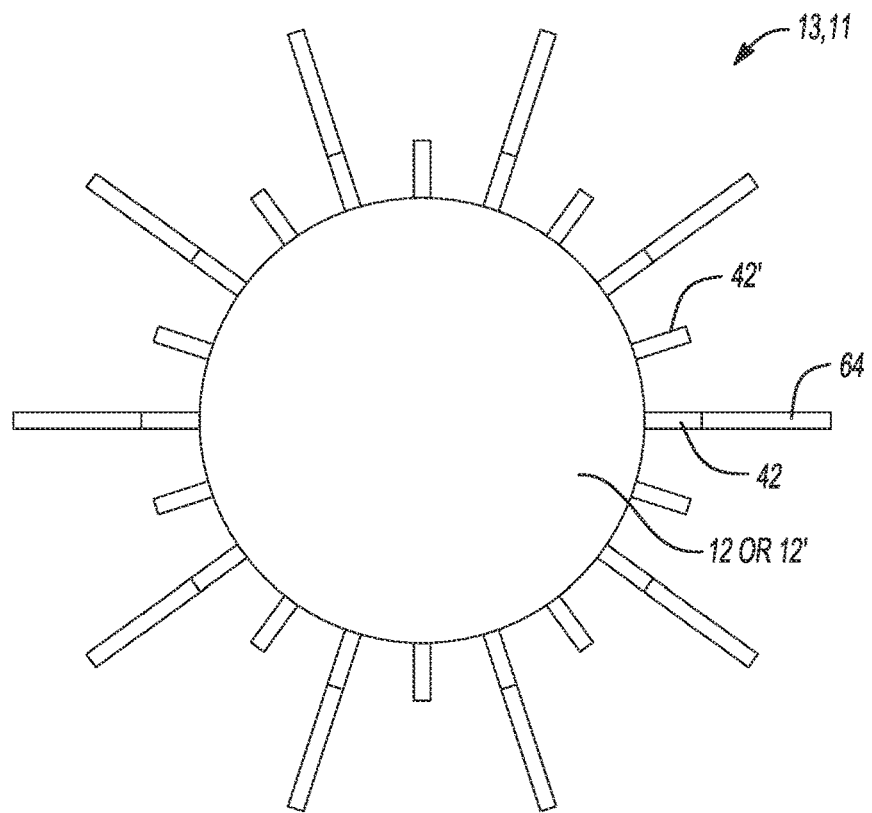

Example target materials 11 are shown in FIG. 1A through FIG. 1C. In the examples disclosed herein, any target material 11 that is to be immobilized on a surface of a flow cell may be utilized. As examples, the target material 11 may be a complex 10A, 10B as defined herein (see FIG. 1A and FIG. 1B), a clustered solid support 13 as defined herein (see FIG. 1C), other DNA libraries from a specific sample, cells, oligonucleotide conjugated proteins bound to solid supports, a protein biomarker, a microbiome, or the like. The following description provides some examples of the complexes 10A, 10B and of the clustered solid support 13.

Complexes

Some example complexes 10A and 10B are shown, respectively, in FIG. 1A and FIG. 1B. In the examples of the method disclosed herein, the complexes 10A, 10B include a solid support 12, 12' and sequencing-ready nucleic acid fragments 14, 14', 14" attached to the solid support 12, 12'.

In examples of the method that utilize the combination of fluids having different densities, or target materials 11 with different densities, or non-charged target materials 11, the solid support 12 may be, without limitation, hydrogels; glass (e.g., controlled pore glass beads); plastic, such as acrylic, polystyrene or a copolymer of styrene and another material, polypropylene, polyethylene, polybutylene, polyurethane or polytetrafluoroethylene (TEFLON® from The Chemours Co); polysaccharides or cross-linked polysaccharides such as agarose, SEPHAROSE® beads (cross-linked beaded form of agarose, available from Cytivia), or SEPHADEX® beads (cross-linked beaded form of dextran, available from Cytivia); nylon; nitrocellulose; resin; silica or silica-based materials including silicon and modified silicon; carbon-fiber; metal; inorganic glass; an optical fiber bundle; or a variety of other polymers. Some examples of the solid support 12 may have the form of solids beads, porous beads, or hollow beads.

In examples of the method that utilize the combination of the fluid and the magnetic force, the solid support 12' is a magnetically responsive material. A "magnetically responsive" material is responsive to a magnetic field. Examples of magnetically responsive solid supports include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$. One commercially available example includes DYNABEADS™ M-280 Streptavidin (superparamagnetic beads coated with streptavidin) from ThermoFisher Scientific. In some examples, the magnetically responsive material is embedded in the shell of a polymer bead. In other examples, the magnetically responsive material is in bead form and is coated with a passivating material, such as silicon oxide or silicon nitrite. In example methods utilizing two different target materials 11, one of the target materials 11 may include any of the magnetically responsive solid supports 12' disclosed herein.

In examples of the method that utilize an electric field for immobilization, the solid support 12 of the target material 11 may be positively charged or negatively charged. In these examples, any of the examples set forth for the solid support 12 may be used, and may be coated or functionalized to impart the desired charge. Either small molecules or polymers may be used to impart charge to the solid support 12. For example, any of the solid supports 12 (e.g., polystyrene, silica, etc.) may be functionalized with amines to render them positively charged. Any primary, secondary, or tertiary amine may be used. Examples of suitable amines include amino-silane, polylysine, or chitosan. For another example, any of the solid supports 12 (e.g., polystyrene, silica, SEPHADEX®, etc.) may be functionalized with carboxyl groups or sulfate groups to render them negatively charged. For still another example, any of the solid supports 12 (e.g., polystyrene, silica, SEPHADEX®, etc.) may be coated with polyglutamic acid to render them negatively charged.

While not shown in FIG. 1A and FIG. 1B, the solid support 12, 12' may be functionalized with one member of a binding pair. A "binding pair" refers to two agents (e.g., materials, molecules, moieties) that are capable of attaching to one another. In this example, the member on the solid support 12, 12' is a binding pair with another member that is located on the sequencing surface of the flow cell. In other examples, the solid support 12, 12' may be capable of being chemically conjugated to the sequencing surface of the flow cell.

Functionalization of the solid support 12, 12' may involve coating the solid support 12, 12' with the binding pair member, or forming a bond between the binding pair member and a functional group at the surface of the solid support 12, 12'. One example binding pair member includes a member of a receptor-ligand binding pair (e.g., avidin, streptavidin, biotin, lectin, carbohydrate, nucleic acid binding protein, epitope, antibody, etc.) that is capable of binding to the other binding pair member that is located on the sequencing surface of the flow cell. The binding pair members may also be chemical reagents that are capable of forming an electrostatic interaction, a hydrogen bond, or a covalent bond (e.g., thiol-disulfide exchange, click chemistry, Diels-Alder, etc.). Any form of chemical coupling may also attach the solid support 12, 12' to the sequencing surface of the flow cell. In many instances, a reversible or cleavable interaction is desirable so that the solid support 12, 12' may be removed prior to sequencing.

In examples of the complex 10A, 10B, the sequencing-ready nucleic acid fragments 14, 14', 14" are attached to the solid support 12, 12'. Each sequencing-ready nucleic acid fragment 14, 14', 14" includes a portion (e.g., fragment 16, 16', 16") of a longer piece of genetic material that has adapters (e.g., 18, 18', 18", 22, 22', 22") at the 3' and 5' ends. The sequencing-ready fragments 14, 14', 14" may be prepared using any library preparation technique that fragments a longer piece of genetic material and incorporates the desired adapters 18, 18', 18", 22, 22', 22" to the ends of the fragments 16, 16', 16". Some suitable library preparation techniques are described in reference to FIG. 1A and FIG. 1B. It is to be understood, however, that other library preparation techniques may also be used.

FIG. 1A depicts an example of a complex 10A including sequencing-ready nucleic acid fragments 14, 14' which include fragments 16, 16' from the larger nucleic acid sample, whose contiguity is preserved on the solid support 12, 12'. An example method for making the complex 10A is described herein, but it is to be understood that other methods may be used as long as sequencing-ready nucleic acid fragments 14, 14' are attached to the solid support 12, 12'.

In one example method to form the complex 10A shown in FIG. 1A, an adapter sequence 18, 18' is bound to the solid support 12, 12' through one member 20 of a binding pair. In an example, this adapter sequence 18, 18' may include a first sequencing primer sequence (e.g., a read 1 sequencing primer sequence) and a first sequence (P5') that is complementary to at least a portion of one of the amplification primers (e.g., P5) on the flow cell (shown in FIG. 2A, FIG. 2B and FIG. 2C). The adapter sequence 18, 18' may also include an index or barcode sequence. The adapter sequence 18, 18' is bound to the one member 20 (e.g., biotin) of the binding pair so that it can be bound to the surface of the solid support 12, 12', which includes the other member (e.g., avidin, streptavidin, etc.) of the binding pair. In this example, the member of the binding pair on the solid support 12, 12' may be multi-functional in that it can i) bind to the member 20 used to attach the sequencing-ready nucleic acid fragments 14, 14' and ii) bind to the sequencing surface of the flow cell. In other examples, the solid support 12, 12' may be functionalized with two different binding pair members, e.g., i) one of which can bind to the member 20 used to attach the sequencing-ready nucleic acid fragments 14, 14' and ii) another of which can bind to the sequencing surface of the flow cell.

In this example, a transposome complex (not shown) may also be bound to the solid support 12, 12' at the outset of the library preparation method. Prior to loading the transposome complex on the solid support 12, 12', a partial Y-adapter may be mixed with a transposase enzyme (e.g., two Tn5 molecules) to form a transposome complex. The partial Y-adapter may include two mosaic end sequences that are hybridized to each other. One of the mosaic end sequences is referred to as a free mosaic end sequence because it has two free ends, e.g., one that is able to attach to the adapter 18, 18' and another that is able to attach to fragmented DNA strands 16, 16' during tagmentation. The other of the mosaic end sequences may be attached to another adapter (e.g., 22, 22'), which includes a second sequencing primer sequence (e.g., a read 2 sequencing primer sequence) and a second sequence (P7) that is identical to the at least a portion of another of the amplification primers (P7) on the flow cell. During amplification, the identical sequence enables the formation of a copy that is complementary to at least a portion of the other of the amplification primers (P7) on the flow cell. The adapter sequences 22, 22' are not attached to the fragmented DNA strands 16, 16' during tagmentation.

Loading the transposome complex on the solid support 12, 12' may involve mixing the transposome complex with the solid support 12, 12', and exposing the mixture to suitable conditions for ligating one of free ends of the free mosaic end to the 3'-end of the adapter sequence 18, 18'. Individual transposome complexes may be attached to each of the adapter sequences 18, 18' on the solid support 12, 12'.

In this example method to form the complex 10A, a tagmentation process may then be performed. A fluid (e.g., a tagmentation buffer) including the longer nucleic acid sample (e.g., DNA) may be added to the solid support 12, 12' having the adapter sequence 18, 18' and the transposome complexes bound thereto. As the sample contacts the transposome complexes, the longer nucleic acid sample is tagmented. The longer nucleic acid sample is fragmented into fragments 16, 16', and each is tagged, at its 5' end, to the partial Y-adapter (e.g., through ligation of the other free end of the free mosaic end sequence). Successive tagmentation of the longer nucleic acid sample results in a plurality of bridged molecules between the transposome complexes. The bridged molecules wrap around the solid support 12, 12'. The transposome complexes maintain the contiguity of the longer nucleic acid sample as bridged molecules.

The transposase enzyme may then be removed via sodium dodecyl sulfate (SDS) treatment or heat or proteinase K digestion. Removal of the transposase enzymes leaves the contiguity preserved fragments 16, 16' attached to the solid support 12, 12'.

To complete the sequencing ready fragments 14, 14', further extension and ligation is undertaken to ensure sample fragments 16, 16' are attached to sequences 22 and 22'. The resulting complex 10A is shown in FIG. 1A.

Each sequencing-ready nucleic acid fragment 14, 14' includes a contiguity preserved library fragment 16, 16' having respective adapter sequences 18 and 22 or 18' and 22' attached at either end. The adapter sequences 18, 18' are those initially bound to the solid support 12, 12', and include the first sequencing primer sequence and the first sequence complementary to one of the flow cell primers. The adapter sequences 18, 18' are attached to the one member 20 of a binding pair. The adapter sequences 22, 22' are from the partial Y-adapter, and include the second sequence identical to another flow cell primer and the second sequencing primer sequence. Because each sequencing-ready nucleic acid fragment 14, 14' includes suitable adapters for amplification (e.g., bridge amplification) and sequencing, PCR amplification is not performed. These fragments 14, 14' are thus sequencing-ready. Moreover, because the contiguity preserved library fragments 16, 16' are from the same longer nucleic acid sample, the contiguity of the original sample is preserved and the library fragments 14, 14' may be suitable for linked long read applications.

FIG. 1B illustrates another complex 10B that includes a solid support 12, 12' and sequencing-ready nucleic acid fragments 14" attached to the solid support 12, 12'. In one example, a PCR-free nucleotide library is created in a tube, and then the library is hybridized on the solid support 12, 12' in the tube. In the example shown in FIG. 1B, adapters 18", 22" are added to the library fragments 16" in the tube, primers having one member 20 of a binding pair are hybridized to the adapters 18" in the tube, and then the sequencing-ready nucleic acid fragments 14" are bound to the solid support 12, 12' through the member 20 of a binding pair. In another example, the solid support 12, 12' may have primers attached thereto via a binding pair (e.g., avidin on the support 12, 12' and biotin attached to the primer). These primers hybridize to adapters 18" attached to the library fragments 16" (and thus the primer and binding pair member are at one end of the fragments and not at the other). In still other example, extension may be performed using a strand displacing enzyme. This will result in an entirely double stranded library (e.g., no fork or Y-adapter, as shown in FIG. 1B).

As mentioned, other library preparation techniques may also be used. For example, ligation based library preparation techniques may be used where the complementary adapter sequence is immobilized on the flow cell. For another example, mRNA may be immobilized to the solid support 12, 12' via polyA tail hybridization.

Clustered Solid Supports

An example clustered solid support 13 is shown in FIG. 1C. The clustered solid support 13 includes a solid support 12, 12' and template strands 64 attached to the solid support 12, 12' through a primer 42 or 42'.

Any example of the solid support 12, 12' may be used as the core of the clustered solid support 13. The type of solid support 12, 12', and its property/properties (e.g., density, charge, magnetism, etc.), may depend upon the immobilization method that is to be used.

While not shown in FIG. 1C and similar to the complexes 10A and 10B shown in FIG. 1A and FIG. 1B, the solid support 12, 12' may be functionalized with one member of a binding pair for attachment to a capture site of a flow cell.

As shown in FIG. 1C, this example of the solid support 12, 12' is functionalized with primers 42, 42'. The primers 42, 42' may be amplification primers 42, 42' that can be immobilized to the solid support 12, 12' by single point covalent attachment or a strong non-covalent interaction at or near the 5' end of the primers 42, 42'. The attachment leaves i) an adapter-specific portion of the primers 42, 42' free to anneal to its cognate sequencing-ready nucleic acid fragment and ii) the 3' hydroxyl group free for primer extension. At or near the 5' end, the primer 42, 42' includes a chemically modifiable functional group that is capable of covalent attachment or strong non-covalent interaction. Examples of chemically modifiable functional groups include thiol, azido, alkyne, amino, biotin, etc.

Specific examples of suitable primers 42, 42' include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms. Both P5 and P7 primers may be grafted to each of the solid supports 12, 12'.

In an example, grafting of the primers 42, 42' to the solid support 12, 12' may involve dunk coating, which involves immersing the solid support 12, 12' in a primer solution or mixture, which may include the primers 42, 42', water, a buffer, and a catalyst. Other grafting techniques may involve spray coating, puddle dispensing, or another suitable method that will attach the primer(s) 42, 42' to the solid support 12, 12'. With any of the grafting methods, the primers 42, 42' react with reactive groups of the solid support 12, 12'.

During grafting, the chemically modifiable functional group of the primer 42, 42' reacts or interacts with the reactive groups of the solid support 12, 12'. The following are examples of reactions or interactions that may take place during grafting: reacting an azido (e.g., succinimidyl (NHS) ester) terminated primer with a hydrazine on the surface of the solid support 12, 12', or reacting an alkyne terminated primer with an azide on the surface of the solid support 12, 12', or reacting an amino terminated primer to an activated carboxylate group or NHS ester on the surface of the solid support 12, 12', or reacting a thiol terminated primer with an alkylating reactant (e.g., iodoacetamine or maleimide) on the surface of the solid support 12, 12', or reacting a phosphoramidite terminated primer with a thioether on the surface of the solid support 12, 12', or interacting a biotin-modified primer with streptavidin on the surface of the solid support 12, 12'. Some nucleic acid primers 42, 42' can be captured onto silica beads in the presence of a chaotropic agent (KI, NI, or NaSCN). As one specific example, a dibenzocyclooctyne (DBCO, which includes an alkyne) terminated primer may be used for copper free click grafting.

To generate the template strands 64 on the solid support 12, 12', library templates may first be prepared from any nucleic acid sample (e.g., a DNA sample or an RNA sample). When an RNA sample is used, it is first converted to a complementary deoxyribonucleic acid (cDNA) sample. This may be done using reverse transcription, which utilizes a reverse transcriptase enzyme. In some examples, a kit for reverse transcription and second strand synthesis is used. In these examples, the high capacity cDNA reverse transcription kit, from ThermoFisher Scientific, may be used. In other examples, a kit for reverse transcription and template switch (for the second strand) is used. In these examples, the template switching RT enzyme mix, from New England Biolabs, may be used.

The DNA or cDNA sample may then be fragmented into single-stranded, similarly sized (e.g., <1000 bp) fragments. During preparation, adapters may be added to the ends of these fragments. Through reduced cycle amplification, different motifs may be introduced in the adapters, such as sequencing binding sites, indices, and regions that are complementary or identical to the primers 42, 42' on the solid support 12, 12'. The final library templates include the DNA or cDNA fragment and adapters at both ends. In some examples, the fragments from a single nucleic acid sample have the same adapters added thereto.

A plurality of library templates may be introduced to a plurality of the solid supports 12, 12'. A library template hybridizes to one of two types of primers 42, 42' immobilized on a respective solid support 12, 12'. Cluster generation may then be performed. In one example of cluster generation, the library template on the solid support 12, 12' is copied from the hybridized primer by 3' extension using a high-fidelity DNA polymerase. The original library template is denatured, leaving the copy (e.g., template strand 64) immobilized on the solid support 12, 12', e.g., through the primer 42 as shown in FIG. 1C. Isothermal bridge amplification or some other form of amplification may be used to amplify the immobilized copies. For example, the copied template loops over to hybridize to an adjacent, complementary primer (e.g., primer 42'), and a polymerase copies the copied template to form a double stranded bridge, which is denatured to form two single stranded strands. These two strands loop over and hybridize to adjacent, complementary primers 42, 42' and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. Clustering results in the formation of several template polynucleotide strands 64 on the solid support 12, 12'. This example of clustering is bridge amplification, and is one example of the amplification that may be performed.

Flow Cell

Figure 2B:
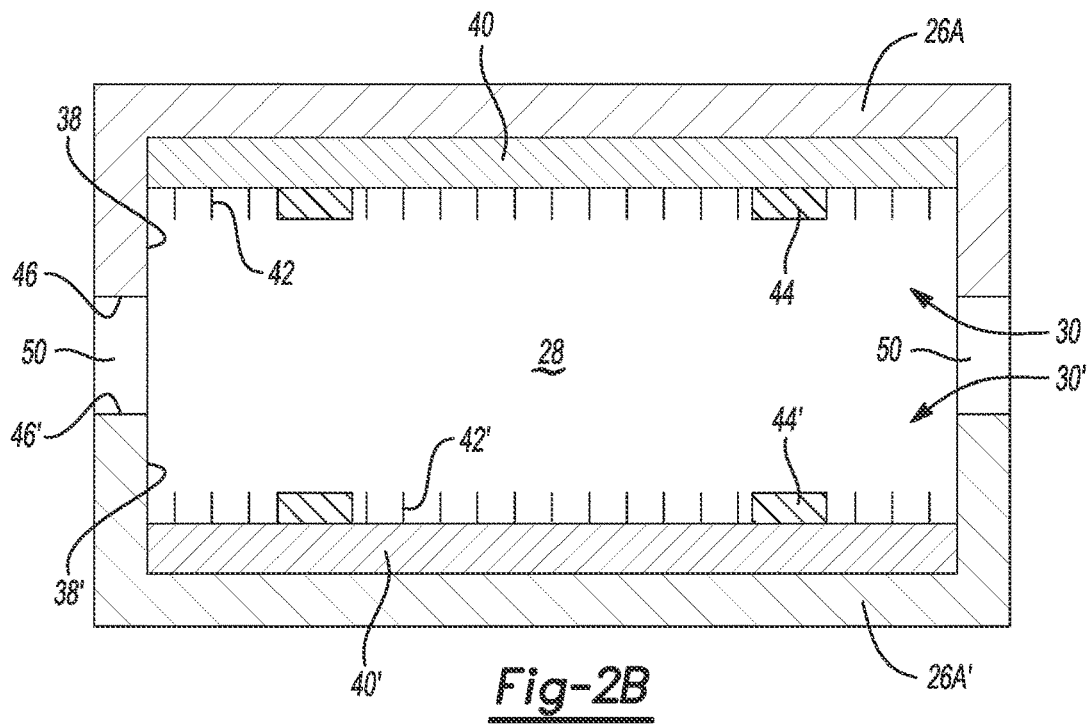
FIG. 2B is an enlarged, cross-sectional view, taken along the 2B-2B line of FIG. 2A, of an example of a flow channel and non-patterned sequencing surfaces.
Figure 2A:
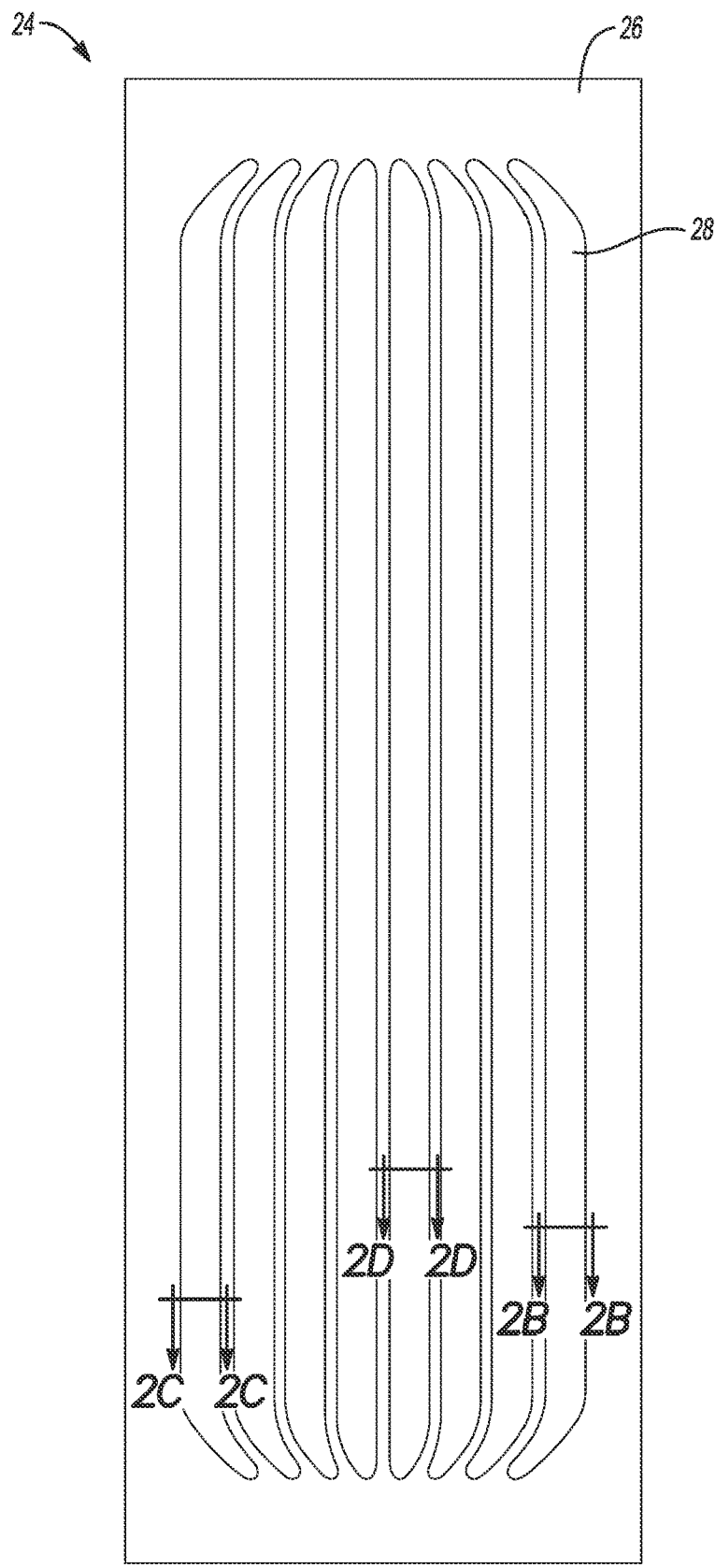
FIG. 2A is a top view of an example of a flow cell.
Figure 2C:
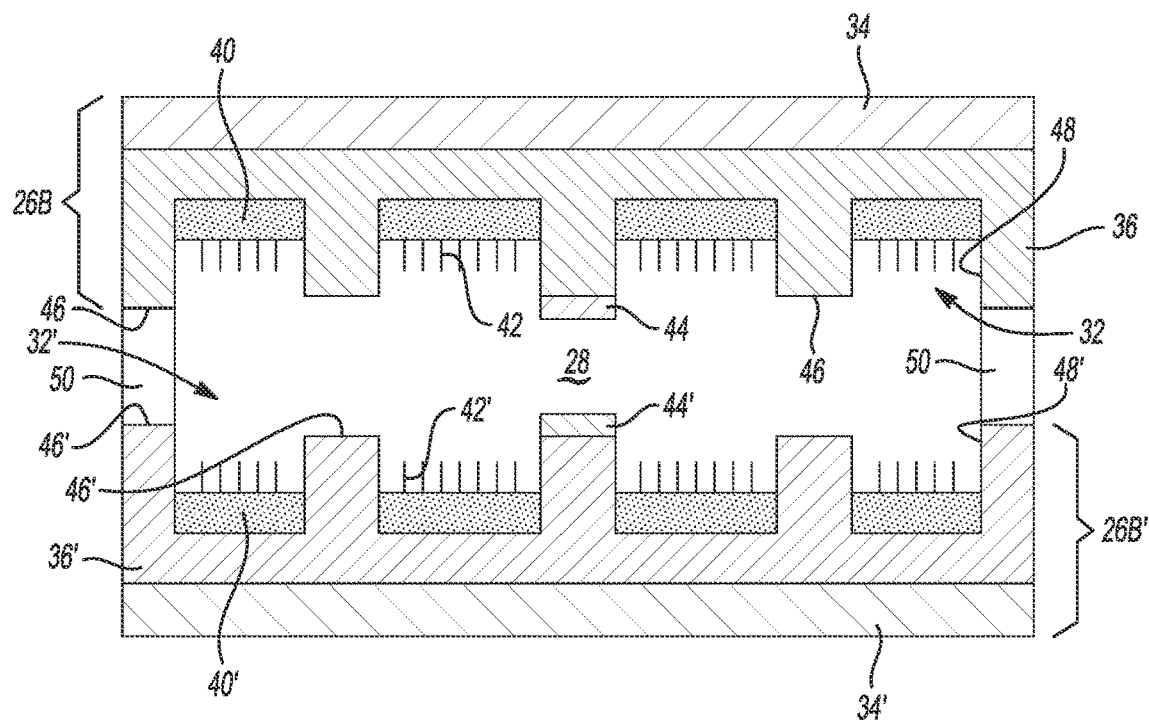
FIG. 2C is an enlarged, cross-sectional view, taken along the 2C-2C line of FIG. 2A, of an example of a flow channel and patterned sequencing surfaces.
Figure 2D:
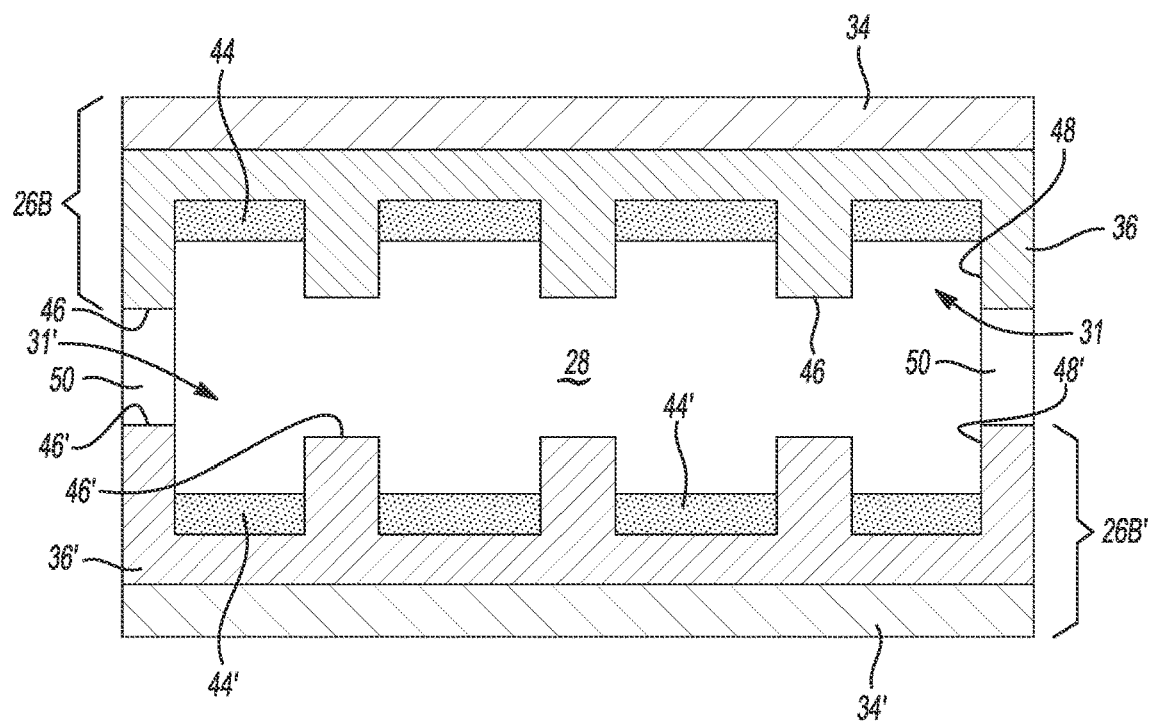
FIG. 2D is an enlarged, cross-sectional view, taken along the 2D-2D line of FIG. 2A, of another example of a flow channel and patterned sequencing surfaces.

A top view of an example of the flow cell 24 is shown in FIG. 2A. As mentioned herein, the flow cell 24 includes two sequencing opposed sequencing surfaces. An example of non-patterned sequencing surfaces 30, 30' are shown in FIG. 2B, an example of patterned sequencing surfaces 32, 32' are shown in FIG. 2C, and another example of patterned sequencing surfaces 31, 31' are shown in FIG. 2D. The non-patterned sequencing surfaces 30, 30' and patterned sequencing surfaces 32, 32' include primers 42, 42', and thus may be utilized with target materials 11 that introduce library fragments that are to be amplified on the flow cell 24. Other sequencing surfaces, such as patterned sequencing surfaces 31, 31', do not include primers 42, 42', and thus may be utilized with clustered solid supports 13.

Each sequencing surface 30, 30' or 32, 32' or 31, 31' is supported by a substrate (generally shown as 26 in FIG. 2A), and a flow channel (generally shown as 28 in FIG. 2A) is defined between the sequencing surfaces 30, 30' or 32, 32' or 31, 31'.

The substrate 26 may be a single layer/material. Examples of the single layer substrate are shown at reference numeral 26A and 26A' in FIG. 2B. Examples of suitable single layer substrates 26A, 26A' include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HfO_2$), carbon, metals, inorganic glasses, or the like.

The substrate 26 may also be a multi-layered structure. Examples of the multi-layered substrate are shown at reference numeral 26B and 26B' in FIG. 2C and in FIG. 2D. Some examples of the multi-layered structure 26B, 26B' include glass or silicon, with a coating layer of tantalum oxide or another ceramic oxide at the surface. With specific reference to FIG. 2C and FIG. 2D, other examples of the multi-layered structure 26B, 26B' include an underlying support 34, 34' having a patterned resin 36, 36' thereon. Still other examples of the multi-layered substrate 26B, 26B' may include a silicon-on-insulator (SOI) substrate.

In an example, the substrate 26 (whether single or multi-layered) may have a diameter ranging from about 2 mm to about 300 mm, or a rectangular sheet or panel having its largest dimension up to about 10 feet (~3 meters). In an example, the substrate 26 is a wafer having a diameter ranging from about 200 mm to about 300 mm. In another example, the substrate 26 is a die having a width ranging from about 0.1 mm to about 10 mm. While example dimensions have been provided, it is to be understood that a substrate 26 with any suitable dimensions may be used. For another example, a panel may be used that is a rectangular support, which has a greater surface area than a 300 mm round wafer.

In the example shown in FIG. 2A, the flow cell 24 includes flow channels 28. While several flow channels 28 are shown, it is to be understood that any number of channels 28 may be included in the flow cell 24 (e.g., a single channel 28, four channels 28, etc.). In the examples disclosed herein, each flow channel 28 is an area defined between two sequencing surfaces (e.g., 30 and 30' or 32 and 32' or 31 and 31') and by two attached substrates (e.g., 26A and 26A' or 26B and 26B'). The fluids described herein can be introduced into and removed from the flow channel(s) 28 via inlet(s) and outlet(s), respectively. Each flow channel 28 may be isolated from each other flow channel 28 in a flow cell 24 so that fluid introduced into any particular flow channel 28 does not flow into any adjacent flow channel 28.

A portion of the flow channel 28 may be defined in the substrate 26 using any suitable technique that depends, in part, upon the material(s) of the substrate 26. In one example, a portion of the flow channel 28 is etched into a glass substrate 26. In another example, a portion of the flow channel 28 may be patterned into a resin 36, 36' of a multi-layered substrate 26B, 26B' using photolithography, nanoimprint lithography, etc. In still another example, a separate material (e.g., material 50 in FIG. 2B and FIG. 2C and FIG. 2D) may be applied to the substrate 26 so that the separate material defines at least a portion of the walls of the flow channel 28.

In an example, the flow channel 28 has a rectangular configuration. The length and width of the flow channel 28 may be smaller, respectively, than the length and width of the substrate 26 so that portion of the substrate surface surrounding the flow channel 28 is available for attachment to another substrate 26. In some instances, the width of each flow channel 28 can be at least about 1 mm, at least about 2.5 mm, at least about 5 mm, at least about 7 mm, at least about 10 mm, or more. In some instances, the length of each flow channel 28 can be at least about 10 mm, at least about 25 mm, at least about 50 mm, at least about 100 mm, or more. The width and/or length of each flow channel 28 can be greater than, less than or between the values specified above. In another example, the flow channel 28 is square (e.g., 10 mm×10 mm).

The depth of each flow channel 28 can be as small as a few monolayers thick, for example, when microcontact, aerosol, or inkjet printing is used to deposit a separate material (e.g., material 50) that defines the flow channel walls. For other examples, the depth of each flow channel 28 can be about 1 µm, about 10 µm, about 50 µm, about 100 µm, or more. In an example, the depth may range from about 10 µm to about 100 µm. In another example, the depth is about 5 µm or less. It is to be understood that the depth of each flow channel 28 be greater than, less than or between the values specified above. The depth of the flow channel 28 may also vary along the length and width of the flow cell 24, e.g., when a patterned sequencing surface 32, 32' or 31, 31' is used.

FIG. 2B illustrates a cross-sectional view of the flow cell 24 including non-patterned opposed sequencing surfaces 30, 30'. In an example, each of these surfaces 30, 30' may be prepared on the substrate 26A, 26A', and then the substrates 26A, 26A' may be attached to one another to form an example of the flow cell 24. Any suitable bonding material 50, such as an adhesive, a radiation-absorbing material that aids in bonding, etc., may be used to bond the substrates 26A, 26B together.

In the example shown in FIG. 2B, a portion of the flow channel 28 is defined in each of the single layer substrates 26A, 26A'. For example, each substrate 26A, 26A' may have a concave region 38, 38' defined therein where the components of the sequencing surface 30, 30' may be introduced. It is to be understood that any space within the concave region 38, 38' not occupied by the components of the sequencing surface 30, 30' may be considered to be part of the flow channel 28.

The sequencing surfaces 30, 30' include a polymeric hydrogel 40, 40', amplification primers 42, 42' attached to the polymeric hydrogel 40, 40', and chemical capture sites 44, 44'.

An example of the polymeric hydrogel 40, 40' includes an acrylamide copolymer, such as poly(N-(5-azidoacetamidyl-pentyl)acrylamide-co-acrylamide, PAZAM. PAZAM and some other forms of the acrylamide copolymer are represented by the following structure (I):

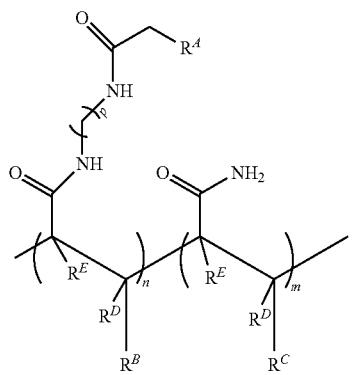

wherein:
- $R^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;
- $R^B$ is H or optionally substituted alkyl;
- $R^C$, $R^D$, and $R^E$ are each independently selected from the group consisting of H and optionally substituted alkyl;
- each of the —$(CH_2)_p$— can be optionally substituted;
- p is an integer in the range of 1 to 50;
- n is an integer in the range of 1 to 50,000; and
- m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of PAZAM and other forms of the acrylamide copolymer may range from about 5 kDa to about 1500 kDa or from about 10 kDa to about 1000 kDa, or may be, in a specific example, about 312 kDa.

In some examples, PAZAM and other forms of the acrylamide copolymer are linear polymers. In some other examples, PAZAM and other forms of the acrylamide copolymer are a lightly cross-linked polymers.

In other examples, the polymeric hydrogel 40, 40' may be a variation of the structure (I). In one example, the acrylamide unit may be replaced with N,N-dimethylacrylamide

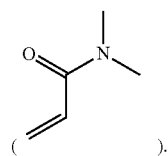

In this example, the acrylamide unit in structure (I) may be replaced with

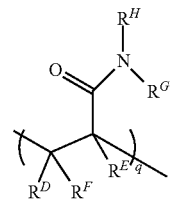

where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

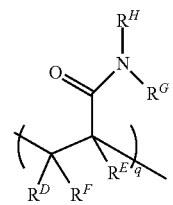

in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

As another example of the polymeric hydrogel 40, 40', the recurring "n" feature in structure (I) may be replaced with a monomer including a heterocyclic azido group having structure (II):

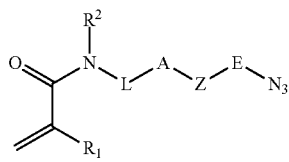

wherein $R^1$ is H or a C1-C6 alkyl; $R_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 ring members present as a single cyclic structure or a fused structure. Some specific examples of Z include pyrrolidinyl, pyridinyl, or pyrimidinyl.

As still another example, the polymeric hydrogel 40, 40' may include a recurring unit of each of structure (III) and (IV):

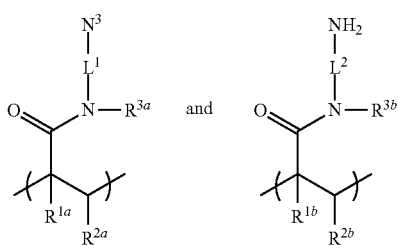

wherein each of $R_{1a}$, $R^{2a}$, $R^{1b}$ and $R^{2b}$ is independently selected from hydrogen, an optionally substituted alkyl or optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

It is to be understood that other molecules may be used to form the polymeric hydrogel 40, 40', as long as they are functionalized to graft oligonucleotide primers 42, 42' thereto. Other examples of suitable polymer layers include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymeric hydrogels 42 include mixed copolymers of acrylamides and acrylates. A variety of polymer architectures containing acrylic monomers (e.g., acrylamides, acrylates etc.) may be utilized in the examples disclosed herein, such as branched polymers, including star polymers, star-shaped or star-block polymers, dendrimers, and the like. For example, the monomers (e.g., acrylamide, etc.) may be incorporated, either randomly or in block, into the branches (arms) of a star-shaped polymer.

To introduce the polymeric hydrogel 40, 40' into the concave regions 38, 38', a mixture of the polymeric hydrogel 40, 40' may be generated and then applied to the respective substrates 26A, 26A' (having the concave regions 38, 38' defined therein). In one example, the polymeric hydrogel 40, 40' may be present in a mixture (e.g., with water or with ethanol and water). The mixture may then be applied to the respective substrate surfaces (including in the concave regions 38, 38') using spin coating, or dipping or dip coating, or flow of the material under positive or negative pressure, or another suitable technique. These types of techniques blanketly deposit the polymeric hydrogel 40, 40' on the substrate respective substrates 26A, 26A' (e.g., in the concave regions 38, 38' and on interstitial regions 46, 46' adjacent thereto). Other selective deposition techniques (e.g. involving a mask, controlled printing techniques, etc.) may be used to specifically deposit the polymeric hydrogel in the concave regions 38, 38' and not on the interstitial regions 46, 46'.

In some examples, the substrate surface (including the concave regions 38, 38') may be activated, and then the mixture (including the polymeric hydrogel 40, 40' may be applied thereto. In one example, a silane or silane derivative (e.g., norbornene silane) may be deposited on the substrate surface using vapor deposition, spin coating, or other deposition methods. In another example, the substrate surface may be exposed to plasma ashing to generate surface-activating agent(s) (e.g., —OH groups) that can adhere to the polymeric hydrogel 40, 40'.

Depending upon the chemistry of the polymeric hydrogel 40, 40', the applied mixture may be exposed to a curing process. In an example, curing may take place at a temperature ranging from room temperature (e.g., about 25° C.) to about 95° C. for a time ranging from about 1 millisecond to about several days.

Polishing may then be performed in order to remove the polymeric hydrogel 40, 40' from the interstitial regions 46, 46' at the perimeter of the concave regions 38, 38', while leaving the polymeric hydrogel 40, 40' on the surface in the concave regions 38, 38' at least substantially intact.

The sequencing surfaces 30, 30' also include amplification primers 42, 42' attached to the polymeric hydrogel 40, 40'.

A grafting process may be performed to graft the amplification primers 42, 42' to the polymeric hydrogel 40, 40' in the concave regions 38, 38'. In an example, the amplification primers 42, 42' can be immobilized to the polymeric hydrogel 40, 40' by single point covalent attachment or strong non-covalent interaction at or near the 5' end of the primers 42, 42'. The attachment leaves i) an adapter-specific portion of the primers 42, 42' free to anneal to its cognate sequencing-ready nucleic acid fragment and ii) the 3' hydroxyl group free for primer extension. Any suitable covalent attachment or strong non-covalent interaction may be used for this purpose. Examples of terminated primers that may be used include alkyne terminated primers (e.g., which may attach to an azide surface moiety of the polymeric hydrogel 40, 40'), or azide terminated primers (e.g., which may attach to an alkyne surface moiety of the polymeric hydrogel 40, 40'), or any of the other terminated primers described in reference to the clustered solid support 13.

Specific examples of suitable primers 42, 42' include P5 and P7 primers. Both P5 and P7 primers may be grafted to each of the polymeric hydrogels 40, 40'.

In an example, grafting may involve flow through deposition (e.g., using a temporarily bound lid), dunk coating, spray coating, puddle dispensing, or by another suitable method that will attach the primer(s) 42, 42' to the polymeric hydrogel 40, 40'. Each of these example techniques may utilize a primer solution or mixture, which may include the primer(s) 42, 42', water, a buffer, and a catalyst. With any of the grafting methods, the primers 42, 42' react with reactive groups of the polymeric hydrogel 40, 40' in the concave region 38, 38' and have no affinity for the surrounding substrate 26A, 26A'. As such, the primers 42, 42' selectively graft to the polymeric hydrogel 40, 40'.

In the example shown in FIG. 2B, the chemical capture site 44, 44' includes a chemical capture agent that is attached to or applied on at least a portion of the polymeric hydrogel 40, 40'. Any examples of the chemical capture agent disclosed herein may be used. For example, the chemical capture agent may be a member of a binding pair, where the other member of the binding pair is attached to the solid support 12, 12'.

In some examples, free functional groups (e.g., those not attached to primers 42, 42') of the polymeric hydrogel 40, 40' may be functionalized with the chemical capture agent so that several chemical capture sites 44, 44' are formed across the surface of the polymeric hydrogel 40, 40'. In an example, alkyne-PEG-biotin linkers or alkyne-biotin free azide groups may be covalently attached to free azides on the polymeric hydrogel 40, 40' using click chemistry. In another example, primers that are complementary to the amplification primers 42, 42' may have the chemical capture agent attached thereto. These complementary primers may be hybridized to some of the amplification primers 42, 42' to form the chemical capture site 44, 44'.

In another example, the chemical capture agent may be deposited in a desirable location using microcontact printing, aerosol printing, etc. to form the chemical capture site(s) 44, 44'. In still another example, a mask (e.g., a photoresist) may be used to define the space/location where the chemical capture agent will be deposited, and thus where the chemical capture site 44, 44' will be formed. The chemical capture agent may then be deposited, and the mask removed (e.g., via lift-off, dissolution, or another suitable technique). In this example, the chemical capture site 44, 44' may include a monolayer or thin layer of the chemical capture agent.

FIG. 2C illustrates a cross-sectional view of the flow cell 24 including patterned opposed sequencing surfaces 32, 32'. In an example, each of these surfaces 32, 32' may be prepared on the substrate 26B, 26B', and then the substrates 26B, 26B' may be attached to one another (e.g., via material 50) to form an example of the flow cell 24.

In the example shown in FIG. 2C, the flow cell 24 includes the multi-layer substrate 26B, 26B', each of which includes the support 34, 34' and the patterned material 36, 36' positioned on the support 34, 34'. The patterned material 36, 36' defines depressions 48, 48' separated by interstitial regions 46, 46'.

In the example shown in FIG. 2C, the patterned material 36, 36' is respectively positioned on the support 34, 34'. It is to be understood that any material that can be selectively deposited, or deposited and patterned to form the depressions 48, 48' and the interstitial regions 46, 46' may be used for the patterned material 36, 36'.

As one example, an inorganic oxide may be selectively applied to the support 34, 34' via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example, a resin may be applied to the support 34, 34' and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane resin (POSS)-based resin, a non-POSS epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (commercially available as POSS® from Hybrid Plastics) refers to a chemical composition that is a hybrid intermediate (e.g., $RSiO_{1.5}$) between that of silica ($SiO_2$) and silicone ($R_2SiO$). An example of polyhedral oligomeric silsesquioxane can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for polyhedral oligomeric silsesquioxane include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units. The polyhedral structure may be a $T_8$ structure, such as:

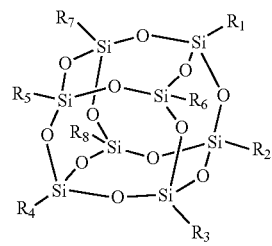

and represented by:

$T_8$

This monomeric unit typically has eight arms of functional groups $R_1$ through $R_8$.

The monomeric unit may have a cage structure with 10 silicon atoms and 10 R groups, referred to as $T_{10}$, such as:

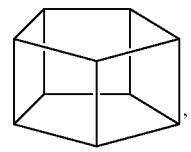

$T_{10}$ or may have a cage structure with 12 silicon atoms and 12 R groups, referred to as $T_{12}$, such as:

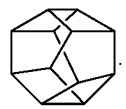

$T_{12}$

The polyhedral oligomeric silsesquioxane-based material may alternatively include $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein.

In some of the polyhedral oligomeric silsesquioxane examples disclosed herein, at least one of $R_1$ through $R_8$ or $R_{10}$ or $R_{12}$ comprises an epoxy. $R_1$ through $R_8$ or $R_{10}$ or $R_{12}$ may or may not be the same, and in some examples at least one of $R_1$ through $R_8$ or $R_{10}$ or $R_{12}$ comprises epoxy and at least one other of $R_1$ through $R_8$ or $R_{10}$ or $R_{12}$ is a non-epoxy functional group. The non-epoxy functional group may be (a) a reactive group that is orthogonally reactive to an epoxy group (i.e., reacts under different conditions than an epoxy group), that serves as a handle for coupling the resin to an amplification primer, a polymer, or a polymerization agent;

or (b) a group that adjusts the mechanical or functional properties of the resin, e.g., surface energy adjustments. In some examples, the non-epoxy functional group is selected from the group consisting of an azide/azido, a thiol, a poly(ethylene glycol), a norbornene, a tetrazine, an amino, a hydroxyl, an alkynyl, a ketone, an aldehyde, an ester group, an alkyl, an aryl, an alkoxy, and a haloalkyl.

As shown in FIG. 2C, the patterned material 36, 36' includes the depressions 48, 48' respectively defined therein, and interstitial regions 46, 46' separating adjacent depressions 48, 48'. Many different layouts of the depressions 48, 48' may be envisaged, including regular, repeating, and non-regular patterns. In an example, the depressions 48, 48' are disposed in a hexagonal grid for close packing and improved density. Other layouts may include, for example, rectilinear (rectangular) layouts, triangular layouts, and so forth. In some examples, the layout or pattern can be an x-y format of depressions 48, 48' that are in rows and columns. In some other examples, the layout or pattern can be a repeating arrangement of depressions 48, 48' and/or interstitial regions 46, 46'. In still other examples, the layout or pattern can be a random arrangement of depressions 48, 48' and/or interstitial regions 46, 46'. The pattern may include spots, stripes, swirls, lines, triangles, rectangles, circles, arcs, checks, plaids, diagonals, arrows, squares, and/or cross-hatches.

The layout or pattern of the depressions 48, 48' may be characterized with respect to the density of the depressions 48, 48' (e.g., number of depressions 48, 48') in a defined area. For example, the depressions 48, 48' may be present at a density of approximately 2 million per mm². The density may be tuned to different densities including, for example, a density of about 100 per mm², about 1,000 per mm², about 0.1 million per mm², about 1 million per mm², about 2 million per mm², about 5 million per mm², about 10 million per mm², about 50 million per mm², or more, or less. It is to be further understood that the density of depressions 48, 48' in the patterned material 36, 36' can be between one of the lower values and one of the upper values selected from the ranges above. As examples, a high density array may be characterized as having depressions 48, 48' separated by less than about 100 nm, a medium density array may be characterized as having depressions 48, 48' separated by about 400 nm to about 1 µm, and a low density array may be characterized as having depressions 48, 48' separated by greater than about 1 µm. While example densities have been provided, it is to be understood that any suitable densities may be used. The density of the depressions 48, 48' may depend, in part, on the depth of the depressions 48, 48'. In some instances, it may be desirable for the spacing between depressions 48, 48' to be even greater than the examples listed herein.

The layout or pattern of the depressions 48, 48' may also or alternatively be characterized in terms of the average pitch, or the spacing from the center of the depression 48, 48' to the center of an adjacent depression 48, 48' (center-to-center spacing) or from the left edge of one depression 48, 48' to the right edge of an adjacent depression 48, 48' (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of depressions 48, 48' can be between one of the lower values and one of the upper values selected from the ranges above. In an example, the depressions 48, 48' have a pitch (center-to-center spacing) of about 1.5 µm. While example average pitch values have been provided, it is to be understood that other average pitch values may be used.

The size of each depression 48, 48' may be characterized by its volume, opening area, depth, and/or diameter.

Each depression 48, 48' can have any volume that is capable of confining at least some fluid that is introduced into the flow cell 24. The minimum or maximum volume can be selected, for example, to accommodate the throughput (e.g., multiplexity), resolution, nucleotides, or analyte reactivity expected for downstream uses of the flow cell 24. For example, the volume can be at least about $1 \times 10^{-3}$ µm³, at least about $1 \times 10^{-2}$ µm³, at least about 0.1 µm³, at least about 1 µm³, at least about 10 µm³, at least about 100 µm³, or more. Alternatively or additionally, the volume can be at most about $1 \times 10^{4}$ µm³, at most about $1 \times 10^{3}$ µm³, at most about 100 µm³, at most about 10 µm³, at most about 1 µm³, at most about 0.1 µm³, or less.

The area occupied by each depression opening can be selected based upon similar criteria as those set forth above for the volume. For example, the area for each depression opening can be at least about $1 \times 10^{-3}$ µm², at least about $1 \times 10^{-2}$ µm², at least about 0.1 µm², at least about 1 µm², at least about 10 µm², at least about 100 µm², or more. Alternatively or additionally, the area can be at most about $1 \times 10^{3}$ µm², at most about 100 µm², at most about 10 µm², at most about 1 µm², at most about 0.1 µm², at most about $1 \times 10^{-2}$ µm', or less. The area occupied by each depression opening can be greater than, less than or between the values specified above.

The depth of each depression 48, 48' can be large enough to house some of the polymeric hydrogel 40, 40'. In an example, the depth may be at least about 0.1 µm, at least about 0.5 µm, at least about 1 µm, at least about 10 µm, at least about 100 µm, or more. Alternatively or additionally, the depth can be at most about $1 \times 10^{3}$ µm, at most about 100 µm, at most about 10 µm, or less. In some examples, the depth is about 0.4 µm. The depth of each depression 48, 48' can be greater than, less than or between the values specified above.

In some instances, the diameter or length and width of each depression 48, 48' can be at least about 50 nm, at least about 0.1 µm, at least about 0.5 µm, at least about 1 µm, at least about 10 µm, at least about 100 µm, or more. Alternatively or additionally, the diameter or length and width can be at most about $1 \times 10^{3}$ µm, at most about 100 µm, at most about 10 µm, at most about 1 µm, at most about 0.5 µm, at most about 0.1 µm, or less (e.g., about 50 nm). In some examples, the diameter or length and width is about 0.4 µm. The diameter or length and width of each depression 48, 48' can be greater than, less than or between the values specified above.

In this example, at least some of components of the sequencing surface 32, 32' may be introduced into the depressions 48, 48'. It is to be understood that any space within the depressions 48, 48' not occupied by the components of the sequencing surface 32, 32' may be considered to be part of the flow channel 28.

In the example shown in FIG. 2C, the polymeric hydrogel 40, 40' is positioned within each of the depressions 48, 48'. The polymeric hydrogel 40, 40' may be applied as described in reference to FIG. 2B, so that the polymeric hydrogel 40, 40' is present in the depressions 48, 48' and not present on the surrounding interstitial regions 46, 46'.

In the example shown in FIG. 2C, the primers 42, 42' may be grafted to the polymeric hydrogel 40, 40' within each of the depressions 48, 48'. The primers 42, 42' may be applied as described in reference to FIG. 2B, and thus will graft to the polymeric hydrogel 40, 40' and not to the surrounding interstitial regions 46, 46'.

In the example shown in FIG. 2C, the chemical capture site 44, 44' includes a chemical capture agent that is applied on at least some of the interstitial regions 46, 46'. For example, the chemical capture agent may be deposited on at least some of the interstitial regions 46, 46' using microcontact printing, aerosol printing, etc. to form the chemical capture site(s) 44, 44'. In still another example, a mask (e.g., a photoresist) may be used to define the space/location where the chemical capture agent will be deposited, and thus where the chemical capture site 44, 44' will be formed. The chemical capture agent may then be deposited, and the mask removed (e.g., via lift-off, dissolution, or another suitable technique).

In other examples, the chemical capture site 44, 44' includes a chemical capture agent that is attached to free functional groups (e.g., those not attached to primers 42, 42') of the polymeric hydrogel 40, 40'. In still other examples, the chemical capture site 44, 44' includes a chemical capture agent that is attached to primers that are hybridized to some of the amplification primers 42, 42'. In these examples, the chemical capture site 44, 44' will be present in the depressions 48, 48' and not on the interstitial regions 46, 46'.

Any examples of the chemical capture agent disclosed herein may be used in the example shown in FIG. 2C.

FIG. 2D illustrates a cross-sectional view of the flow cell 24 including patterned opposed sequencing surfaces 31, 31'. In an example, each of these surfaces 31, 31' may be prepared on the substrate 26B, 26B', and then the substrates 26B, 26B' may be attached to one another (e.g., via material 50) to form an example of the flow cell 24. Each of the multi-layer substrates 26B, 26B' includes the support 34, 34' and the patterned material 36, 36' positioned on the support 34, 34'. The patterned material 36, 36' defines depressions 48, 48' separated by interstitial regions 46, 46'.

The opposed sequencing surfaces 31, 31' do not include the polymeric hydrogel 40, 40' or the primers 42, 42'. Rather, the opposed sequencing surfaces 31, 31' include the chemical capture site 44, 44' positioned in each of the depressions 48, 48'. The respective chemical capture sites 44, 44' are able to immobilize respective clustered solid supports 13. Each of the clustered solid supports introduces a respective cluster of template strands 64 into each of the depressions 48, 48'.

The chemical capture site 44, 44' in FIG. 2D includes any example of the chemical capture agent set forth herein. In this example, the chemical capture agent may be deposited in the depressions 48, 48' using microcontact printing, aerosol printing, etc. to form the chemical capture site(s) 44, 44'. In still another example, a mask (e.g., a photoresist) may be used to block the interstitial regions 46, 46', so that the chemical capture agent is deposited into the depressions 48, 48' and not on the interstitial regions 46, 46'. In this example, the chemical capture agent may then be deposited, and the mask removed (e.g., via lift-off, dissolution, or another suitable technique).

While not shown, another example of the flow cell 24 combines the non-patterned surface of FIG. 2B with the capture site 44, 44' of FIG. 2D. In this example, the concave regions 38, 38' (similar to those shown in FIG. 2B) may be coated with the chemical capture agent rather than with the polymeric hydrogel 40, 40' and primers 42, 42'. As such, the chemical capture sites 44, 44' may be formed along the entire channel 28 in the concave regions 38, 38'. In this example, the respective chemical capture sites 44, 44' are able to immobilize clustered solid supports 13 in a random distribution along the opposed sequencing surfaces.

As shown in FIG. 2B through FIG. 2D, the substrates 26A and 26A' or 26B and 26B' are attached to one another so that the sequencing surfaces 30 and 30' or 32 and 32' or 31 and 31' face each other with the flow channel 28 defined therebetween.

The substrates 26A and 26A' or 26B and 26B' may be bonded to each other at some or all of the interstitial regions 46, 46'. The bond that is formed between the substrates 26A and 26A' or 26B and 26B' may be a chemical bond, or a mechanical bond (e.g., using a fastener, etc.).

Any suitable technique, such as laser bonding, diffusion bonding, anodic bonding, eutectic bonding, plasma activation bonding, glass frit bonding, or other methods known in the art may be used to bond the substrates 26A and 26A' or 26B and 26B' together. In an example, a spacer layer (e.g., material 50) may be used to bond the substrates 26A and 26A' or 26B and 26B'. The spacer layer may be any material 50 that will seal at least some portion of the substrates 26A and 26A' or 26B and 26B' together. In some examples, the spacer layer can be a radiation-absorbing material that aids in bonding.

Method and Kit with Multiple Fluids

Figure 3A:
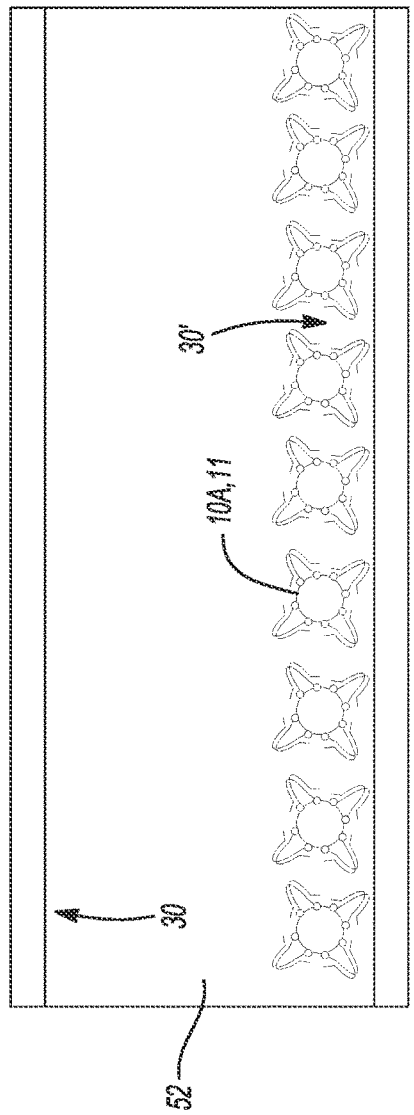
FIGS. 3A and 3B together depict one example of a method disclosed herein.
Figure 3B:
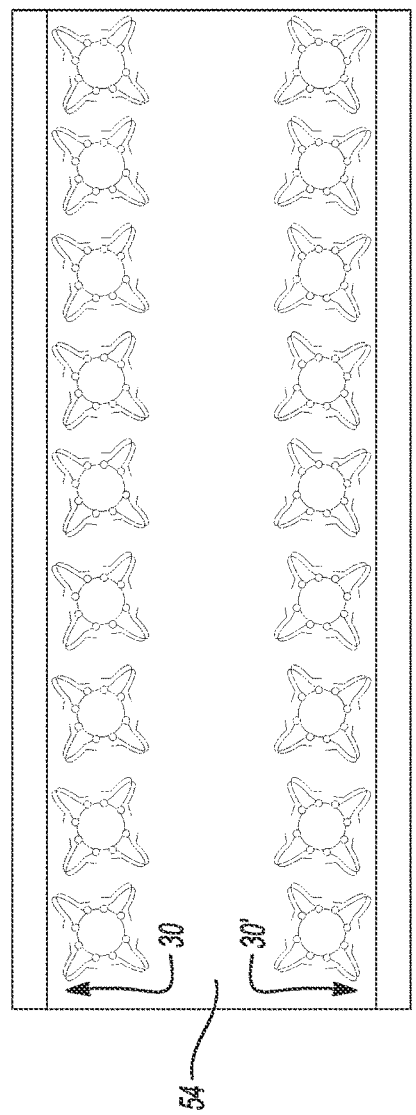

An example of the method that utilizes a combination of fluids having different densities is shown in FIG. 3A and FIG. 3B.

The method generally includes immobilizing a target material 11 (such as complexes 10A, 10B, clustered solid supports 13) at each of two opposed sequencing surfaces 30, 30' or 32, 32' or 31, 31' of a flow cell 24 by introducing a first fluid 52 (FIG. 3A), including a first portion of the target material 11 therein, into the flow cell 24, whereby at least some of the target material 11 become immobilized by capture sites 44, 44' on one 30 or 30', or 32 or 32', or 31 or 31' of the two opposed sequencing surfaces 30, 32 or 30', 32', or 31, 31'; removing the first fluid and any non-immobilized target material from the flow cell 24; and introducing a second fluid 54 (FIG. 3B), including a second portion of the target material 11 therein, into the flow cell 24, whereby at least some of the target material 11 become immobilized by capture sites 44, 44' on another 30' or 30, or 32' or 32, or 31' or 31 of the two opposed sequencing surfaces 30, 32 or 30', 32', or 31, 31'; wherein one of: the first fluid 52 has a density less than a density of the target material 11 and the second fluid 54 has a density greater than the density of the target material 11; or the second fluid 54 has the density less than the density of the target material 11 and the first fluid 52 has the density greater than the density of the target material 11.

Prior to performing the method shown in FIG. 3A and FIG. 3B, the target material 11 may be prepared or obtained.

In one example, the complexes 10A or 10B may be prepared using a nucleic acid sample and a library preparation fluid including a plurality of solid supports 12, 12' therein. In some examples, each of the solid supports 12, 12' in the library preparation fluid may have, for example, adapters (such as adapters 18) and transposome complexes attached thereto, as described in reference to FIG. 1A. Tagmentation and library preparation may be performed as defined in FIG. 1A to form the complexes 10A. The nucleic acid sample, the solid supports 12, 12', the partial Y-adapters, and the transposase enzyme may be contained in separate fluids until it is desirable to form the complexes 10A. In other examples, each of the solid supports 12, 12' in the library preparation fluid may have, for example, oligonucleotides attached thereto. In some examples, PCR-free nucleotide library preparation may take place separately from the solid supports 12, 12', and then the prepared library fragments can be hybridized to the oligonucleotides at the surface of the solid supports 12, 12', as described in reference to FIG. 1B. Other examples of library preparation may be used (e.g., including PCR), as long as the fragments are denatured into single stranded fragments before being hybridized to the oligos on the solid supports 12, 12'.

In another example, the clustered solid supports 13 may be prepared by amplifying a library fragment in the presence of a plurality of solid supports 12, 12' functionalized with primers 42, 42'.

The target material 11 (e.g., complexes 10A or 10B, or any other solid support 12, 12' having sequencing-ready fragments 14, 14' attached thereto, or clustered solid supports 13) may be divided into first and second portions. The first portion of the target material 11 may be incorporated into the first fluid 52 and the second portion of the target material 11 may be introduced into the second fluid 54.

The first and second fluids 52, 54 have different densities. In one example, the first fluid 52 has a density less than a density of the target material 11 and the second fluid 54 has a density greater than the density of the target material 11. In one specific example, the first fluid 52 has a density less than a density of the solid support 12, 12' of the complexes 10A or 10B or clustered solid support 13 and the second fluid 54 has a density greater than the density of the solid support 12, 12' of the complexes 10A or 10B or clustered solid support 13. In another example, the second fluid 54 has the density less than the density of the target material 11 and the first fluid 52 has the density greater than the density of the target material 11. In another specific example, the second fluid 54 has the density less than the density of the solid support 12, 12' of the complexes 10A or 10B or clustered solid support 13 and the first fluid 52 has the density greater than the density of the solid support 12, 12' of the complexes 10A or 10B or clustered solid support 13. As such, the density of each of the fluids 52, 54 depends upon the target material 11 that is used. In some examples, the density of the complexes 10A or 10B or clustered solid support 13 is approximately equal to the density of the solid support 12, 12' used in the complex 10A or 10B or the clustered solid support 13, and thus in the specific examples that are provided, the density of each of the fluids 52, 54 depends upon the solid support 12, 12' that is used in the target material 11.

The densities of the fluid 52, 54 may be measured at a capture temperature of the target material 11 (e.g., complex 10A, 10B or clustered solid support 13) that is introduced into the flow cell 24. In an example, the capture temperature ranges from about 18° C. to about 40° C.

In one example, the density of one of the fluids 52 or 54 at the capture temperature is at least 0.1 g/cm$^3$ less than the density of the target material 11 (e.g., the solid support 12, 12' of the complexes 10A or 10B or clustered solid support 13) at the capture temperature, and the density of the other of the fluids 54 or 52 at the capture temperature is at least 0.1 g/cm$^3$ greater than the density of the target material 11 (e.g., the solid support 12, 12' of the complexes 10A or 10B or clustered solid support 13) at the capture temperature. In one specific example, when the density of the target material (e.g., solid support 12, 12') is X g/cm$^3$, the density of one of the fluids 52 or 54 at the capture temperature is X g/cm$^3$−0.1 g/cm$^3$, and the density of the other of the fluids 54 or 52 at the capture temperature is X g/cm$^3$+0.1 g/cm$^3$.

In an addition to having the respective densities, the fluids 52, 54 should also be compatible with the target material 11. When complexes 10A, 10B are used, the fluids 52, 54 should be compatible the complexes 10A, 10B and the sequencing surfaces 30, 30' or 32, 32' or 31, 31' so that the fragments 14, 14', 14'' and the primers 42, 42' are not deleteriously affected. When clustered solid supports 13 are used, the fluids 52, 54 should be compatible the clustered solid support 13 so that the template strands 64 are not deleteriously affected.

The lower density fluid 52 or 54 may be any aqueous buffer solution (e.g., a weak acid and one of its salts (conjugate base) or a weak base and one of its salts (conjugate acid). The salt concentration in the aqueous buffer solution may be adjusted so that the density of the lower density fluid 52 or 54 is less than the density of the target material 11 (e.g., the density of the solid support 12, 12' of the complexes 10A, 10B or clustered solid supports 13). The greater the density difference is between the target material 11 and the lower density fluid 52 or 54, the faster the settling time is of the target material 11 (e.g., complexes 10A, 10B or clustered solid supports 13) in the lower density fluid 52 or 54. As examples, the lower density fluid 52 or 54 may be a Tris-HCl buffer or 0.5× saline sodium citrate (SSC) buffer. In an example, the lower density fluid 52 or 54 is an aqueous buffer solution having a density of about 1 g/cm$^3$. This lower density fluid 52 or 54 may be particular suitable for use with a target material 11 having a density of about 1.18 g/cm$^3$.

The higher density fluid 54 or 52 may be an aqueous salt solution. The salt selected should render the fluid 52 or 54 as "heavy" and should also not deleteriously affect the target material. When complexes 10A, 10B are used, the salt should not deleteriously affect the complexes 10A, 10B or the primers 42, 42'. When clustered solid supports 13 are used, the salt should not deleteriously affect the template strands 64. The salt concentration in the aqueous buffer solution may be adjusted so that the density of the higher density fluid 54 or 52 is greater than the density of the target material 11. Examples of the higher density fluid 54 or 52 include sodium polytungstate solutions and sodium chloride solutions. In an example, the higher density fluid 54 or 52 is a sodium polytungstate solution having a density ranging from about 2 g/cm$^3$ to about 3 g/cm$^3$. These higher density fluids 54 or 52 may be particular suitable for use with a target material 11 having a density of about 1.18 g/cm$^3$. In these examples, the sodium polytungstate solution has a concentration ranging from about 1 gram of sodium polytungstate per 1 milliliter of water to about 2.52 grams of sodium polytungstate per 1 milliliter of water. In another example, a 25% (w/v) sodium chloride solution has a density of about 1.2 g/cm$^3$.

In one example, the first or second fluid 52 or 54 having the density less than the density of the target material is an aqueous buffer solution, and the second or first fluid 54 or 52 having the density greater than the density of the target material is a sodium polytungstate solution or a sodium chloride solution. In another example, the density of the first or second fluid 52 or 54 that is less than the density of the target material is about 1 g/cm$^3$ at a capture temperature, and wherein the density of the second or first fluid 54 or 52 that is greater than the density of the target material is about 2 g/cm$^3$ at the capture temperature.

As shown in FIG. 3A, one example of the method involves introducing the first fluid 52 including some of the target material 11 (e.g., complexes 10A in FIG. 3A) into the flow cell 24. In this example, the first fluid 52 has a lower density than the density of the solid support 12, 12' of the complexes 10A, and thus the complexes 10A migrate to or settle at the bottom sequencing surface 30'. The capture sites 44' (not shown in FIG. 3A) immobilize at least some of the complexes 10A at the bottom sequencing surface 30'.

It is to be understood that some complexes 10A (or other target material 11) in the first fluid 52 may not settle, and these complexes 10A (or other target material) will be removed from the flow cell 24 before further processing. A predetermined time may be allowed to pass before removing the first fluid 52 and any non-immobilized target material (e.g., complexes 10A) from the flow cell 24. In an example, the predetermined time may range from about 5 minutes to about 30 minutes in order to obtain a desirable number of immobilized complexes 10A or other target material 11. Longer incubation times may also be used.

This example method then includes washing away the first fluid 52 and non-immobilized target material 11 (e.g., complexes 10A) from the flow cell 24. Washing may involve introducing a washing fluid into the flow cell 24. The flow may push any complexes 10A (or other target materials 11) that have not settled and become immobilized at the sequencing surface 30' out through an exit port of the flow cell 24. The immobilization mechanism (e.g., binding pair, hybridization, covalent bonding, etc.) between the complexes 10A (or other target materials 11) and the capture sites 44' of the sequencing surface 30' may prevent any settled and immobilized complexes 10A (or other immobilized target materials 11) from becoming part of the exit flow. Moreover, the target material 11 (e.g., complexes 10A in FIG. 3A) immobilized on one of the two opposed sequencing surfaces (e.g., sequencing surface 30' in FIG. 3A) remains immobilized on that sequencing surface when the second fluid 54 is introduced.

As shown in FIG. 3B, this example of the method involves introducing the second fluid 54 including some other of the target material 11 (e.g., complexes 10A) into the flow cell 24. In this example, the second fluid 54 has a higher density than the density of the solid support 12, 12' of the complexes 10A (or other target material 11), and thus the complexes 10A migrate to the top sequencing surface 30. The capture sites 44 (not shown in FIG. 3B) immobilize at least some of the complexes 10A at the sequencing surface 30.

Prior to performing seeding, amplification, and sequencing or sequencing (as described below), this example method may further include removing the second liquid 54 and non-immobilized target material 11 from the flow cell 24. As such, this example method may then include washing away the second fluid 54 and non-trapped target material 11 (e.g., non-immobilized complexes 10A) from the flow cell 24. Washing may be performed as described herein. The flow may push any complexes 10A (or other target materials 11) that have not become immobilized at the upper sequencing surface 30 out through an exit port of the flow cell 24. It is to be understood that he immobilization mechanism (e.g., binding pair, hybridization, covalent bonding, etc.) between the complexes 10A (or other target materials 11) and the respective capture sites 44, 44' of the sequencing surfaces 30, 30' may prevent any immobilized complexes 10A (or other immobilized target materials 11) from becoming part of the exit flow.

Figure 9A:
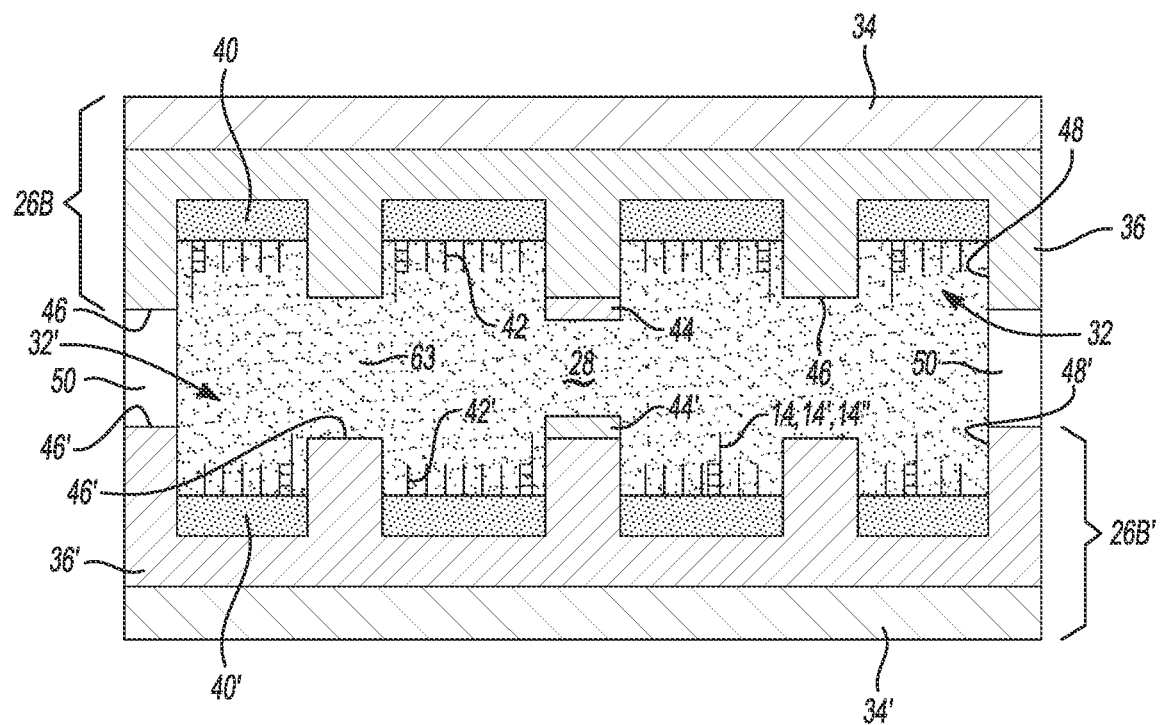
FIG. 9A through FIG. 9C together depict an example of a method for reducing diffusion and convection of template strands during amplification.
Figure 9B:
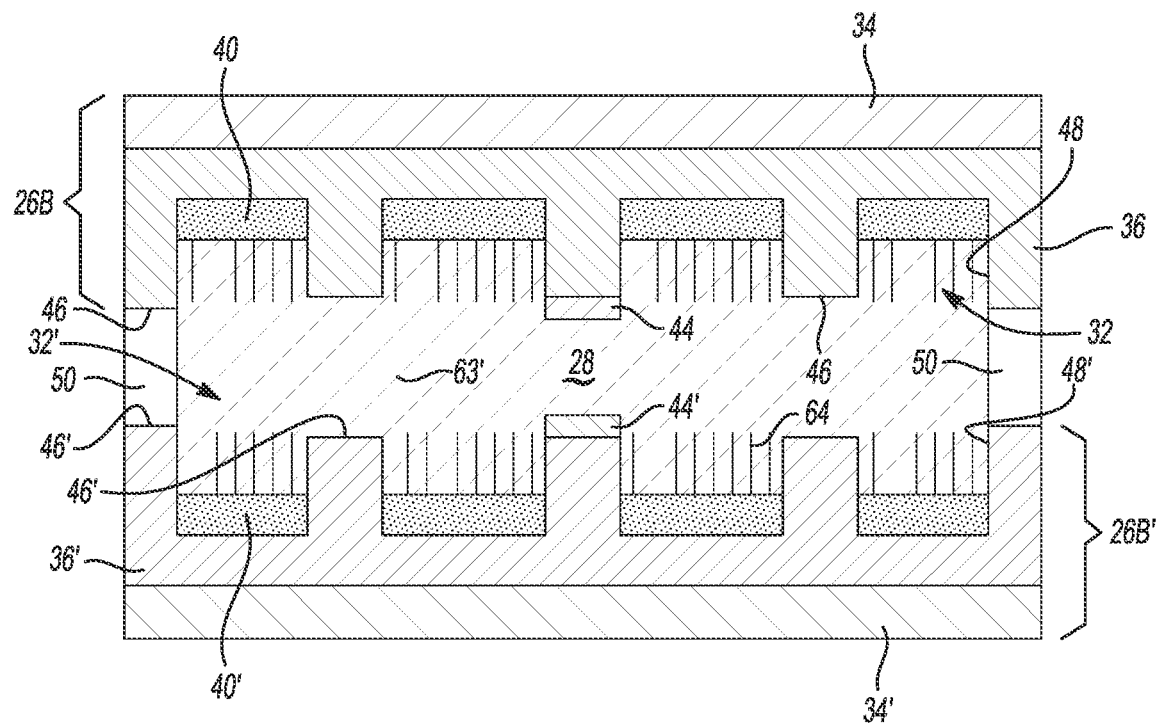
Figure 9C:
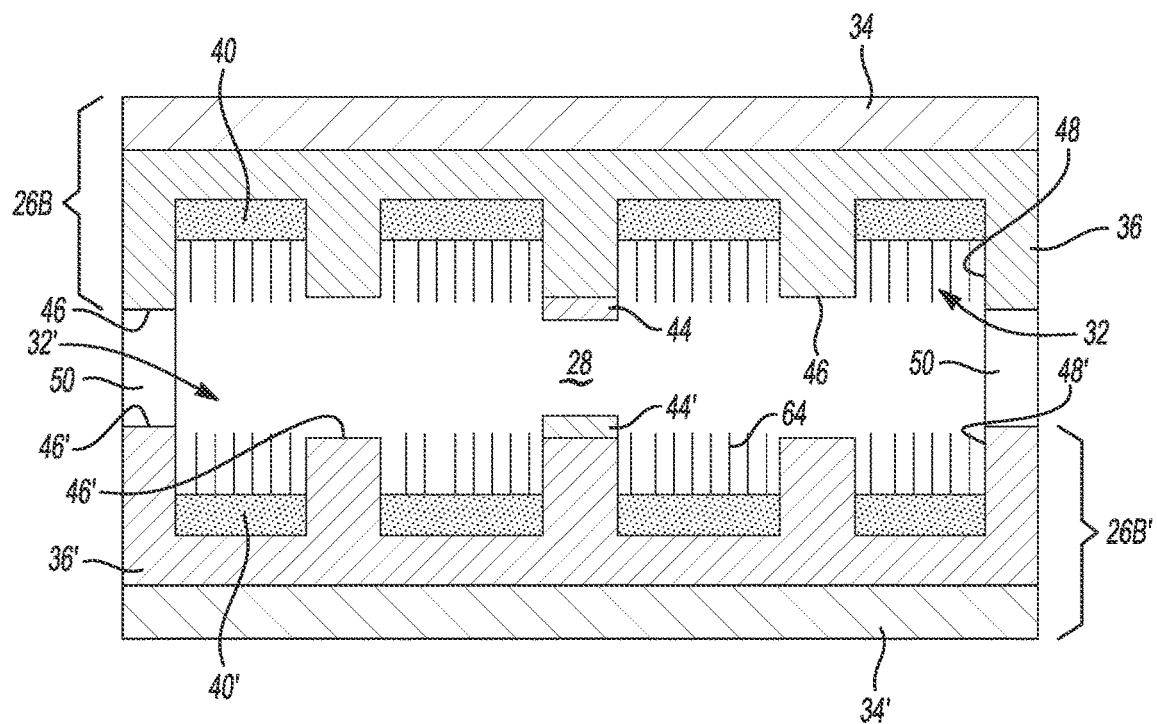

When complexes 10A or 10B are used, this washing step may be followed by library fragment release and amplification (e.g., an example of which is described in reference to FIG. 9A through FIG. 9C). When clustered solid supports 13 are used, this washing step may be followed by sequencing.

While the example shown in FIG. 3A and FIG. 3B illustrates the introduction of the lower density fluid and then the higher density fluid, it is to be understood that the higher density fluid may be introduced first to immobilize target material 11 on the upper sequencing surface 30, and then the lower density fluid may be introduced to immobilize target material 11 on the lower/bottom sequencing surface 30'. Moreover, it is to be understood that this method may be performed with any example of the flow cell 24 disclosed herein, including those with the patterned surfaces 32, 32'. When the clustered solid supports 13 are used, a flow cell 24 without amplification primers 42, 42', such as that shown and described in reference to FIG. 2D, may be used.

A kit to perform the method described in reference to FIGS. 3A and 3B may include a preparation fluid including a target material 11 therein; a first introduction fluid (e.g., fluid 52 or 54) having a density less than a density of the target material 11; and a second introduction fluid (fluid 54 or 52) having a density greater than the density of the target material 11. In one example kit, the first introduction fluid is an aqueous buffer solution, and the second introduction fluid is a sodium polytungstate solution or a sodium chloride solution. In one example when the second introduction fluid is the sodium polytungstate solution, the sodium polytungstate solution has a concentration of about 1 gram of sodium polytungstate per 1 milliliter of water. In another example kit, the density of the first introduction fluid at a capture temperature is at least 0.1 $g/cm^3$ less than the density of the target material 11 at the capture temperature, and the density of the second introduction fluid at the capture temperature is at least 0.1 $g/cm^3$ greater than the density of the target material 11 at the capture temperature. In still another example, the density of the first introduction fluid is about 1 $g/cm^3$ at a capture temperature, and wherein the density of the second introduction fluid is about 2 $g/cm^3$ at the capture temperature.

In some examples, the preparation fluid including the target material 11 includes the solid supports 12, 12', and the kit may also include other library preparation components, such as a nucleic acid sample, partial Y-adapters, transposase enzymes, etc.; each of which may be contained in a separate fluid until it is desirable to form the target material 11, such as the complex 10A, 10B, the clustered solid support 13, etc. Some examples of the kit may also include the flow cell 24. Other examples of the kit may include preparation fluids that include any examples of the target material 11 disclosed herein.

Methods and Kits with One Fluid

Other examples of the method disclosed herein utilize one fluid during the immobilization of the target material 11. Some methods utilize one target material 11 and different modalities to achieve immobilization across the opposed sequencing surfaces 30, 30' or 32, 32' or 31, 31'. Other methods utilize two different target materials 11 (each having at least one property that is different from each other), and the same or different modalities to achieve immobilization across the opposed sequencing surfaces 30, 30' or 32, 32' or 31, 31'. Different examples are described herein in reference to FIG. 4A and FIG. 4B through FIG. 8A and FIG. 8B.

Prior to performing any of the methods shown in FIG. 4A and FIG. 4B through FIG. 8A and FIG. 8B, the complexes 10A or 10B or clustered solid supports 13 may be prepared as described herein.

The complexes 10A or 10B may be prepared using a nucleic acid sample and a library preparation fluid including a plurality of magnetic solid supports 12' therein. In some examples, each of the magnetic solid supports 12' in the library preparation fluid may have, for example, adapters (such as adapters 18) and transposome complexes attached thereto, as described in reference to FIG. 1A. Tagmentation and library preparation may be performed as defined in FIG. 1A to form the complexes 10A. The nucleic acid sample, the magnetic solid supports 12', the partial Y-adapters, and the transposase enzyme may be contained in separate fluids until it is desirable to form the complexes 10A. In other examples, each of the magnetic solid supports 12' in the library preparation fluid may have, for example, oligonucleotides attached thereto. In some examples, PCR-free nucleotide library preparation may take place separately from the magnetic solid supports 12', and then the prepared library fragments can be hybridized to the oligonucleotides at the surface of the magnetic solid supports 12', as described in reference to FIG. 1B. Other examples of library preparation may be used (e.g., including PCR), as long as the fragments are denatured into single stranded fragments before being hybridized to the oligos on the magnetic solid supports 12'.

The clustered solid supports 13 may be prepared by amplifying a library fragment in the presence of a plurality of solid supports 12, 12' funcionalized with primers 42, 42'.

An example of the method that utilizes a fluid, a substantially uniform magnetic force, and a magnetically responsive target material, such as the solid support 12' is shown in FIG. 4A and FIG. 4B. The method generally includes immobilizing a target material 11 at each of two opposed sequencing surfaces 30, 30' or 32, 32' of a flow cell 24 by introducing a fluid 56, including the target material 11, into the flow cell 24, wherein the fluid 56 has a density approximately equivalent to a density of the magnetic solid support 12'; allowing some of the target material 11 to become immobilized by capture sites 44 or 44' (not shown in FIG. 4A) on one 30 or 30', or 32 or 32', or 31 or 31', of the two opposed sequencing surfaces 30, 30' or 32, 32' or 31, 31'; and applying a magnetic force to another 30' or 30, or 32' or 32, or 31' or 31 of the two opposed sequencing surfaces 30, 30' or 32, 32' or 31, 31', thereby pulling some other of the target material 11 to the other 30' or 30, or 32' or 32, or 31' or 31 of the two opposed sequencing surfaces 30, 30' or 32, 32' or 31, 31' where they become immobilized by capture sites 44' or 44 (not shown in FIG. 4B) on the other of the two opposed sequencing surfaces 30, 30' or 32, 32' or 31, 31'. When complexes 10A, 10B are used and prior to performing seeding and amplification (as described below), this example method may further include ceasing the application of the magnetic force and removing the fluid and non-immobilized target material from the flow cell 24. These steps may be followed by library fragment release and amplification (e.g., as described in reference to FIG. 9A through FIG. 9C).

The target material 11 (e.g., complexes 10A, 10B, or any other magnetic solid support 12' having sequencing-ready fragments 14, 14', 14", or clustered solid supports 13) attached thereto, may be incorporated into the fluid 56. As one example, from about 25,000 target materials 11 (e.g., complexes 10A, 10B or clustered solid supports 13) to about 500,000 target materials 11 may be included in a microliter of fluid. As another example, from about 100,000 target materials 11 to about 500,000 target materials 11 may be included in a microliter of fluid. Other concentrations may be used depending upon the size of the flow cell 24.

The density of the fluid 56 may be measured at a capture temperature of the target materials 11 that is introduced into the flow cell 24. In an example, the capture temperature ranges from about 18° C. to about 40° C.

The fluid 56 is selected to have a density that is at least approximately equivalent to the density of the magnetic solid support 12' of the target material 11. In these examples, "at least approximately equivalent," means that the density of the fluid 56 is within 0.08 g/cm$^3$ of the density of the magnetic solid support 12'. In some instances, the densities of the fluid 56 and the magnetic solid supports 12' are the same. By having an at least approximately equivalent density with the magnetic solid support 12', the fluid 56 functions as a mild floating agent. As used herein, the term "mild floating agent" refers to a fluid in which the target material 11 (e.g., complexes 10A, 10B, clustered solid supports 13, etc.) are able to float for at least some time period before sinking or settling. In the fluid 56, some of the target material 11 begins to sink and become immobilized to the lower/bottom sequencing surface 30', 32', 31' in the flow cell 24, while other target material 11 remains afloat (at least for some period of time).

The fluid 56 may be any aqueous buffer solution. The salt concentration in the aqueous buffer solution may be adjusted so that the density of the fluid 56 is at least approximately equal to the density of the magnetic solid support 12'. In other words, the salt concentration in the aqueous buffer solution may be adjusted so that the density of the fluid 56 is within +/−0.08 g/cm$^3$ of the density of the magnetic solid support 12'. As examples, the fluid 56 may be a Tris-HCl buffer or 0.5× saline sodium citrate (SSC) buffer or a 75 mM sodium citrate solution (pH=7) containing about 750 mM NaCl. In an example, the density of each of the magnetic solid support 12' and the fluid 56 is about 1.1 g/cm$^3$.

After the fluid 56 and the target material 11 are introduced into the flow cell 24, the target material 11 initially floats in the fluid 56. As time passes, some of the target material 11 will settle to the lower/bottom sequencing surface 30', 32', 31' where it becomes immobilized at the capture site(s) 44'. An example is shown in FIG. 4A, where some of the complexes 10A have settled on the lower/bottom sequencing surface 30'. The fluid 56 helps to prevent settling of all of the target material 11 on the lower/bottom sequencing surface 30', 32', 31' too fast.

As such, after introduction of the fluid 56 and immobilization of some of the target material 11, there is time for an externally applied magnetic force to be applied to the other sequencing surfaces 30, 32, 31 in the flow cell 24. The magnetic force attracts the floating target material 11 to the upper/top sequencing surface 30, 32, 31 in the flow cell 24. An example is shown in FIG. 4B, where some of the complexes 10A have migrated to the upper/top sequencing surface 30.

In this example method, a predetermined time period may be allowed to pass between the introduction of the fluid 56 and the application of the magnetic force. This may be desirable so that some of the target material 11 settles and becomes immobilized at the one sequencing surface 30', 32', 31' while the remaining target material 11 stays afloat in the fluid 56. In an example, this predetermined time ranges from about 5 minutes to about 30 minutes. In some examples, the predetermined time period passes between the introduction of the fluid 56 and the application of the magnetic force, and the predetermined time ranges from about 5 seconds to about 2 minutes.

As shown in FIG. 4B, the magnetic force is then applied by placing a magnet 58 on an exterior surface 60 of the flow cell 24 that is adjacent to the sequencing surface 30, 32. The magnet 58 should have a magnetic field strength that is sufficient to attract the floating target material 11 (e.g., complexes 10A, 10B, clustered solid supports 13, etc.)

without attracting the target material 11 that is already immobilized on the lower/bottom sequencing surface 30', 32', 31'. The magnetic field strength is relatively weak, but is at least substantially uniformly applied across the entire length and width of the flow channel 28. A relatively weak magnetic field strength may range from about 1 mT (milliTesla) to about 100 mT. In some examples, the strength of the relatively weak magnetic field ranges from about 1 mT to about 10 mT, or from about 10 mT to about 100 mT. This enables floating target material 11 to become immobilized to capture sites 44 across the upper/top sequencing surface 30, 32, 31. Stronger magnets, such as neodymium magnets, may be used in some instances, and these magnets have a field strength of about 1 T (Tesla).

In an example, the magnet 58 has the same length and width as the flow channel 28 and/or the flow cell 24. In an example, the magnet 58 is similar to a refrigerator magnet and has a magnetic field strength of about 5 mT. In another example, the magnet 58 is an elastomeric strip that has small magnetic particles embedded therein. These types of flexible magnets are commercially available, for example, from Uline, Arnold Magnetic Technologies (FLEXMAG™), etc. In an example, the application of the magnetic force involves placing an elastomeric strip embedded with magnetic particles on an exterior surface 60 of the flow cell 24 adjacent to the other of the two opposed sequencing surfaces (i.e., the sequencing surface 30 that does not have the target material 11 immobilized thereon). In some examples, the magnet may be applied manually. In other examples, the application of the magnetic force may be automated, e.g., when it is integrated into the sequencing system.

The time frame for application of the magnet 58 (and thus the magnetic force) depends, in part, upon the strength of the magnet and the concentration of the complexes 10A, 10B in the fluid 56. As an example, the magnet 58 may be applied for 5 seconds to about 2 minutes. Examples of the method then include ceasing the application of the magnetic force. This may be accomplished by removing the magnet 58.

It is to be understood that some target material 11 (e.g., complexes 10A, 10B, clustered solid supports 13) in the fluid 56 may not become immobilized at either of the sequencing surface 30, 30' or 32, 32' or 31, 31', and this target material 11 can be removed from the flow cell 24 before further processing. As such, this example method may include washing away the fluid 56 and non-trapped target material 11 from the flow cell 24. Washing may involve introducing a washing fluid into the flow cell 24. The flow may push any target material 11 that has not become immobilized at the sequencing surfaces 30, 30' or 32, 32' or 31, 31' out through an exit port of the flow cell 24. The immobilization mechanism (e.g., binding pair, hybridization, covalent bonding, etc.) between the target material 11 and the capture sites 44, 44' of the sequencing surfaces 30, 30' or 32, 32' or 31, 31' may prevent any immobilized target material 11 from becoming part of the exit flow.

While the example shown in FIG. 4A and FIG. 4B illustrates the flow cell 24 with sequencing surfaces 30 and 30', it is to be understood that this method may be performed with any example of the flow cell 24 disclosed herein, including those with the patterned sequencing surface 32, 32'. When clustered solid supports 13 including magnetically responsive solid supports 12' are used, a flow cell 24 without amplification primers 42, 42' may be used, such as that shown and described in reference to FIG. 2D. Moreover, any other magnetically responsive target material may be used in this example of the method.

A kit to perform the method described in reference to FIGS. 4A and 4B may include a preparation fluid including a plurality of magnetic solid supports 12' therein; and an introduction fluid (e.g., fluid 56) having a density approximately equivalent to a density of the magnetic solid support 12'. The kit may also include other library preparation components, such as a nucleic acid sample, partial Y-adapters, transposase enzymes, etc.; each of which may be contained in a separate fluid until it is desirable to form the target material 11, such as the complex 10A, 10B, clustered solid support 13, etc. Some examples of the kit may also include the flow cell 24. Still other examples of the kit may include an amplification mix including a liquid form of a temperature responsive material.

The methods shown in FIG. 5A and FIG. 5B, FIG. 6A and FIG. 6B, FIG. 7A and FIG. 7B, and FIG. 8A and FIG. 8B will now be described. Each of these methods uses a combination of target materials (e.g., 11A and 11B, or 11C and 11D, etc.), and different target material combinations are described in more detail with respect to each set of figures. Each set of figures depicts the method being performed with the flow cell 24 having non-patterned sequencing surfaces 30, 30'. However, it is to be understood that any of these methods may be performed with any example of the flow cell 24 disclosed herein, including those with the patterned surfaces 32, 32'. Additionally, when the clustered solid supports 13 are used as the target materials (e.g., 11A and 11B, etc.), a flow cell 24 without amplification primers 42, 42', such as that shown and described in reference to FIG. 2D, may be used.

Figure 5A:
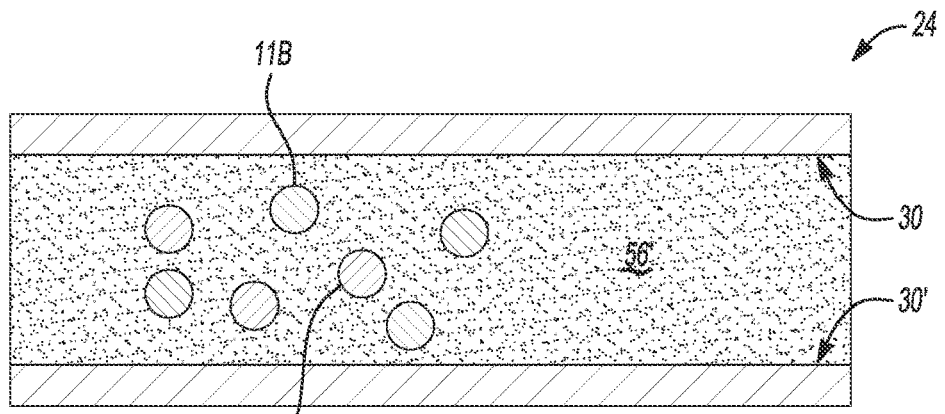
FIGS. 5A and 5B together depict still another example of a method disclosed herein.
Figure 5B:
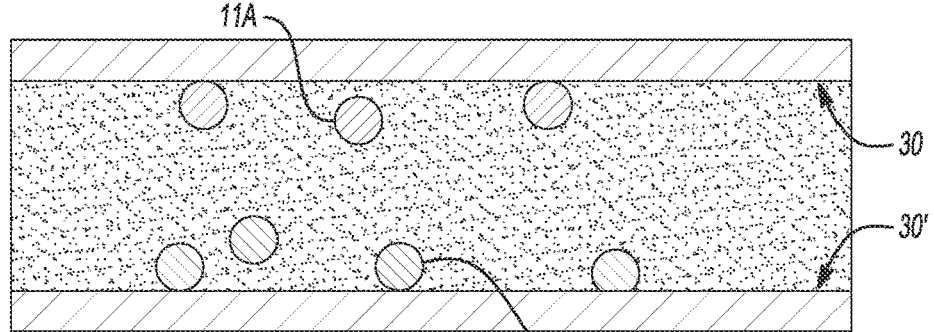

One example of the method that utilizes a combination of target materials 11A, 11B is shown in FIG. 5A and FIG. 5B. In this example, the target materials 11A, 11B have densities that are different from each other and different from a carrier fluid.

This example method generally includes simultaneously immobilizing a first target material 11A at a first 30 or 32 or 31 of two opposed sequencing surfaces 30, 30', or 32, 32', or 31, 31' of a flow cell 24 and a second target material 11B at a second 30' or 32' or 31' of the two opposed sequencing surfaces 30, 30', or 32, 32', or 31, 31' by introducing, into the flow cell 24, a target fluid 56' including the first target material 11A and the second target material 11B, wherein the carrier fluid of the target fluid 56' has a fluid density; the first target material 11A has a first density less than the fluid density; and the second target material 11B has a second density greater than the fluid density.

The density of the carrier fluid of the target fluid 56' may be measured at a capture temperature of the target materials 11A, 11B that are introduced into the flow cell 24. In an example, the capture temperature ranges from about 18° C. to about 40° C.

In one example, the density of one of the target materials 11A is at least 0.1 g/cm$^3$ less than the density of the carrier fluid at the capture temperature, and the density of the other of the target materials 11B is at least 0.1 g/cm$^3$ greater than the density of the carrier fluid at the capture temperature. In one specific example, when the density of the carrier fluid is X g/cm$^3$ at the capture temperature, the density of one of the target materials 11A or 11B is X g/cm$^3$−0.1 g/cm$^3$, and the density of the other the target materials 11B or 11A is X g/cm$^3$+0.1 g/cm$^3$.

The carrier fluid of the target fluid 56' may be any of the aqueous buffer solutions or aqueous salt solutions set forth herein. The salt concentration in the aqueous buffer solution or aqueous salt solution may be adjusted so that the density of the carrier fluid at the capture temperature is between the respective densities of the target materials 11A, 11B. In another example, the carrier fluid of the target fluid 56' is an ionic liquid.

The target materials 11A, 11B may be complexes 10A, 10B or clustered solid supports 13. The support 12 for the target materials 11A, 11B may be any of the examples set forth herein as long as the densities of the respective materials 11A, 11B are different with respect to the carrier fluid, as described in this example method. The density of the solid support 12 in each of the target materials 11A, 11B is at least approximately equal to the density of the respective target material 11A, 11B. As such, the solid support 12 of the target material 11A is selected to have a density that is lower than the density of the carrier fluid of the target fluid 56' at the capture temperature, and the solid support 12 of the target material 11B is selected to have a density that is higher than the density of the carrier fluid of the target fluid 56' at the capture temperature.

As shown in FIG. 5A, this method involves introducing the target fluid 56' including the target materials 11A, 11B into the flow cell 24. The target fluid 56' may be allowed to incubate in the flow cell 24 for a predetermined time. In an example, the predetermined time may range from about 5 minutes to about 30 minutes in order to obtain a desirable number of immobilized target materials 11A, 11B on the sequencing surfaces 30, 30'. Longer incubation times may also be used.

As mentioned, the solid support 12 of the target material 11A has a lower density than the density of the carrier fluid at the capture temperature, and thus the target material 11A migrates or floats to the upper sequencing surface 30, as shown in FIG. 5B. The capture sites 44 (not shown in FIG. 5B) immobilize at least some of the target material 11A at the upper sequencing surface 30. Also as mentioned, the solid support 12 of the target material 11B has a higher density than the density of the carrier fluid at the capture temperature, and thus the target material 11B migrates to or settles on the bottom sequencing surface 30', as shown in FIG. 5B. The capture sites 44' (also not shown in FIG. 5B) immobilize at least some of the target material 11B at the lower/bottom sequencing surface 30'.

The immobilization of the target materials 11A, 11B occurs simultaneously upon introduction of the target fluid 56' to the flow cell 24 due to the different densities of the target materials 11A, 11B with respect to the carrier fluid. As such, in the method of FIG. 5A and FIG. 5B, at least some of the first target material 11A becomes immobilized by respective capture sites 44 on the first of the two opposed sequencing surfaces 30, and at least some of the second target material 11B becomes immobilized by respective capture sites 44' on the second of the two opposed sequencing surfaces 30'.

It is to be understood that some target materials 11A, 11B may not become immobilized, and these target materials 11A, 11B will be removed from the flow cell 24 before further processing. As such, this example method then includes washing away the carrier fluid of the target fluid 56' and non-immobilized target materials 11A, 11B from the flow cell 24. Washing may involve introducing a washing fluid into the flow cell 24. The flow may push any target materials 11A, 11B that have not become immobilized at the sequencing surfaces 30, 30' out through an exit port of the flow cell 24. The immobilization mechanism (e.g., binding pair, hybridization, covalent bonding, etc.) between the respective target materials 11A, 11B and the capture sites 44, 44' of the sequencing surfaces 30, 30' may prevent any immobilized target materials 11A, 11B from becoming part of the exit flow.

When complexes 10A or 10B are used as the target materials 11A, 11B, this washing step may be followed by library fragment release and amplification (e.g., an example of which is described in reference to FIG. 9A through FIG. 9C). When clustered solid supports 13 are used, this washing step may be followed by sequencing.

A kit to perform the method described in reference to FIGS. 5A and 5B may include the target fluid 56', which includes the carrier fluid having a fluid density; a first target material 11A having a first density less than the fluid density; and a second target material 11B having a second density greater than the fluid density.

In some examples, the first and second target materials 11A, 11B are complexes 10A or 10B. In these examples, the first target material 11A includes a first solid support 12 having a first solid support density approximately equal to the first density (i.e., less than the fluid density), and sequencing-ready nucleic acid fragments 14, 14', 14" attached to the first solid support 12; and the second target material 11B includes a second solid support 12 having a second solid support density approximately equal to the second density (i.e., greater than the fluid density), and sequencing-ready nucleic acid fragments 14, 14', 14" attached to the second solid support 12.

In other examples, the first and second target materials 11A, 11B are clustered solid supports 13. In these examples, the first target material 11A includes a first solid support 12 having a first solid support density approximately equal to the first density (i.e., less than the fluid density), and a first cluster of template strands 64 attached to the first solid support 12; and the second target material 11B includes a second solid support 12 having a second solid support density approximately equal to the second density (i.e., greater than the fluid density), and second cluster of template strands 64 attached to the second solid support 12.

The kit may alternatively include the carrier fluid, reagents and materials to prepare the target material 11A, and reagents and materials to prepare the target material 11B. In this example, the respective target materials 11A, 11B may be prepared using the respective reagents and materials and as described herein, and then they may be added to the carrier fluid to form the target fluid 56'.

Other examples of the method utilize different target materials and different modalities to immobilize the target materials. These examples generally include introducing first and second target materials to a flow cell 24 including two opposed sequencing surfaces 30, 30' or 32, 32' or 31, 31', wherein the first target material has at least one property that is different from the second target material, wherein the at least one property is selected from the group consisting of density, charge, magnetism, and combinations thereof; and exposing the first and second target materials to at least one condition, thereby causing the first target material to become immobilized by a capture site 44 on a first of the two opposed sequencing surfaces 30, 32, or 31 and the second target material to become immobilized by a capture site 44' on a second of the two opposed sequencing surfaces 30', 32', 31'.

Figure 6A:
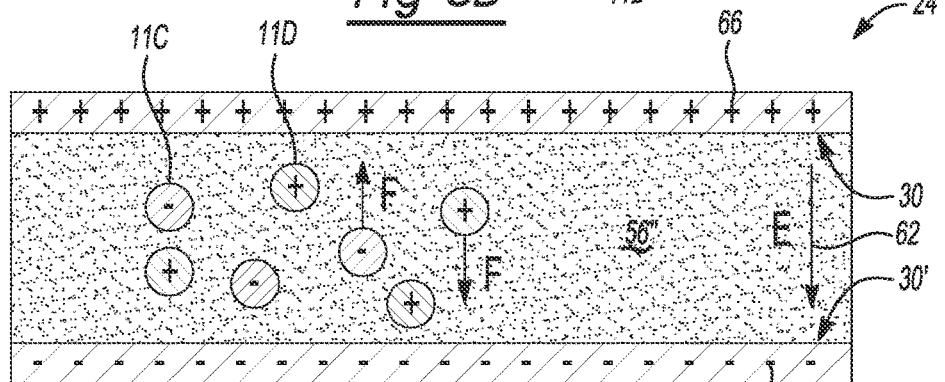
FIGS. 6A and 6B together depict yet another example of a method disclosed herein.
Figure 6B:
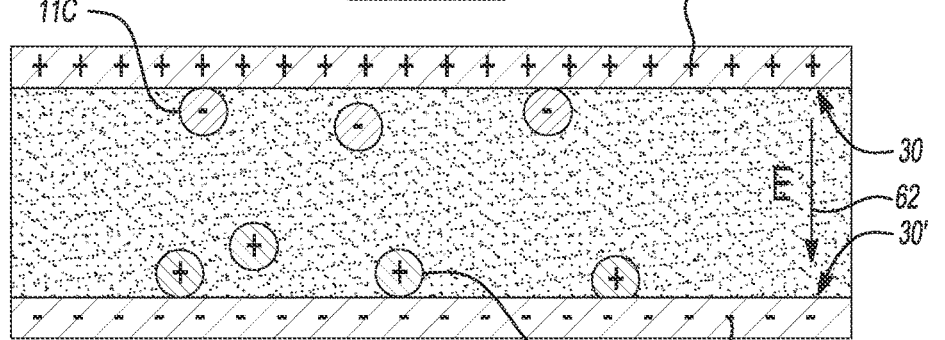

One example method is shown in FIG. 6A and FIG. 6B. In this example, the target materials 11C, 11D have opposite charges.

As depicted in FIG. 6A, the first target material 11C has a negative charge and the second target material 11D has a positive charge. Any examples of the charged solid supports 12 described herein may be used in this example. In one example, the negatively charged first target material 11C is selected from the group consisting a carboxylated solid support, a polyglutamic acid coated solid support, and a sulfate functionalized solid support; and the positively charged second target material 11D is selected from the group consisting of an amine functionalized solid support, such as a chitosan functionalized solid support and a polylysine functionalized solid support.

The target materials 11C, 11D may be part of a fluid 56" that is introduced into the flow cell 24. In this example, the fluid 56" used to introduce the charged target materials 11C, 11D to the flow cell 24 may be an electrolyte. As one example, the fluid 56" may be a combination of tris(hydroxymethyl amino-methane and boric acid present at the same molarity (e.g., 4.5 mM of each). When complexes 10A, 10B are used as the target materials 11C, 11D, a low salt buffer may be used, such as a saline-sodium citrate (SSC) buffer (e.g., about 45 mM) with about 4 mM of $Mg^{2+}$). This type of fluid 56" can maximize charges on the charged target materials 11C, 11D while also allowing hybridization when the library fragments 14, 14', 14' are released. When clustered solid supports 13 are used as the target materials 11C, 11D, water may be used as the fluid 56".

Moreover, the density of the fluid 56" and the target materials 11C, 11D may be approximately equal so that the density of the target materials 11C, 11D does not interfere with the electrostatically induced migration of the target materials 11C, 11D. In another example, the density of the fluid 56" and the target materials 11C, 11D may not be equal. In this example, the strength of the force due to the applied electric field 62 is greater than any force due to the difference in density.

In this example method, the condition to which the charged target materials 11C, 11D are exposed to initiate simultaneous migration and immobilization is an electric field 62 applied between the two opposed sequencing surfaces 30 and 30', 32 and 32', or 31 and 31' to generate positive charges 66 at the first of the two opposed sequencing surfaces 30, 32, 31 and negative charges 68 at the second of the two opposed sequencing surface 30', 32', 31'.

To generate the electric field 62 across the flow cell 24, each sequencing surface 30, 30' or 32, 32' or 31, 31' can be electrically coupled to a power source to produce the respective electric charges 66, 68 that attract the respective target materials 11C, 11D. In the example shown in FIG. 6A and FIG. 6B, the electric field 62 is applied in the direction towards the lower/bottom sequencing surface 30', resulting in the upper sequencing surface 30 being positively charged and the lower/bottom sequencing surface 30' being negatively charged.

The immobilization of the target materials 11C, 11D occurs simultaneously upon exposure of fluid 56" in the flow cell 24 to the electric field 62. This is due to the positive and negative charges of the target materials 11C, 11D and their respective responses to the applied electric field 62. The negatively charged target material 11C migrates toward the now positively charged sequencing surface 30, where it becomes immobilized by the capture sites 44 (not shown in FIG. 6B) of the upper sequencing surface 30. The positively charged target material 11D migrates toward the now negatively charged sequencing surface 30', where it becomes immobilized by the capture sites 44 (not shown in FIG. 6B) of the lower/bottom sequencing surface 30'.

The electric field 62 may be applied for a predetermined time. In an example, the predetermined time may range from about 1 minute to about 30 minutes in order to obtain a desirable number of immobilized target materials 11C, 11D on the respective sequencing surfaces 30, 30'. In other examples, the electric field 62 may be applied for a time ranging from about 1 minute to about 2 minutes, or from about 1 minute to about 5 minutes, or from about 5 minutes of about 30 minutes, etc.

It is to be understood that some target materials 11C, 11D may not become immobilized, and these target materials 11C, 11D will be removed from the flow cell 24 before further processing. The electric field 62 may be ceased prior to removal of non-immobilized target materials 11C, 11D. As such, this example method may include, removing the electric field 62, and then washing away the fluid 56" and non-immobilized target material 11C, 11D from the flow cell 24. Washing may involve introducing a washing fluid into the flow cell 24. The flow may push any target materials 11C, 11D that have not become immobilized at the sequencing surfaces 30, 30' out through an exit port of the flow cell 24. The immobilization mechanism (e.g., binding pair, hybridization, covalent bonding, etc.) between the respective target materials 11C, 11D and the capture sites 44, 44' of the sequencing surfaces 30, 30' may prevent any immobilized target materials 11C, 11D from becoming part of the exit flow.

When complexes 10A or 10B are used as the target materials 11C, 11D, this washing step may be followed by library fragment release and amplification (e.g., an example of which is described in reference to FIG. 9A through FIG. 9C). When clustered solid supports 13 are used, this washing step may be followed by sequencing.

Figure 7A:
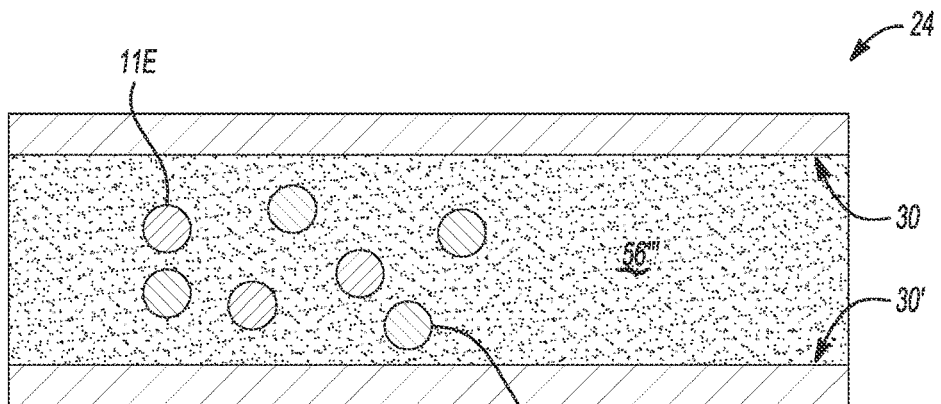
FIGS. 7A and 7B together depict an additional example of a method disclosed herein.
Figure 7B:
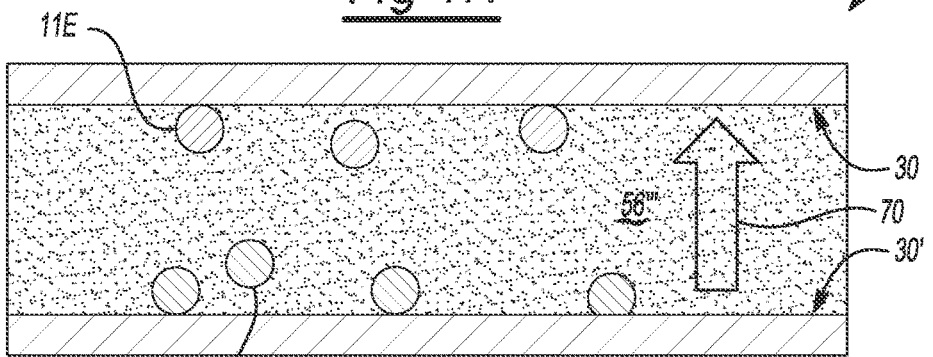

Another example method is shown in FIG. 7A and FIG. 7B. In this example, the target materials 11E, 11F are different in terms of magnetism and density.

In this example (as shown in FIG. 7A), the target materials 11E, 11F are introduced into the flow cell 24 in a fluid 56''' which has a first density. As is described in more detail below, the density of each of the target materials 11E, 11F is selected with respect to this first density, i.e., the density of the fluid 56''' at the capture temperature of the target materials 11E, 11F. The capture temperature ranges from about 18° C. to about 40° C.

In the example shown in FIG. 7A and FIG. 7B, the first target material 11E is magnetic, and the second target material 11F is non-magnetic and has a density greater than the first density (i.e., the density of the fluid 56''' at the capture temperature).

In this example, the first target material 11E includes any of the magnetically responsive solid supports 12' disclosed herein. Additionally, the density of the fluid 56''' and the target material 11E may be approximately equal so that the density of the target material 11E does not interfere with the magnetically induced migration of the target material 11E. In another example, the density of the fluid 56''' and the target material 11E may not be equal. In this example, the strength of the force due to the applied magnetic field 70 is greater than any force due to the difference in density.

Also in this example, the second target material 11F includes any of the solid supports 12 disclosed herein that are not magnetically responsive. The density of the solid support 12, and thus the target material 11F, is greater than the density of the fluid 56''' at the capture temperature. As such, the target material 11F is non-responsive to the applied magnetic field and is able to migrate to or settle on the bottom sequencing surface 30' due to it being heavier than the fluid 56'''.

In this example method, the fluid 56''' including the target materials 11E, 11F is introduced into the flow cell 24 (FIG. 7A), and the condition to which the target materials 11E, 11F are exposed to initiate simultaneous migration and immobilization is the application of a magnetic force 70 (FIG. 7B). The density of the fluid 56''' may also be considered a condition that affects the migration and immobilization.

The magnetic force (or magnetic field 70 as shown in FIG. 7B) may be applied as described in reference to FIG. 4A and FIG. 4B. In the example shown in FIG. 7B, the magnetic force/field 70 is applied in the direction of the upper sequencing surface 30 so that the magnetically responsive (first) target material 11E migrates in that same direction toward the upper sequencing surface 30. The capture sites 44 (not shown in FIG. 7A or FIG. 7B) immobilize at least some of the target material 11E at the upper sequencing surface 30. At the same time, the solid support 12 of the target material 11F is not magnetically responsive and is heavier than fluid 56''' at the capture temperature. As such, the target material 11F migrates to or settles on the bottom sequencing surface 30', as shown in FIG. 7B. The capture sites 44' (also not shown in FIG. 7A or FIG. 7B) immobilize at least some of the target material 11F at the lower/bottom sequencing surface 30'.

The magnetic force/field 70 may be applied for a predetermined time. In an example, the predetermined time may range from about 5 minutes to about 30 minutes in order to obtain a desirable number of immobilized target materials 11E on the sequencing surfaces 30.

The immobilization of the target materials 11E, 11F occurs simultaneously upon introduction of the target fluid 56''' to the flow cell 24 and upon exposure to the magnetic field 70 due to the properties (both density and magnetism) of the target materials 11E, 11F. In the method of FIG. 7A and FIG. 7B, at least some of the first target material 11E becomes immobilized by respective capture sites 44 on the first of the two opposed sequencing surfaces 30, and at least some of the second target material 11F becomes immobilized by respective capture sites 44' on the second of the two opposed sequencing surfaces 30'.

It is to be understood that some target materials 11E, 11F may not become immobilized, and these target materials 11E, 11F will be removed from the flow cell 24 before further processing. The magnetic force/field 70 may be ceased prior to removal of non-immobilized target materials 11E, 11F. As such, this example method may include, removing the magnetic force/field 70, and then washing away the fluid 56''' and non-immobilized target material 11E, 11F from the flow cell 24. Washing may involve introducing a washing fluid into the flow cell 24. The flow may push any target materials 11E, 11F that have not become immobilized at the sequencing surfaces 30, 30' out through an exit port of the flow cell 24. The immobilization mechanism (e.g., binding pair, hybridization, covalent bonding, etc.) between the respective target materials 11E, 11F and the capture sites 44, 44' of the sequencing surfaces 30, 30' may prevent any immobilized target materials 11E, 11F from becoming part of the exit flow.

When complexes 10A or 10B are used as the target materials 11E, 11F, this washing step may be followed by library fragment release and amplification (e.g., an example of which is described in reference to FIG. 9A through FIG. 9C). When clustered solid supports 13 are used as the target materials 11E, 11F, this washing step may be followed by sequencing.

The example method shown in FIG. 7A and FIG. 7B may also be performed so that the target material 11E that is magnetically responsive is immobilized on the lower/bottom sequencing surface 30' and the target material 11F that is non-magnetically responsive is immobilized on the upper sequencing surface 30. In this example, the non-magnetically responsive target material 11F includes the solid support 12 that is selected to have a density less than the density of the fluid 56''' at the capture temperature. In this example, the target material 11E is responsive to the magnetic force/field (applied in the direction of the bottom sequencing surface 30') and is attracted to the bottom sequencing surface 30', while the target material 11F is non-responsive to the applied magnetic field and is able to float or migrate to the upper sequencing surface 30 due to it being lighter than the fluid 56'''.

Figure 8A:
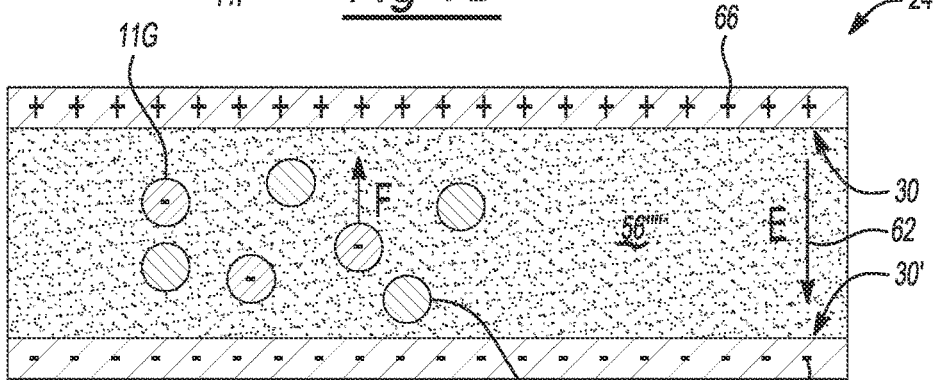
FIGS. 8A and 8B together depict still another example of a method disclosed herein.
Figure 8B:
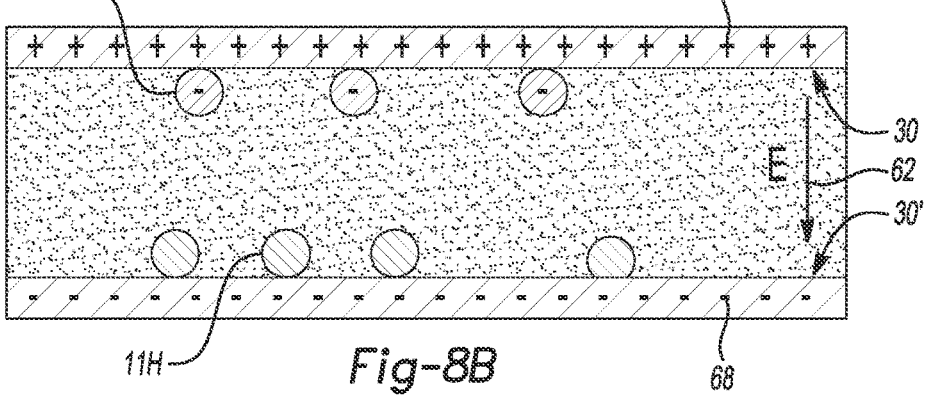

Another example method is shown in FIG. 8A and FIG. 8B. In this example, the target materials 11G, 11H are different in terms of charge and density.

In this example, the target materials 11G, 11H are introduced into the flow cell 24 in a fluid 56'''' which has a first density. As is described in more detail below, the density of each of the target materials 11G, 11H is selected with respect to this first density, i.e., the density of the fluid 56'''' at the capture temperature of the target materials 11G, 11H. The capture temperature ranges from about 18° C. to about 40° C.

In these examples, the fluid 56'''' is an electrolyte.

In the example shown in FIG. 8A and FIG. 8B, the first target material 11G is negatively charged, and the second target material 11H is neutral (not charged) and has a density greater than the first density (i.e., the density of the fluid 56'''' at the capture temperature). In this example, the first target material 11G includes any of the negatively charged solid supports disclosed herein, such as a carboxylated solid support, a polyglutamic acid coated solid support, or a sulfate functionalized solid support. Additionally, the density of the fluid 56'''' and the density of the target material 11G may be approximately equal so that the density of the target material 11G does not interfere with the electrostatically induced migration of the negatively charged target material 11G. Alternatively, the density of the target material 11G may be less than the density of the fluid 56'''', and the density and charge can both aid in migration of the target material 11G.

In other examples of the method represented by FIG. 8A and FIG. 8B, the first target material 11G is positively charged, and the second target material 11H is neutral (not charged) and has a density greater than the first density (i.e., the density of the fluid 56''' at the capture temperature). In this example, the first target material 11G includes any of the positively charged solid supports disclosed herein, such as an amine functionalized solid support (e.g., a chitosan or a polylysine functionalized solid support). Additionally, the density of the fluid 56'''' and the density of the target material 11G may be approximately equal so that the density of the target material 11G does not interfere with the electrostatically induced migration of the positively charged target material 11G. Alternatively, the density of the target material 11G may be less than the density of the fluid 56'''', and the density and charge can both aid in migration of the target material 11G.

In the example methods represented in FIG. 8A and FIG. 8B, the second target material 11H includes any of the solid supports 12 disclosed herein that are not charged. The density of the solid support 12, and thus the target material 11H, is greater than the density of the fluid 56'''' at the capture temperature. As such, the target material 11H is non-responsive to the applied electric field 62 and is able to migrate to or settle on the bottom sequencing surface 30' due to it being heavier than the fluid 56''''.

The fluid 56'''' including the target materials 11G, 11H is introduced into the flow cell 24, and the condition to which the target materials 11G, 11H are exposed to initiate simultaneous migration and immobilization is the application of an electric field 62. The density of the fluid 56'''' may also be considered a condition that affects the migration and immobilization.

The electric field 62 may be applied as described in reference to FIG. 6A and FIG. 6B. In the example shown in FIG. 8A (when the target material 11G is negatively charged), the electric field 62 is applied in the direction towards the lower/bottom sequencing surface 30'. This results in the upper sequencing surface 30 being positively charged and the lower/bottom sequencing surface 30' being negatively charged. In this example, the negatively charged target material 11G migrates toward the now positively charged sequencing surface 30, where it becomes immobilized by the capture sites 44 (not shown in FIG. 8A or FIG. 8B) of the upper sequencing surface 30. At the same time, the solid support 12 of the target material 11H is not charged and is heavier than fluid 56'''' at the capture temperature. As such, the target material 11H migrates to or settles on the bottom sequencing surface 30', as shown in FIG. 8B. The capture sites 44' (also not shown in FIG. 8A or FIG. 8B) immobilize at least some of the target material 11H at the lower/bottom sequencing surface 30'.

As mentioned above, in other examples of the method represented by FIG. 8A and FIG. 8B, the target material 11G is positively charged. In this example, the electric field 62 is applied in the direction towards the upper sequencing surface 30 (i.e., in the opposite direction from that shown in FIG. 8A and FIG. 8B). This results in the lower sequencing surface 30' being positively charged and the upper sequencing surface 30 being negatively charged. In this example, the positively charged target material 11G migrates toward the now negatively charged upper sequencing surface 30, where it becomes immobilized by the capture sites 44 of the upper sequencing surface 30. At the same time, the solid support 12 of the target material 11H is not charged and is heavier than fluid 56'''' at the capture temperature. As such, the target material 11H migrates to or settles on the bottom sequencing surface 30', similar to FIG. 8B. The capture sites 44' (also not shown in FIG. 8B) immobilize at least some of the target material 11H at the lower/bottom sequencing surface 30'.

In any of the examples represented by FIG. 8A and FIG. 8B, the electric field 62 may be applied for a predetermined time. In an example, the predetermined time may range from about 1 minute to about 30 minutes in order to obtain a desirable number of immobilized charged target materials 11G on the oppositely charged sequencing surface 30 or 30'.

The immobilization of the target materials 11G, 11H occurs simultaneously upon introduction of the target fluid 56'''' to the flow cell 24 and upon exposure to the electric field 62 due to the properties (both density and charge) of the target materials 11G, 11H. In the method of FIG. 8A and FIG. 8B, at least some of the first target material 11G becomes immobilized by respective capture sites 44 on the first of the two opposed sequencing surfaces 30, and at least some of the second target material 11H becomes immobilized by respective capture sites 44' on the second of the two opposed sequencing surfaces 30'.

It is to be understood that some target materials 11G, 11H may not become immobilized, and these target materials 11G, 11H will be removed from the flow cell 24 before further processing. The electric field 62 may be ceased prior to removal of non-immobilized target materials 11G, 11H. As such, this example method may include, removing the electric field 62, and then washing away the fluid 56'''' and non-immobilized target material 11G, 11H from the flow cell 24. Washing may involve introducing a washing fluid into the flow cell 24. The flow may push any target materials 11G, 11H that have not become immobilized at the sequencing surfaces 30, 30' out through an exit port of the flow cell 24. The immobilization mechanism (e.g., binding pair, hybridization, covalent bonding, etc.) between the respective target materials 11G, 11H and the capture sites 44, 44' of the sequencing surfaces 30, 30' may prevent any immobilized target materials 11G, 11H from becoming part of the exit flow.

When complexes 10A or 10B are used as the target materials 11G, 11H, this washing step may be followed by library fragment release and amplification (e.g., an example of which is described in reference to FIG. 9A through FIG. 9C). When clustered solid supports 13 are used as the target materials 11G, 11H, this washing step may be followed by sequencing.

The example method shown in FIG. 8A and FIG. 8B may also be performed so that the target material 11G is not charged and has a density that is less than the density of the target fluid 56''''. In this example, the target material 11H is positively charged. In this example, the positively charged target material 11H is responsive to the electric field 62 (applied in the direction of the bottom sequencing surface 30') and is attracted to the bottom sequencing surface 30'. Also in this example, the target material 11G is non-responsive to the applied magnetic field and is able to float or migrate to the upper sequencing surface 30 due to it being lighter than the fluid 56'''.

It is to be understood that other orthogonal modalities may be combined in order to immobilize two different target materials 11. Each target material 11 may be responsive to one of the orthogonal modalities but not the other, which allows the modalities to independently affect one of the target materials 11. For example, a non-charged magnetically responsive target material 11 may be combined with a charged, non-magnetic target material 11. In this example, a magnetic field 70 may be applied in one direction to guide the migration of the non-charged magnetically responsive target material 11 to one 30, 32, 31, of the opposed sequences surfaces 30, 30' or 32, 32', or 31, 31', and an electric field 62 may be applied in the opposite direction to guide the migration of the charged, non-magnetic target material to the other 30', 32', 31' of the opposed sequences surfaces 30, 30' or 32, 32', or 31, 31'. While several examples have been provided, it is contemplated that other target material combinations and modalities may be utilized.

Library Fragment Release from Complexes and Sequencing

With the target material 11 immobilized on both of the opposed surfaces 30 and 30' or 32 and 32' or 31 and 31' of the flow cell 24, the flow cell 24 is ready for downstream analysis.

In the examples utilizing the complexes 10A, 10B immobilized on both of the opposed sequences surfaces 30 and 30' or 32 and 32', the flow cell 24 is ready for library fragment release, amplification, and sequencing.

After immobilization and removal of non-immobilized target material (e.g., complexes 10A, 10B) examples of the method include initiating release of the sequencing-ready nucleic acid fragments 14, 14', 14'' from the solid support 12 or 12' of immobilized complexes 10A, 10B, thereby seeding at least some the sequencing-ready nucleic acid fragments 14, 14', 14'' to respective primers 42, 42' of the two opposed sequencing surfaces 30, 30' or 32, 32'; and removing the solid support 12 or 12' and non-seeded sequencing-ready nucleic acid fragments 14, 14', 14". These steps may be followed by any of the amplification techniques described herein, including that described in reference to FIG. 9A through FIG. 9C.

Prior to fragment 14, 14', 14" release, an external immobilization agent may be introduced to the flow cell 24. In an example, the external immobilization agent is air, or a liquid medium or a viscous medium that is not miscible with the target material 11 (specifically, the complexes 10A, 10B) that have been introduced to the flow cell 24. Air may be used to aspirate the washing fluid out of the flow cell 24, which can create a liquid droplet that surrounds the complexes 10A, 10B and forms a diffusion barrier around each of the complexes 10A, 10B. The liquid or viscous external immobilization agent at least partially surrounds the complexes 10A, 10B that are immobilized within the flow cell 24. The external immobilization agent can help to minimize diffusion of the sequencing-ready nucleic acid fragments 14, 14', 14" when the fragments 14, 14', 14" are released from the solid supports 12 or 12'. When the external immobilization agent is a temperature responsive material, raising the temperature to the seeding temperature may render the agent more viscous and in a form that can further minimize library diffusion.

The release of the sequencing-ready nucleic acid fragments 14, 14', 14" from the solid support 12 or 12' may then be initiated. In one example, a cleaving agent may be introduced into the flow cell 24, and a stimulus may be applied to trigger the cleaving agent to release the sequencing-ready nucleic acid fragments 14, 14', 14" from the solid support 12 or 12'. In other examples, the release of the sequencing-ready nucleic acid fragments 14, 14', 14" may involve heating the flow cell 24 above a melting temperature of a primer that is hybridized to the fragments 14, 14', 14".

Upon release, transport and seeding of the sequencing-ready nucleic acid fragments 14, 14', or 14" may be restricted by the external immobilization agent. As such, the fragments 14, 14', or 14" of any particular complex 10A, 10B, may be confined to an area of the sequencing surface 30, 30' or 32, 32' near the particular complex 10A, 10B from which the fragments 14, 14', or 14" are released.

The primers 42, 42' of the respective sequencing surfaces 30, 30' or 32, 32' of the flow cell 24 can seed the released sequencing-ready nucleic acid fragments 14, 14', or 14". Seeding is accomplished through hybridization between the first or second sequence of the fragment 14, 14', or 14" and a complementary one of the primers 42, 42' of the respective sequencing surfaces 30, 30' or 32, 32'. Seeding may be performed at a suitable hybridization temperature for the fragment 14, 14', or 14" and the primer(s) 42, 42'. In one example, seeding takes place at about 80° C., which is followed by a temperature reduction down to room temperature (e.g., 25° C.).

The location at which the sequencing-ready nucleic acid fragments 14, 14', or 14" seed within the flow cell 24 depends, in part, upon how the primers 42, 42' are attached. In examples of the flow cell 24 having the non-patterned sequencing surfaces 30, 30', the released sequencing-ready nucleic acid fragments 14, 14', or 14" will seed across polymeric hydrogels 40, 40' in the concave regions 38, 38'. In examples of the flow cell 24 having the patterned sequencing surfaces 32, 32', the released sequencing-ready nucleic acid fragments 14, 14', or 14" will seed across polymeric hydrogels 40, 40' within each of the depressions 48, 48'.

An example of the seeded sequencing-ready nucleic acid fragments 14, 14', or 14" in different depressions 48, 48' along the patterned sequencing surfaces 32, 32' of the flow cell 24 is shown in FIG. 9A.

The solid supports 12, 12' may then be removed from the flow cell 24. Removal of the solid supports 12, 12' may involve any suitable technique, which depends upon the mechanism attaching the solid support 12, 12' to the capture site 44, 44'. As examples, denaturing, bond cleaving, etc. may be used. Removal of the solid supports 12, 12' may also remove non-seeded sequencing-ready nucleic acid fragments 14, 14', 14". Removal of the solid supports 12, 12' may also remove liquid or viscous forms of the external immobilization agent.

The seeded sequencing library fragments 14, 14', 14" can then be amplified using cluster generation.

In one example of cluster generation, the sequencing-ready nucleic acid fragments 14, 14', or 14" are copied from the hybridized primers 42, 42' by 3' extension using a high-fidelity DNA polymerase. The high-fidelity DNA polymerase may be part of an amplification mix that is introduced into the flow cell 24. The amplification mix may also include other suitable polymerase chain reaction reagents. The original sequencing-ready nucleic acid fragments 14, 14', or 14" are denatured, leaving the copies immobilized to the sequencing surfaces 30, 30' or 32, 32'. Isothermal bridge amplification or some other form of amplification may be used to amplify the immobilized copies. For example, the copied templates loop over to hybridize to an adjacent, complementary primer 42, 42', and a polymerase copies the copied templates to form double stranded bridges, which are denatured to form two single stranded strands. These two strands loop over and hybridize to adjacent, complementary primers 42, 42' and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. Clustering results in the formation of several template polynucleotide strands along the sequencing surfaces 30, 30' or 32, 32'. This example of clustering is bridge amplification, and is one example of the amplification that may be performed. It is to be understood that other amplification techniques may be used, such as the exclusion amplification (Examp) workflow (Illumina Inc.).

Another example of amplification, and thus cluster generation, involves the use of a temperature responsive material. This example is shown schematically in FIG. 9A through FIG. 9C. This example method involves introducing an amplification mix, including a liquid form 63 of a temperature responsive material, to the flow cell 24; causing the liquid form 63 of the temperature responsive material to gel (which generates the gel form 63' of the temperature responsive material); initiating amplification of the seeded sequencing-ready nucleic acid fragments 14, 14', 14" to generate template strands 64, whereby the gel form 63' of the temperature responsive material reduces diffusion of the template strands 64; causing the gel form 63' of the temperature responsive material to liquefy (which generates the liquid form 63 of the temperature responsive material); and removing the liquid form 63 of the temperature responsive material from the flow cell 24.

As shown in FIG. 9A, the amplification mix, including the liquid form 63 of the temperature responsive material, has been introduced into the flow channel 28, e.g., via an inlet.

In addition to the liquid form 63 of the temperature responsive material, this example of the amplification mix also includes the high-fidelity DNA polymerase and any other suitable polymerase chain reaction reagents.

The temperature responsive material is able to transition from the liquid form 63 to the gel form 63' by changing the temperature conditions to which the material is exposed. In the liquid form 63, the molecules of the temperature responsive material are unlinked and thus are able to flow. In the gel form 63', the molecules of the temperature responsive material are crosslinked, and thus are unable to flow. The gel form 63' includes pores, channels or other openings that can i) facilitate the diffusive exchange of small molecules, proteins and reagents to access the seeded sequencing-ready nucleic acid fragments 14, 14', 14" for amplification, and also ii) impede or prevent the movement of the seeded sequencing-ready nucleic acid fragments 14, 14', 14" or template strands 64 due to diffusion or convection. As such, any temperature sensitive material that i) facilitates in-gel amplification, ii) limits the diffusion, convection, or other movement of the seeded sequencing-ready nucleic acid fragments 14, 14', 14" and template strands 64, iii) can be pumped or otherwise flowed as a liquid before crosslinking, iv) can be controllably crosslinked and gelled, and v) can be controllably unlinked and liquefied.

Examples of the temperature responsive material include disulfide crosslinked polyacrylamide, agarose, alginate, and a copolymer of poly(N-isopropylacrylamide) (PNIPAAm) and polyethylene glycol (PEG). For each of these materials, amplification may be performed at temperatures that will not melt the gel form 63'.

The copolymer of PNIPAAm and PEG is a liquid at lower temperatures and a gel at higher temperatures. One example of the copolymer of PNIPAAm and PEG is a liquid at temperatures less than 29° C. and a gel at temperatures higher than 32° C. The gelling temperature of the copolymer of PNIPAAm and PEG may be tuned by altering the ratio of the poly(N-isopropylacrylamide) and polyethylene glycol in the copolymer.

The amplification mix is loaded into the flow cell 24 at conditions where the amplification reaction does not occur. For example, amplification does not occur at 4° C., and thus the amplification mix (including the liquid form 63 of the temperature responsive material) may be introduced at this temperature.

Causing the liquid form 63 of the temperature responsive material to gel, and thus generating the gel form 63', may be performed by adjusting the temperature of the flow cell 24, and the temperature responsive material contained therein, to a gelation temperature of the temperature responsive material. The gel form 63' is shown in FIG. 9B. The temperature to which the flow cell 24 is adjusted will depend upon the temperature responsive material being used.

Initiating amplification of the seeded sequencing-ready nucleic acid fragments 14, 14', 14" generates template strands 64, as shown in FIG. 9B. Amplification may be initiated by adjusting the temperature of the flow cell 24, and the amplification mix contained therein, to a temperature where the PCR reagents are active. During amplification, the gel form 63' of the temperature responsive material reduces movement of the seeded sequencing-ready nucleic acid fragments 14, 14', 14" and the template strands 64.

Causing the gel form 63' of the temperature responsive material to liquefy, and thus generating the liquid form 63, may be performed by again adjusting the temperature of the flow cell 24 and the temperature responsive material contained therein, to a liquefaction temperature of the temperature responsive material. Again, the temperature to which the flow cell 24 is adjusted will depend upon the temperature responsive material being used.

The liquid form 63 may then be pumped out of the flow cell 24, readying the flow cell 24 for subsequent sequencing. The flow cell 24 after the liquid form 63 of the temperature responsive material is removed is shown in FIG. 9C.

In one specific example, the copolymer of PNIPAAm and PEG is used in the amplification mix and used in conjunction with recombinase-mediated polymerase chain reaction (PCR). A temperature program may be used to control the amplification as a typical recombinase-mediated isothermal PCR is inactive at 4° C. and active at 37° C. or other high temperatures, and the copolymer of PNIPAAm and PEG is a liquid at temperatures less than 29° C. and a gel at temperatures higher than 32° C. In this example, the amplification mix may be introduced into the flow cell 24 at about 4° C. as a liquid mixture. The temperature may then be raised to about 37° C. to both gel the copolymer and start the PCR amplification. Upon completion, the gel form 63' of the copolymer may be liquefied by lowering the temperature to less than 29° C., e.g., to about 8° C. (which is a suitable sequencing temperature). The liquid form 63 may then be pumped out of the flow cell 24, readying the flow cell 24 for subsequent sequencing.

The use of the temperature responsive material 63, 63' can minimize the diffusion of seeded sequencing-ready nucleic acid fragments 14, 14', or 14" and the amplified template strands 64 from moving (e.g., as a result of diffusion or free convection) to a nearby depression 48, 48' of the patterned sequencing surfaces 32, 32' or away from an initial seeding location on the non-patterned sequencing surfaces 30, 30'. By limiting or preventing this movement, the clusters remain in relatively isolated areas of the flow cell 24, which enables each cluster to be read individually, without redundancy. Movement can also generate hybrid molecules that are not present in the original sequencing library fragments 14, 14', 14", which results in inaccurate sequencing data. By limiting or preventing this movement, these hybrid molecules are not generated, thus improving the accuracy of the resulting sequencing data.

While FIG. 9A through FIG. 9C depicts the flow cell 24 with the patterned sequencing surfaces 32, 32', it is to be understood that the method may be performed using the non-patterned sequencing surfaces 30, 30' as well.

Moreover, the method shown in FIG. 9A through FIG. 9C may be performed with any sequencing-ready nucleic acid fragments 14, 14', 14", including those that are not tethered to a solid support 12, 12'. In this example, any suitable library preparation technique may be used that adds the desired adapters to the fragmented DNA sample. The sequencing-ready nucleic acid fragments 14, 14', 14" may be introduced and seeded on the flow cell sequencing surface(s) 30, 30' or 32, 32'. Once the library fragments are seeded, the method described in FIG. 9A through FIG. 9C may be performed.

It is to be further understood that the method shown in FIG. 9A through FIG. 9C may not be performed with the clustered solid supports 13, as these target materials 11 are not exposed to amplification on the flow cell 24.

A sequencing primer may then be introduced that hybridizes to a complementary sequence on the template polynucleotide strand. This sequencing primer renders the template polynucleotide strand 64 ready for sequencing. The 3'-ends of the templates 64 and any flow cell-bound primers 42, 42' (not attached to the copy) may be blocked to prevent interference with the sequencing reaction, and in particular, to prevent undesirable priming.

To initiate sequencing, an incorporation mix may be added to the flow cell 24. In one example, the incorporation mix includes a liquid carrier, a polymerase, and fluorescently labeled nucleotides. The fluorescently labeled nucleotides may include a 3' OH blocking group. When the incorporation mix is introduced into the flow cell 24, the fluid enters the flow channel 28, and in some examples, into the depressions 48, 48' (where the template polynucleotide strands are present).

The fluorescently labeled nucleotides are added to the sequencing primer (thereby extending the sequencing primer) in a template dependent fashion such that detection of the order and type of nucleotides added to the sequencing primer can be used to determine the sequence of the template. More particularly, one of the nucleotides is incorporated, by a respective polymerase, into a nascent strand that extends the sequencing primer and that is complementary to the template polynucleotide strand. In other words, in at least some of the template polynucleotide strands across the flow cell 24, respective polymerases extend the hybridized sequencing primer by one of the nucleotides in the incorporation mix.

The incorporation of the nucleotides can be detected through an imaging event. During an imaging event, an illumination system (not shown) may provide an excitation light to the respective sequencing surfaces 30, 30' or 32, 32'.

In some examples, the nucleotides can further include a reversible termination property (e.g., the 3' OH blocking group) that terminates further primer extension once a nucleotide has been added to the sequencing primer. For example, a nucleotide analog having a reversible terminator moiety can be added to the sequencing primer such that subsequent extension cannot occur until a deblocking agent is delivered to remove the moiety. Thus, for examples that use reversible termination, a deblocking reagent can be delivered to the flow cell 24 after detection occurs.

Wash(es) may take place between the various fluid delivery steps. The SBS cycle can then be repeated n times to extend the sequencing primer by n nucleotides, thereby detecting a sequence of length n.

In some examples, the forward strands may be sequenced and removed, and then reverse strands are constructed and sequenced as described herein.

While SBS has been described in detail, it is to be understood that the flow cells 24 described herein may be utilized with other sequencing protocol, for genotyping, or in other chemical and/or biological applications. In some instances, the primers 42, 42' of the flow cell 24 may be selected to enable simultaneous paired-end sequencing, where both forward and reverse strands are present on the polymeric hydrogel 40, 40', allowing for simultaneous base calling of each read. Sequential and simultaneously paired-end sequencing facilitates detection of genomic rearrangements and repetitive sequence elements, as well as gene fusions and novel transcripts.

Clustered Solid Supports and Sequencing

As noted above, with the target material 11 immobilized on both of the opposed surfaces 30 and 30' or 32 and 32' or 31 and 31' of the flow cell 24, the flow cell 24 is ready for downstream analysis. When the clustered solid supports 13 are immobilized on both of the opposed surfaces 31 and 31' of the flow cell 24, the flow cell 24 is ready for sequencing. In these examples, the flow cell 24 is ready for sequencing because amplification and cluster generation have taken place on the solid support 12 or 12' off of the flow cell 24.

Sequencing may be performed as described herein by introducing the sequencing primer and incorporation mix, and performing sequential sequencing cycles.

To further illustrate the present disclosure, examples are given herein. It is to be understood that these examples are provided for illustrative purposes and are not to be construed as limiting the scope of the present disclosure.

NON-LIMITING WORKING EXAMPLES

Example 1

Complexes similar to those shown in FIG. 1A were prepared having an average diameter of 3 µm. The solid supports of the complexes were DYNABEADS™ M-280 Streptavidin beads from ThermoFisher Scientific. The solid supports each a density of about 1.18 g/cm$^3$. The fragments on a particular bead were from the same long DNA molecule (from the PhiX genome). The library fragments were attached to the solid support via a desthiobiotin oligo, which has weaker affinity than biotin to streptavidin on the bead surface. The library fragments included P5' and P7 sequences, along with index sequences, and read 1 and read 2 sequences.

The complexes were loaded into a flow cell including opposed patterned sequencing surfaces (including P5 and P7 primers) using an example of the method similar to that described in FIG. 3A and FIG. 3B.

More specifically, the complexes were first divided between two fluids, the first of which had a density of about 2 g/cm$^3$ and the second of which had a density of about 1 g/cm$^3$. The first fluid was a 1 g/ml sodium polytungstate solution (500 mg sodium polytungstate per 500 µL of the saline sodium citrate buffer with sodium dodecyl sulfate), and included the complexes at a concentration of 600,000 complexes per 1 µL. The second fluid was a saline sodium citrate buffer with sodium dodecyl sulfate, and included the complexes at a concentration of 600,000 complexes per 1 µL.

The first fluid was introduced into the flow cell and the complexes were allowed to immobilize to the top surface of the flow cell. The flow cell was then washed with a washing solution. The second fluid was introduced into the flow cell and the complexes were allowed to immobilize to the bottom surface of the flow cell. Attachment of the complexes to the respective surfaces was accomplished with an anchor (e.g., complementary primers with biotin were hybridized to the P5 primers attached to the gel material or alkyne-PEG-biotin linkers were covalently attached to free azides on the gel material using click chemistry).

Figure 10A:
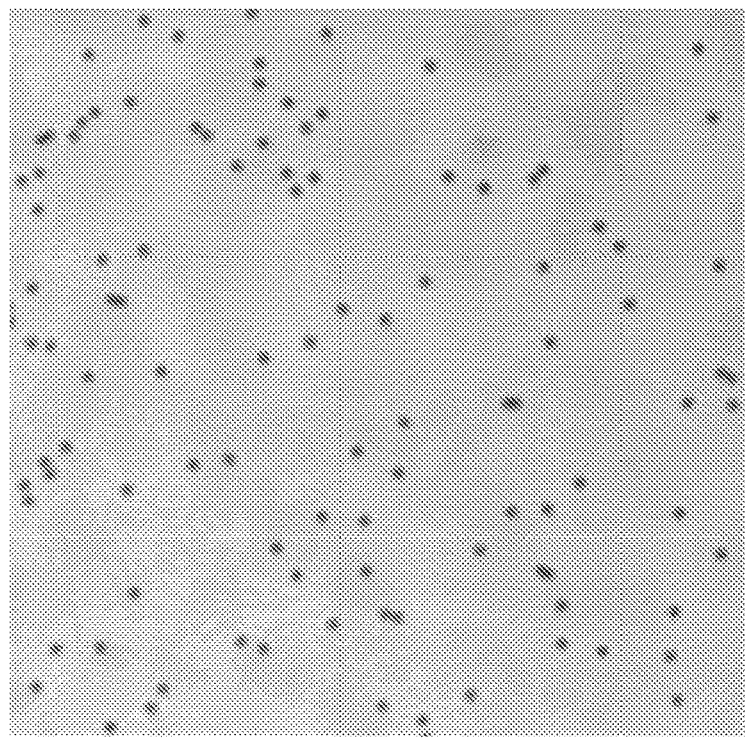
FIGS. 10A and 10B are brightfield images of complexes immobilized on a top sequencing surface (FIG. 10A) and a bottom sequencing surface (FIG. 10B) of a flow cell including patterned sequencing surfaces.
Figure 10B:
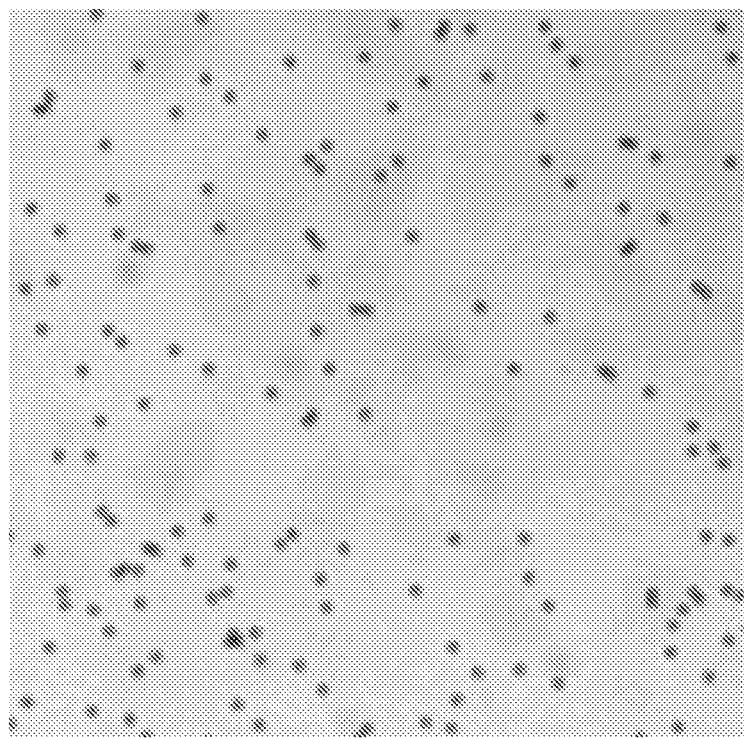

FIG. 10A illustrates a bright field image of the top surface after complex immobilization and FIG. 10B illustrates a bright field image of the bottom surface after complex immobilization. The darker areas of each image depict the immobilized complexes.

Free biotin in saline sodium citrate buffer with sodium dodecyl sulfate was introduced and the flow cell was heated to about 80° C. to release the libraries from the respective complexes. Clustering was performed using isothermal amplification. The clusters were stained with Sytox green and the resulting images (not reproduced herein) confirmed clusters of template strands were formed on each of the sequencing surfaces of the flow cell.

Sequencing was then performed on the flow cell. Some of the sequencing data collected for the top and bottom surfaces of the flow cell is shown in FIG. 11A and FIG. 11B.

Figure 11A:
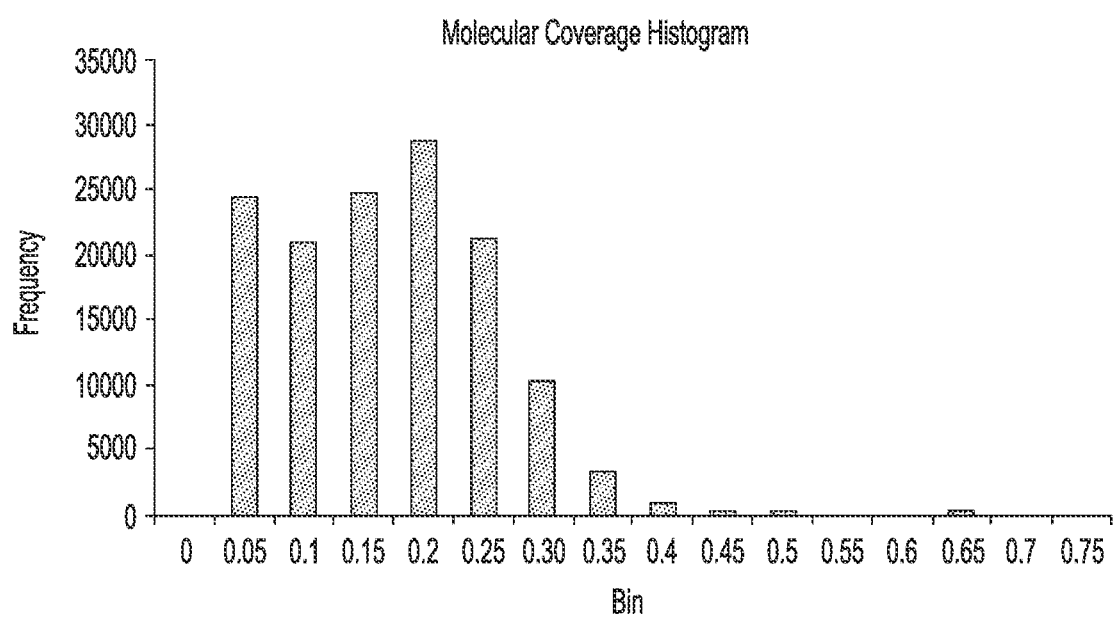
FIG. 11A is a molecular coverage histogram for the top and bottom sequencing surfaces of one lane of a flow cell after sequencing was performed.

FIG. 11A depicts a molecular coverage histogram for one lane of the flow cell on the top and bottom surfaces. This data shows the range and uniformity of sequencing coverage for the lane.

Figure 11B:
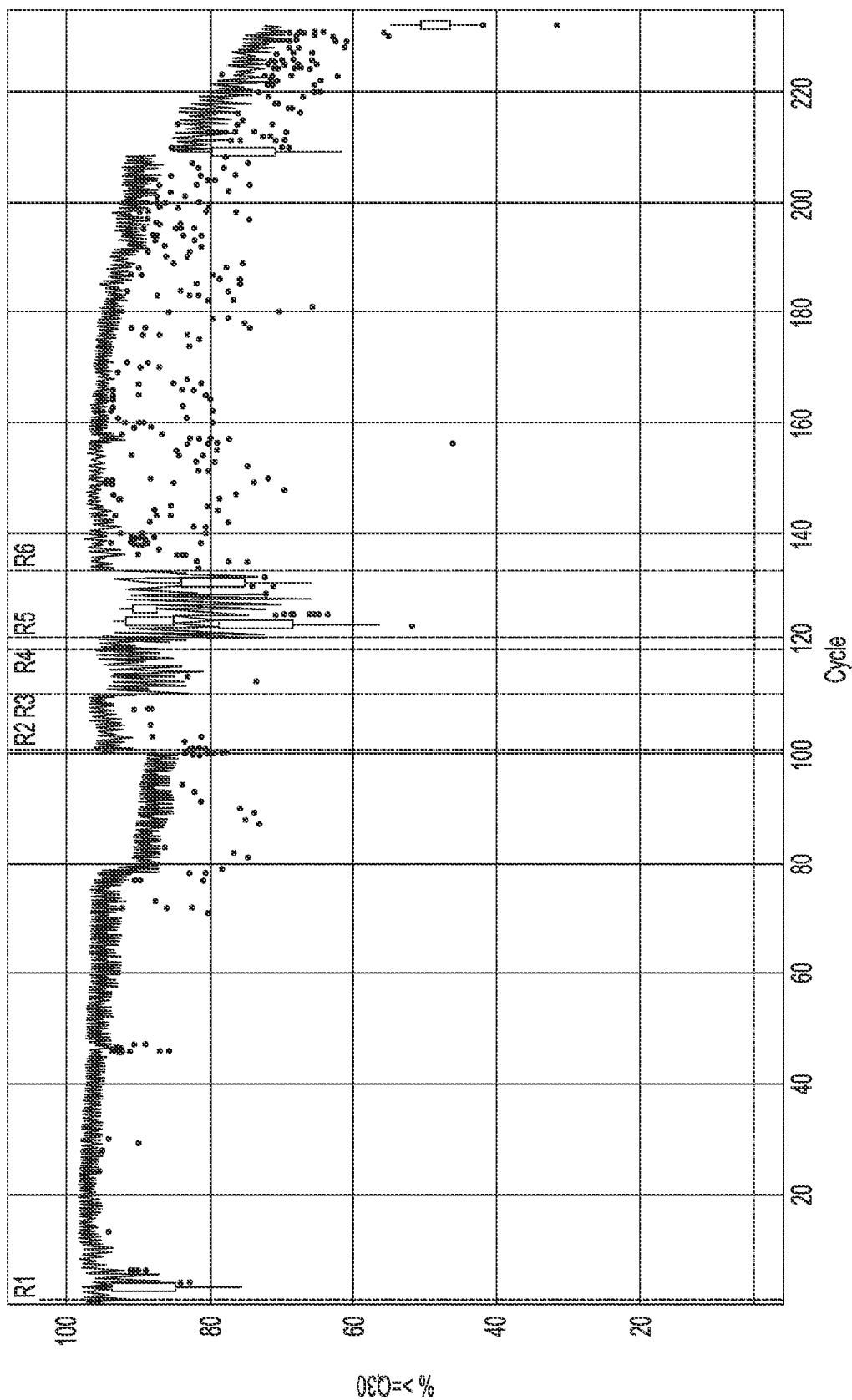
FIG. 11B is a graph depicting the percentage of Qscores greater than Q30 (Y axis) versus sequencing cycle number (X axis) for the top and bottom sequencing surfaces of the one lane after sequencing was performed.

FIG. 11B depicts the percentage of Qscores greater than Q30 for various sequencing cycles in one lane of the flow cell on the top and bottom surfaces. A Qscore of 30 (Q30) is equivalent to the probability of an incorrect base call 1 in 1000 times. This means that the base call accuracy (i.e., the probability of a correct base call) is 99.9%. A lower base call accuracy of 99% (Q20) will have an incorrect base call probability of 1 in 100, meaning that every 100 base pair sequencing read will likely contain an error. When sequencing quality reaches Q30, virtually all of the reads will be perfect, having zero errors and ambiguities. As depicted in FIG. 11B, the percentage of Qscores higher than Q30 generally ranged from 60% to 99% for all sequencing cycles.

All of the collected data confirmed that the more dense fluid (in this example the first fluid) was compatible with the sequencing surface of the flow cell.

Example 2

Complexes similar to those shown in FIG. 1A were prepared having an average diameter of 3 μm. The solid supports of the complexes were DYNABEADS™ M-280 Streptavidin beads from ThermoFisher Scientific. The solid supports each a density of about 1.18 g/cm$^3$. The fragments on a particular bead were from the same long DNA molecule (from the PhiX genome).

In this example, flow cell lanes (having opposed surfaces coated with a gel material) were prepared with different concentrations of capture sites (namely alkyne-PEG-biotin linkers). These linkers were covalently attached to free azides on the gel material in the flow cell lanes using click chemistry. The flow cell lanes were washed and respectively exposed to an alkyne-PEG-biotin solution having concentrations of about 0.5 μM, about 5 μM, or about 25 μM. The solutions were allowed to incubate for about 30 minutes at about 60° C. The flow cell lanes were then washed again.

The complexes were first divided between two fluids, the first of which had a density of about 1 g/cm$^3$ and the second of which had a density of about 2 g/cm$^3$. The first fluid was a saline sodium citrate buffer with sodium chloride, and included the complexes at a concentration of 25,000 per μL. The second fluid was a 2 g/ml sodium polytungstate solution, and included the complexes at a concentration of 25,000 per μL.

The first fluid was introduced into the respective flow cell lanes and the complexes were allowed to immobilize to the bottom surfaces of the flow cell lanes. The aspiration rate was 100 μL/min, and the first fluid remained in the flow cells for 180 seconds. The flow cells were then washed with a washing solution. The second fluid was introduced into the respective flow cell lanes and the complexes were allowed to immobilize to the top surfaces of the flow cell lanes. The aspiration rate was 100 μL/ms, and the second fluid remained in the flow cell lanes for 450 seconds. The flow cell lanes were then washed with a washing solution.

The bottom and top surfaces of each of the flow cell lanes were imaged and the immobilized complexes (beads) on each surface were counted using microscope images.

Figures 12A, 12B:
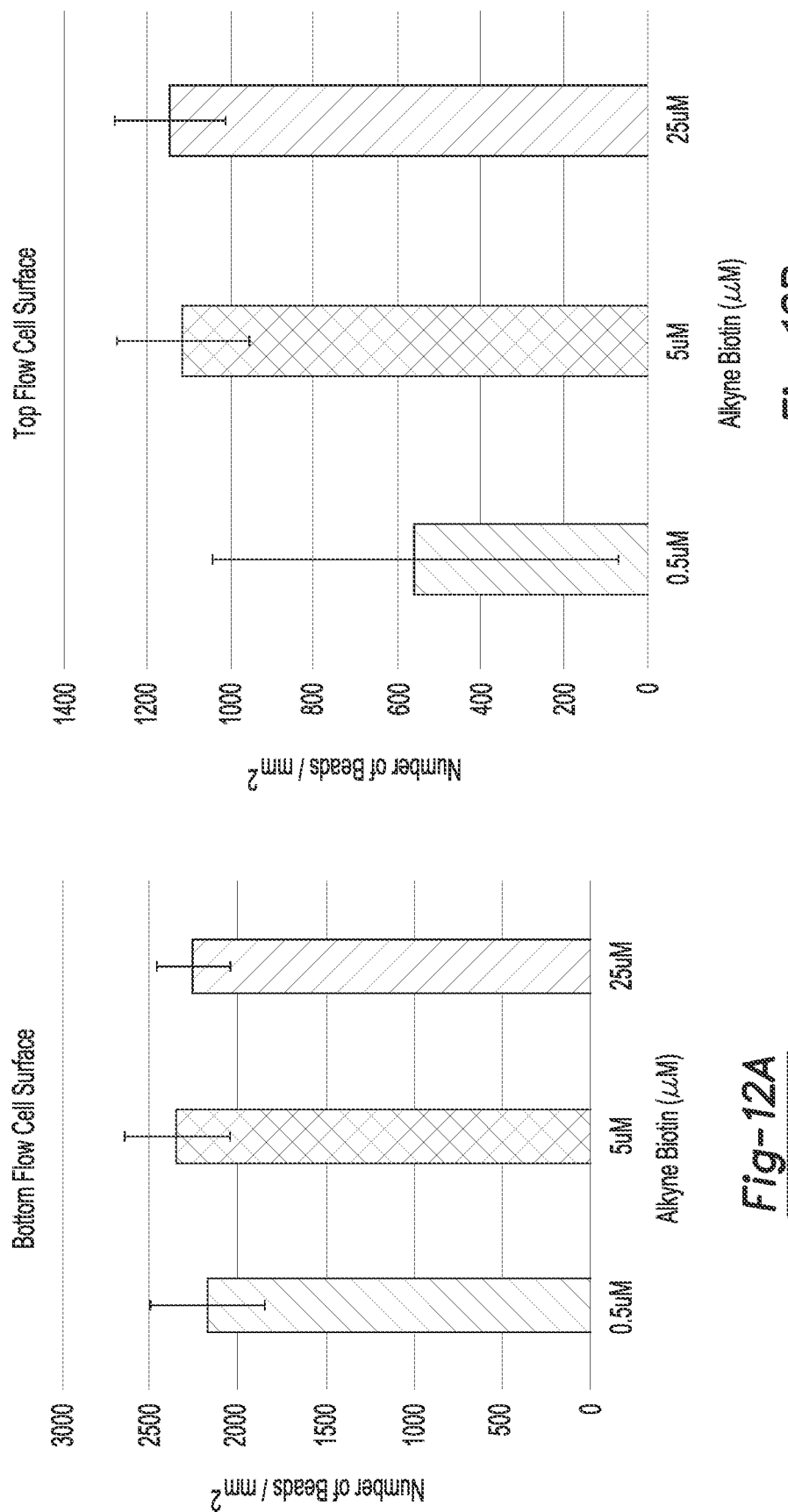
FIGS. 12A and 12B are bar graphs depicting the complex loading (number of beads/mm$^2$, Y axis) on the bottom surfaces (FIG. 12A) and top surfaces (FIG. 12B) of flow cells treated with different concentrations (µM, X axis) of alkyne-biotin, where complex loading was performed using two different introduction liquids.

The number of beads per mm$^2$ for the bottom surfaces are shown in FIG. 12A and the number of beads per mm$^2$ for the top surfaces are shown in FIG. 12B. The concentrations for each bar in FIG. 12A and FIG. 12B represent the alkyne-PEG-biotin concentration (about 0.5 μM, about 5 μM, or about 25 μM) used to prep the flow cells prior to complex immobilization. As depicted, the alkyne-PEG-biotin concentration did not impact the immobilization on the bottom surfaces, as each of these had from about 2,100 beads/mm$^2$ to about 2,300 beads/mm$^2$. The number of complexes immobilized on the top surfaces was not quite as high as the bottom surfaces, as they ranged from about 550 beads/mm$^2$ to about 1,150 beads/mm$^2$. For the top surfaces, the lanes treated with higher concentrations of alkyne-PEG-biotin linkers had a higher number of complexes/beads immobilized thereon.

These results illustrate that the heavier fluid does help to immobilize complexes on the top surfaces, and that increasing the capture size concentration on the top surface can also help with immobilization.

Example 3

Complexes similar to those shown in FIG. 1A were prepared having an average diameter of 3 μm. The solid supports of the complexes were DYNABEADS™ M-280 Streptavidin beads from ThermoFisher Scientific. The solid supports each a density of about 1.18 g/cm$^3$. The fragments on a particular bead were from the same long DNA molecule (from the PhiX genome).

In this example, eight flow cell lanes (having opposed surfaces coated with a gel material) were prepared with capture sites (namely alkyne-PEG-biotin linkers). These linkers were covalently attached to free azides on the gel material in the flow cell lanes using click chemistry. The flow cell lanes were washed and respectively exposed to an alkyne-PEG-biotin solution having concentrations of about 5 μM. The solution was allowed to incubate for about 30 minutes at about 60° C. The flow cell lanes were then washed again.

The complexes were first divided between two fluids, the first of which had a density of about 1 g/cm$^3$ and the second of which had a density of about 2 g/cm$^3$. The first fluid was a sodium citrate buffer, and included the complexes at a concentration of 40,000 per μL. The second fluid was a 2 g/ml sodium polytungstate solution, and included the complexes at a concentration of 40,000 per μL.

The first fluid was introduced into seven of the flow cell lanes and the complexes were allowed to immobilize to the bottom surfaces. The aspiration rate was 100 μL/min, and the first fluid remained in each of the lanes for 240 seconds. The flow cell lanes were then washed with a washing solution. The second fluid was introduced into each of the seven flow cell lanes and the complexes were allowed to immobilize to the top surfaces. The aspiration rate ranged from 80 μL/ms to 100 μL/ms, and the second fluid remained in the flow cells for 300 seconds. The flow cell lanes were then washed with a washing solution.

In the eighth lane, the fluids were diluted to 100 μL each, and the introduction of the respective fluid was performed twice. Thus, lane 8 had a double loading.

The bottom and top surfaces of each of the flow cell lanes were imaged and the immobilized complexes (beads) on each surface were counted. Table 1 provides the average number of beads per mm$^2$ for each of the flow cell lanes.

TABLE 1

| Lane ID | Top Surface (# Complexes/mm²) | Bottom Surface (# Complexes/mm²) |
|---|---|---|
| 1 | 3393 ± 343 | 3335 ± 151 |
| 2 | 2291 ± 583 | 3044 ± 556 |
| 3 | 3576 ± 290 | 3395 ± 281 |
| 4 | 3657 ± 606 | 3148 ± 95 |
| 5 | 3577 ± 467 | 3243 ± 229 |
| 6 | 3877 ± 770 | 3194 ± 245 |
| 7 | 3672 ± 594 | 3629 ± 94 |
| 8 | 6272 ± 2000 | 4389 ± 950 |

The target number of complexes (beads) for each of the surfaces was 4,000 beads/mm². While lanes 1-7 were slightly under target, the number of complexes on the top and bottom surfaces for these lanes was relatively consistent. Lane 8 (exposed to a double loading) exceeded the target number of complexes on both surfaces.

Figure 13A:
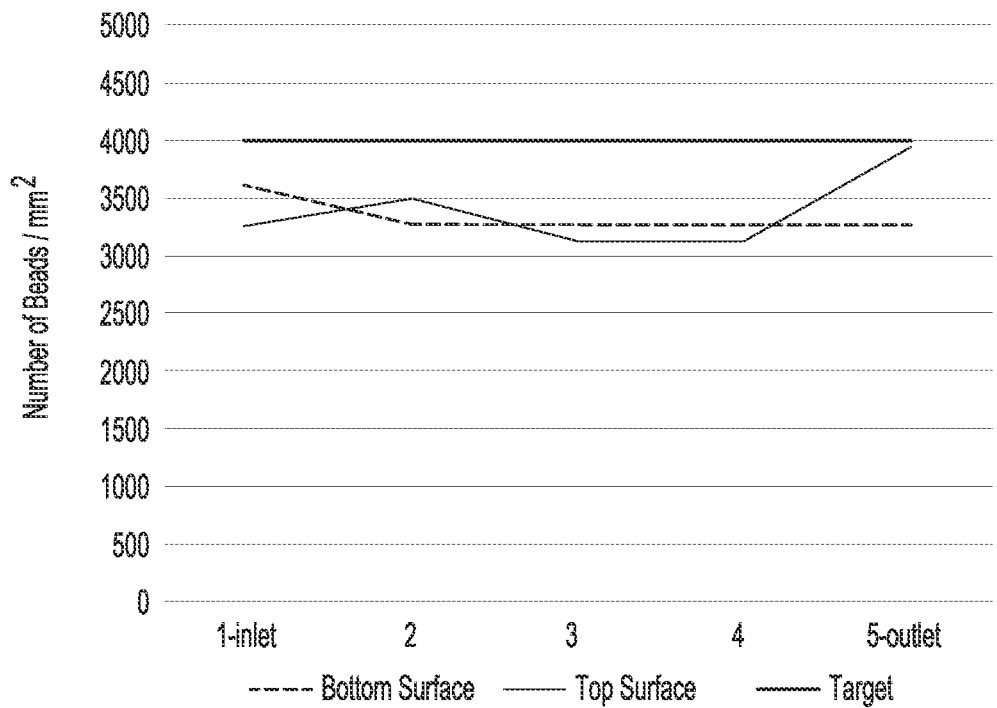
FIGS. 13A and 13B are graphs depicting the target complex loading and the actual the complex loading (number of beads/mm$^2$, Y axis) on a bottom surface and a top surface along the length (X axis) of two different flow cell channels.
Figure 13B:
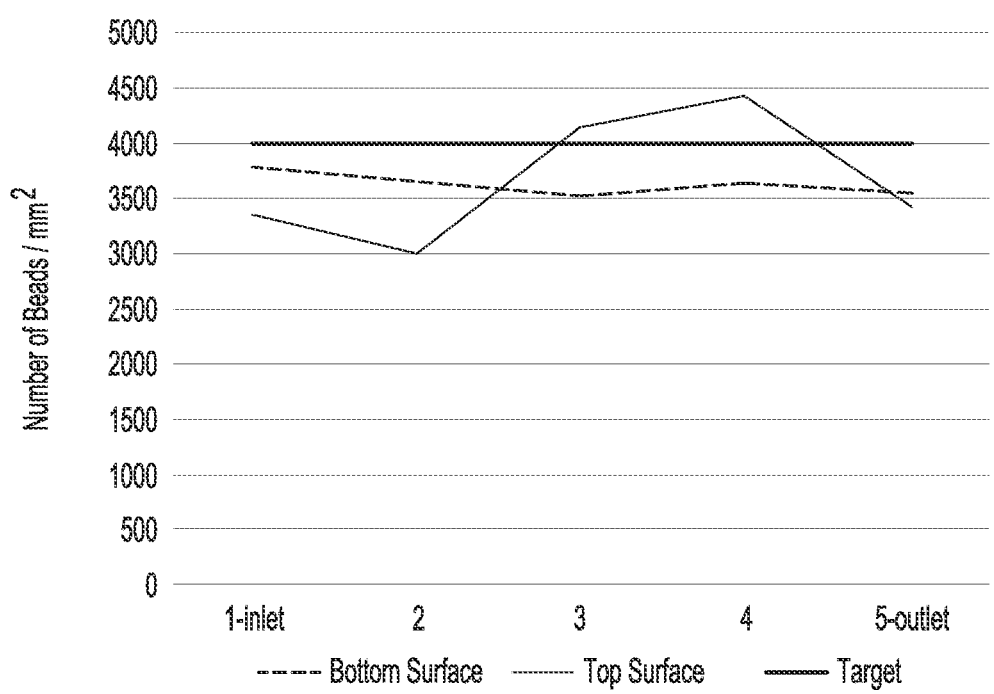

FIG. 13A illustrates the target number of beads and the number of beads per mm² as measured along the length of the flow cell lane 1 from the inlet (1) to the outlet (5). FIG. 13B illustrates the target number of beads, and the number of beads per mm² as measured along the length of the flow cell lane 7 from the inlet (1) to the outlet (5). The measurements were taken at equal distances along the length. These results illustrate that the immobilization is relatively consistent along the length of the flow channel lanes on both the top and bottom surfaces.

Example 4

Complexes similar to those shown in FIG. 1A were prepared having an average diameter of 3 μm. The solid supports of the complexes were DYNABEADS™ M-280 Streptavidin beads from ThermoFisher Scientific. The solid supports each a density of about 1.18 g/cm³. The fragments on a particular bead were from the same long DNA molecule (from the PhiX genome).

In this example, ten flow cell lanes (having opposed surfaces coated with a gel material) were prepared with capture sites (namely alkyne-PEG-biotin linkers). These linkers were covalently attached to free azides on the gel material in the flow cell lanes using click chemistry. The flow cell lanes were washed and respectively exposed to an alkyne-PEG-biotin solution having concentrations of about 5 μM. The solution was allowed to incubate for about 30 minutes at about 60° C. The flow cell lanes were then washed again.

The complexes were first divided between two fluids, the first of which had a density of about 1 g/cm³ and the second of which had a density of about 2 g/cm³. The first fluid was a sodium citrate buffer, and included the complexes at a concentration of 10 μg per 50 μL. The second fluid was a 2 g/ml sodium polytungstate solution, and included the complexes at a concentration of 12.5 μg per 50 μL.

The first fluid was introduced into the ten flow cell lanes and the complexes were allowed to immobilize to the bottom surfaces. The aspiration rate was 100 μL/min, and the first fluid remained in each of the lanes for 300 seconds. The flow cell lanes were then washed with a washing solution. The second fluid was introduced into each of the ten flow cell lanes and the complexes were allowed to immobilize to the top surfaces. The aspiration rate was 80 μL/ms, and the second fluid remained in the flow cells for 360 seconds. The flow cell lanes were then washed with a washing solution.

The bottom and top surfaces of each of the flow cell lanes were imaged and the immobilized complexes (beads) on each surface were counted.

Figure 14:
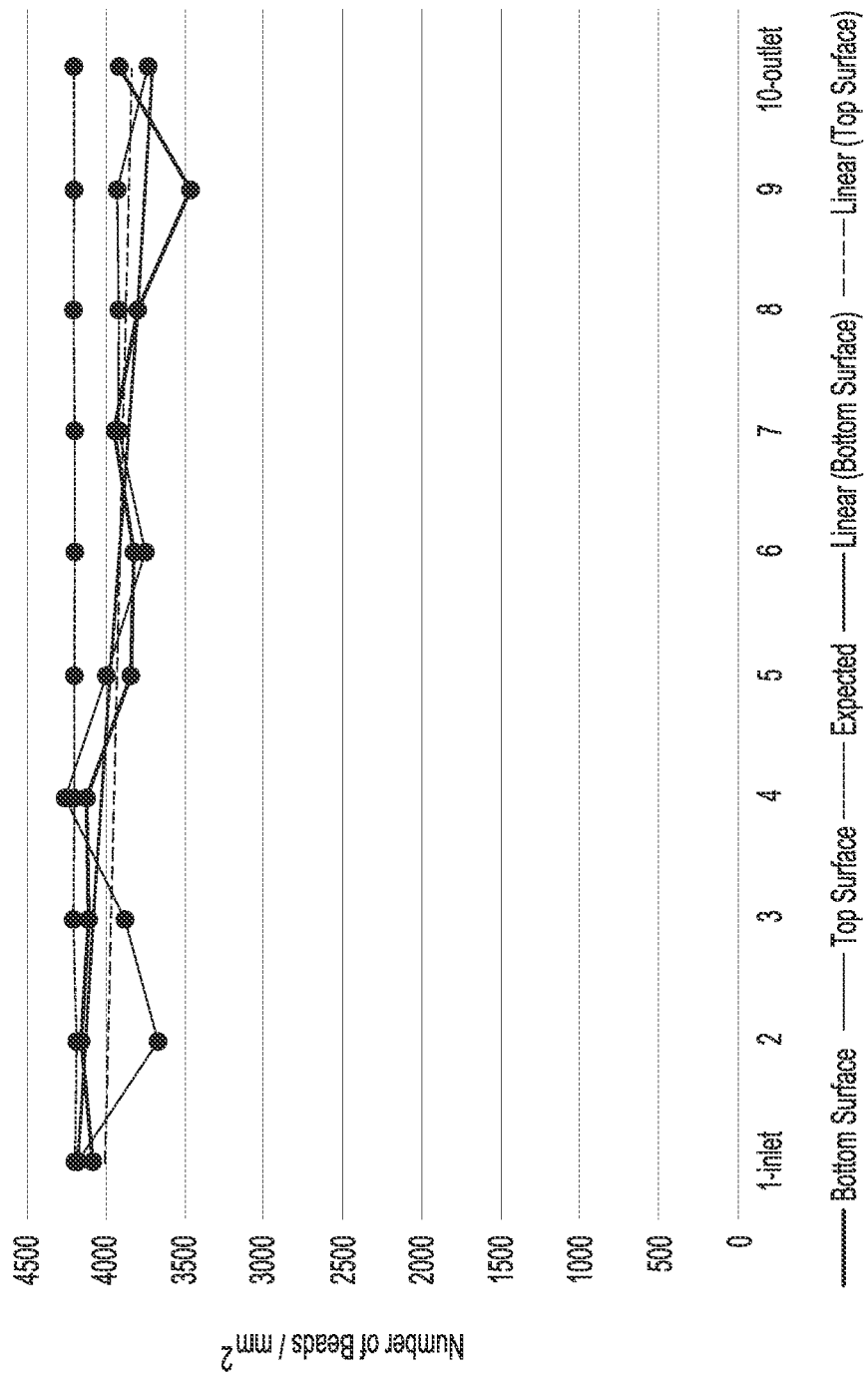
FIG. 14 is a graph depicting the target/expected complex loading, the actual complex loading (number of beads/mm$^2$, Y axis) on a bottom surface and a top surface along the length (X axis) of one flow cell channel, and the linear fit for each surface.

FIG. 14 illustrates the target number of beads, and the number of beads per mm² as measured along the length of one lane of the flow cell from the inlet (1) to the outlet (10). FIG. 14 also illustrates the linear fit for the top surface and bottom surface data. These results illustrate that the immobilization is relatively consistent along the lengths of the top and bottom surfaces of the flow channel when the complexes are introduced in accordance with an example of the method disclosed herein.

Example 5

Complexes similar to those shown in FIG. 1A were prepared having an average diameter of 3 μm. The solid supports of the complexes were DYNABEADS™ M-280 Streptavidin beads from ThermoFisher Scientific. The solid supports each a density of about 1.18 g/cm³. The fragments on a particular bead were from the same long DNA molecule (from the PhiX genome). The library fragments were attached to the solid support via a desthiobiotin oligo, which has weaker affinity than biotin to streptavidin on the bead surface.

In this example, eight flow cell lanes (having opposed surfaces coated with a gel material) were prepared with capture sites (namely alkyne-PEG-biotin linkers). These linkers were covalently attached to free azides on the gel material in the flow cell lanes using click chemistry. The flow cell lanes were washed and respectively exposed to an alkyne-PEG-biotin solution having concentrations of about 5 μM. The solution was allowed to incubate for about 30 minutes at about 60° C. The flow cell lanes were then washed again.

The complexes were first divided between two fluids, the first of which had a density of about 1 g/cm³ and the second of which had a density of about 2 g/cm³. The first fluid was a sodium citrate buffer, and included the complexes at a concentration of 10 μg per 50 μL. The second fluid was a 2 g/ml sodium polytungstate solution, and included the complexes at a concentration of 12.5 μg per 50 μL.

The first fluid was introduced into eight of the flow cell lanes and the complexes were allowed to immobilize to the bottom surfaces. The aspiration rate was 100 μL/min, and the first fluid remained in each of the lanes for 240 seconds. The flow cell lanes were then washed with a washing solution. The second fluid was introduced into each of the eight flow cell lanes and the complexes were allowed to immobilize to the top surfaces. The aspiration rate ranged from 80 μL/ms to 100 μL/ms, and the second fluid remained in the flow cells for 300 seconds. The flow cell lanes were then washed with a washing solution.

The bottom and top surfaces of each of the flow cell lanes were imaged and the immobilized complexes (beads) on each surface were counted.

Free biotin in sodium citrate buffer was introduced and the flow cell was heated to about 80° C. to release the libraries from the respective complexes. Clustering was performed using bridge amplification. Sequencing was then performed on the flow cell. The sequencing data collected included passing filter (% PF) (percentage). Passing filter (PF) is the metric used to describe clusters which pass a chastity threshold and are used for further processing and analysis of sequencing data. A higher % passing filter result indicates an increased yield of unique clusters used for sequencing data.

Table 2 provides the average number of beads per mm² for each of the flow cell lanes, as well as the PF data for each lane.

TABLE 2

| Lane ID | Total Top + Bottom Surfaces (# Complexes/mm²) | % PF |
|---|---|---|
| 1 | 6728 | 58.16 ± 6.4 |
| 2 | 5335 | 64.62 ± 4.74 |
| 3 | 6971 | 65.97 ± 4.18 |
| 4 | 6805 | 66.48 ± 3.59 |
| 5 | 6820 | 65.23 ± 5.29 |
| 6 | 7072 | 65.64 ± 6.76 |
| 7 | 7302 | 71.25 ± 4.33 |
| 8 | 10334 | 66.83 ± 6.85 |

The target number of complexes (beads) for each of the surfaces of lanes 1-7 was 4,000 beads/mm² (8,000 beads/mm² total). The target number of complexes (beads) for each of the surfaces of lane 8 was 5,500 beads/mm² (11,000 beads/mm² total). While lanes 1-8 were slightly under target, the total number of complexes on the top and bottom surfaces for these lanes was relatively consistent. The passing filter data indicated that a majority of the nanowells were occupied by monoclonal clusters.

ADDITIONAL NOTES

Furthermore, it is to be understood that the ranges provided herein include the stated range and any value or sub-range within the stated range, as if they were explicitly recited. For example, a range represented by from about 2 mm to about 300 mm, should be interpreted to include not only the explicitly recited limits of from about 2 mm to about 300 mm, but also to include individual values, such as about 15 mm, 22.5 mm, 245 mm, etc., and sub-ranges, such as from about 20 mm to about 225 mm, etc.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

While several examples have been described in detail, it is to be understood that the disclosed examples may be modified. Therefore, the foregoing description is to be considered non-limiting.

What is claimed is:

1. A method, comprising:
   immobilizing a target material at each of two opposed sequencing surfaces of a flow cell, wherein the immobilizing involves:
      introducing a first fluid, including a first portion of the target material therein, into the flow cell, whereby at least some of the target material becomes immobilized by capture sites on one of the two opposed sequencing surfaces;
      removing the first fluid and any non-immobilized target material from the flow cell; and
      introducing a second fluid, including a second portion of the target material therein, into the flow cell, whereby at least some of the target material becomes immobilized by capture sites on an other of the two opposed sequencing surfaces;
   wherein one of:
      the first fluid has a density less than a density of the target material and the second fluid has a density greater than the density of the target material; or
      the second fluid has the density less than the density of the target material and the first fluid has the density greater than the density of the target material.

2. The method as defined in claim 1, wherein the first or second fluid having the density less than the density of the target material is an aqueous buffer solution, and wherein the second or first fluid having the density greater than the density of the target material is a sodium polytungstate solution or a sodium chloride solution.

3. The method as defined in claim 1, wherein the density of the first or second fluid at a capture temperature is at least 0.1 g/cm³ less than the density of the target material at the capture temperature, and wherein the density of the second or first fluid at the capture temperature is at least 0.1 g/cm³ greater than the density of the target material at the capture temperature.

4. The method as defined in claim 1, wherein the density of the first or second fluid that is less than the density of the target material is about 1 g/cm³ at a capture temperature, and wherein the density of the second or first fluid that is greater than the density of the target material is about 2 g/cm³ at the capture temperature.

5. The method as defined in claim 1, further comprising allowing a predetermined time to pass before removing the first fluid and any non-immobilized target material from the flow cell.

6. The method as defined in claim 1, wherein the target material immobilized on the one of the two opposed sequencing surfaces remains immobilized on the one of the two opposed sequencing surfaces when the second fluid is introduced.

7. The method as defined in claim 1, wherein the target material is a complex including:
   a solid support; and
   sequencing-ready nucleic acid fragments attached to the solid support.

8. The method as defined in claim 7, further comprising:
   removing the second liquid and non-immobilized complexes from the flow cell;
   initiating release of the sequencing-ready nucleic acid fragments from the solid support of immobilized complexes, thereby seeding at least some the sequencing-ready nucleic acid fragments to respective primers of the two opposed sequencing surfaces;
   removing the solid support and non-seeded sequencing-ready nucleic acid fragments;
   introducing an amplification mix including a liquid form of a temperature responsive material to the flow cell;
   causing the liquid form of the temperature responsive material to gel;
   initiating amplification of the seeded sequencing-ready nucleic acid fragments to generate template strands, whereby the gel form of the temperature responsive material reduces diffusion of the template strands;
   causing the gel form of the temperature responsive material to liquify; and
   removing the liquid form of the temperature responsive material from the flow cell.

9. The method as defined in claim 8, wherein the temperature responsive material is a copolymer of poly(N-isopropylacrylamide) and polyethylene glycol.

10. The method as defined in claim 1, wherein the target material is a clustered solid support including:
   a solid support; and
   a cluster of template strands attached to the solid support.

* * * * *

UNITED STATES PATENT AND TRADEMARK OFFICE
CERTIFICATE OF CORRECTION

| | | |
|---|---|---|
| PATENT NO. | : 12,385,091 B2 | Page 1 of 1 |
| APPLICATION NO. | : 17/600526 | |
| DATED | : August 12, 2025 | |
| INVENTOR(S) | : Jeffrey S. Fisher et al. | |

It is certified that error appears in the above-identified patent and that said Letters Patent is hereby corrected as shown below:

In the Claims

In Column 54, Line 4, in Claim 1, delete "an other" and insert -- another --.

Signed and Sealed this
Twenty-first Day of October, 2025

John A. Squires
*Director of the United States Patent and Trademark Office*